United States Patent
Franz et al.

(10) Patent No.: US 11,007,273 B2
(45) Date of Patent: May 18, 2021

(54) PROCHELATORS AS TARGETED PRODRUGS FOR PROSTATE CANCER AND METHODS OF MAKING AND USING SAME

(71) Applicant: Duke University, Durham, NC (US)

(72) Inventors: Katherine J. Franz, Durham, NC (US); Subha Bakthavatsalam, Durham, NC (US); Tian Zhang, Durham, NC (US); Daniel George, Chapel Hill, NC (US); Mark Sleeper, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/628,358

(22) PCT Filed: Jul. 3, 2018

(86) PCT No.: PCT/US2018/040801
§ 371 (c)(1),
(2) Date: Jan. 3, 2020

(87) PCT Pub. No.: WO2019/010231
PCT Pub. Date: Jan. 10, 2019

(65) Prior Publication Data
US 2020/0171160 A1    Jun. 4, 2020

Related U.S. Application Data

(60) Provisional application No. 62/528,591, filed on Jul. 5, 2017.

(51) Int. Cl.
| | |
|---|---|
| *A61K 47/64* | (2017.01) |
| *A61P 35/00* | (2006.01) |
| *A61K 31/167* | (2006.01) |
| *A61K 31/198* | (2006.01) |
| *A61K 38/08* | (2019.01) |

(52) U.S. Cl.
CPC ............ *A61K 47/64* (2017.08); *A61K 31/167* (2013.01); *A61K 31/198* (2013.01); *A61K 38/08* (2013.01); *A61P 35/00* (2018.01)

(58) Field of Classification Search
CPC .... A61K 47/64; A61K 31/167; A61K 31/198; A61K 38/08; A61K 47/65; A61K 47/542; A61K 47/551; A61P 35/00; A61P 37/04; C07K 7/06; C07D 475/04
See application file for complete search history.

(56) References Cited

U.S. PATENT DOCUMENTS

| | | | |
|---|---|---|---|
| 2003/0157052 A1 | 8/2003 | Choe et al. | |
| 2007/0232692 A1* | 10/2007 | Kennedy | A61K 31/27 514/492 |
| 2007/0280880 A1 | 12/2007 | Moser et al. | |
| 2016/0166706 A1* | 6/2016 | Xu | A61K 47/60 424/78.17 |

OTHER PUBLICATIONS

Aggarwal et al., "Emerging Categories of Disease in Advanced Prostate Cancer and Their Therapeutic Implications," Oncology (Williston Park, N.Y.), 2017, 31(6):467-474.
Akam et al., "Disulfide-masked iron prochelators: Effects on cell death, proliferation, and hemoglobin production," Journal of Inorganic Biochemistry, 2018, 180:186-193.
Allensworth et al., "Disulfiram (DSF) acts as a copper ionophore to induce copper-dependent oxidative stress and mediate anti-tumor efficacy in inflammatory breast cancer," Molecular Oncology, 2015, 9(6):1155-1168.
Beer et al., "Enzalutamide in Metastatic Prostate Cancer before Chemotherapy," The New England Journal of Medicine, 2014, 371:424-433.
Beltran et al., "Divergent clonal evolution of castration-resistant neuroendocrine prostate cancer," Nat Med, 2016, 22(3):298-305.
Bramanti et al., "Exogenous vs. endogenous γ-glutamyltransferase activity: Implications for the specific determination of S-nitrosoglutathione in biological samples," Archives of Biochemistry and Biophysics, 2009, 487(2):146-152.
Cai et al., "Reduced $^{64}$Cu Uptake and Tumor Growth Inhibition by Knockdown of Human Copper Transporter 1 in Xenograft Mouse Model of Prostate Cancer," Journal of Nuclear Medicine, 2014, 55(4):622-628.
Capasso et al., "Role of $^{64Cu}Cl_2$ PET/CT in staging of prostate cancer," Annals of Nuclear Medicine, 2015, 29(6):482-488.
Cater et al., "Increasing Intracellular Bioavailable Copper Selectively Targets Prostate Cancer Cells," ACS Chemical Biology, 2013, 8(7):1621-1631.
Cen et al., "Disulfiram facilitates intracellular Cu uptake and induces apoptosis in human melanoma cells," Journal of Medicinal Chemistry, 2004, 47(27):6914-6920.
Choi et al., "Protease-Activated Drug Development," Theranostics 2012; 2(2):156-178.
Coombs et al., "Substrate specificity of prostate-specific antigen (PSA)" Chemistry and Biology, 1998, 5(9):475-488.
Corti et al., "Gamma-glutamyltransferase of cancer cells at the crossroads of tumor progression, drug resistance and drug targeting," Anticancer Research, 2010, 30(4):1169-1181.
CTFA Cosmetic Ingredient Handbook, 1992, pp. 587-592.
De Bono et al., "Abiraterone and increased survival in metastatic prostate cancer," The New England Journal of Medicine, 2011, 364(21):1995-2005.
DeFeo-Jones et al., "A peptide-doxorubicin 'prodrug' activated by prostate-specific antigen selectively kills prostate tumor cells positive for prostate-specific antigen in vivo," Nature Medicine 2000, 6, 1248-1252.
Denmeade et al., "Prostate-Specific Antigen-Activated Thapsigargin Prodrug as Targeted Therapy for Prostate Cancer," Journal of the National Cancer Institute, 2003, 95(13):990-1000.

(Continued)

*Primary Examiner* — Sudhakar Katakam
(74) *Attorney, Agent, or Firm* — Michael Best & Friedrich LLP

(57) ABSTRACT

The present disclosure provides prochelators as targeted prodrugs for cancer, such as prostate cancer, and methods of making and using the same.

14 Claims, 18 Drawing Sheets

Specification includes a Sequence Listing.

(56) References Cited

OTHER PUBLICATIONS

Denmeade et al., "Specific and efficient peptide substrates for assaying the proteolytic activity of prostate-specific antigen," Cancer Research, 1997, 57(21):4924-4930.
Denoyer et al., "Copper as a target for prostate cancer therapeutics: copper-ionophore pharmacology and altering systemic copper distribution," Oncotarget, 2016, 7(24):37064-37080.
DiPaola et al., "Characterization of a novel prostate-specific antigen-activated peptide-doxorubicin conjugate in patients with prostate cancer," Journal of Clinical Oncology, 2002, 20(7):1874-1879.
Elsadek et al., "Optimization of an Albumin-Binding Prodrug of Doxorubicin That Is Cleaved by Prostate-Specific Antigen," ACS Medicinal Chemistry Letters, 2010, 1(5):234-238.
Farci et al., "Disulfiram for binge eating disorder: an open trail," Eating Behaviors, 2015, 16:84-87.
Farmer et al., "Targeting melanoma via metal-based stress," Medicinal inorganic chemistry, 2005, 903:400-414.
Farsehee et al., "Delivery of disulfiram into breast cancer cells using folate-receptor-targeted PLGA-PEG nanoparticles: in vitro and in vivo investigations," Journal of Nanobiotechnology, 2016, 14, 32.
Festa et al., "Exploiting innate immune cell activation of a copper-dependent antimicrobial agent during infection," Chemistry & Biology, 2014, 21(8):977-987.
Gupte et al., "Elevated copper and oxidative stress in cancer cells as a target for cancer treatment," J. Cancer Treat. Rev., 2009, 35(1):32-46.
Hanigan et al., "Gamma-Glutamyl Transpeptidase: Redox Regulation and Drug Resistance," Advances in Cancer Research, 2014, 122:103-141.
Hašková et al., "Cardioprotective effects of iron chelator HAPI and ROS-activated boronate prochelator BHAPI against catecholamine-induced oxidative cellular injury," Toxicology, 2016, 371:17-28.
Iljin et al., "High-throughput cell-based screening of 4910 known drugs and drug-like small molecules identifies disulfiram as an inhibitor of prostate cancer cell growth," Clinical Cancer Research, 2009, 15(19):6070-6078.
IUPAC 1974 Recommendations for Section E, Fundamental Stereochemistry, Pure Appl. Chem., 1976, 45:13-30.
Johansson, "A review of the pharmacokinetics and pharmacodynamics of disulfiram and its metabolites," Acta psychiatrica Scandinavica. Supplementum, 1992, 369:15-26.
King et al., "A Novel, Species-specific Class of Uncompetitive Inhibitors of γ-Glutamyl Transpeptidase," Journal of Biological Chemistry, 2009, 284(14):9059-9065.
Koppaka et al., "Aldehyde dehydrogenase inhibitors: a comprehensive review of the pharmacology, mechanism of action, substrate specificity, and clinical application," Pharmacological Reviews, 2012, 64(3):520-539.
Kularatne et al., "Synthesis and biological analysis of prostate-specific membrane antigen-targeted anticancer prodrugs," Journal of Medicinal Chemistry 2010, 53(21):7767-7777.
Kumar et al., "Malignant Catatonia and Neuroleptic Malignant Syndrome in Relation to Disulfiram Overdose," Journal of Psychological Medicine, 2016, 38(4):344-347.
Lewis et al., "On the interaction of copper(II) with disulfiram," Chemical Communications, 2014, 50(87):13334-13337.
Lu et al., "Synthesis and SAR of novel Re/99mTc-labeled benzenesulfonamide carbonic anhydrase IX inhibitors for molecular imaging of tumor hypoxia," Journal of Medicinal Chemistry, 2013, 56(2):510-520.
Luo et al., "Activatable Near-Infrared Probe for Fluorescence Imaging of γ-Glutamyl Transpeptidase in Tumor Cells and in Vivo," Chemistry—A European Journal, 2017, 23(59):14778-14785.
Maurer et al., "Current use of PSMA-PET in prostate cancer management," Nature reviews. Urology, 2016, 13(4):226-235.
McCutcheon's vol. 1, Emulsifiers & Detergents, 1994, North American Edition, pp. 236-239.

Miyata et al., "Intraoperative imaging of hepatic cancers using γ-glutamyltranspeptidase-specific fluorophore enabling real-time identification and estimation of recurrence," Scientific Reports, 2017, 7, 3542.
Mohapatra et al., "Disulfiram-induced neuropathy: a case report," General Hospital Psychiatry, 2015, 37(1):97.e5-97.e6.
Morrison et al., "Disulfiram induces copper-dependent stimulation of reactive oxygen species and activation of the extrinsic apoptotic pathway in melanoma," Melanoma Research, 2010, 20(1):11-20.
Peng et al., "PET of human prostate cancer xenografts in mice with increased uptake of $^{64}CuCl_2$," Journal of Nuclear Medicine, 2006, 47(10):1649-1652.
Piccardo et al., "$^{64}CuCl_2$ PET/CT in Prostate Cancer Relapse," Journal of Nuclear Medicine, 2018, 59(3):444-451.
Pujol et al., "A Sulfur Tripod Glycoconjugate that Releases a High-Affinity Copper Chelator in Hepatocytes," Angewandte Chemie International Edition, 2012, 51(30):7445-7448.
Ramsay et al., "Glutathione S-conjugates as prodrugs to target drug-resistant tumors," Frontiers in Pharmacology, 2014, vol. 5, Article 181, 16 pages.
Remington's Pharmaceutical Sciences, 15th Ed., 1975, pp. 335-337.
Safi et al., "Copper signaling axis as a target for prostate cancer therapeutics," Cancer Research, 2014, 74(20):5819-5831.
Scher et al., "Increased Survival with Enzalutamide in Prostate Cancer after Chemotherapy," The New England Journal of Medicine, 2012, 367:1187-1197.
Schweizer et al., "Pharmacodynamic study of Disulfiram in Men with Non-metastatic Recurrent Prostate Cancer," Prostate Cancer and Prostatic Diseases, 2013, 16(4):357-361.
Siegel et al., "Cancer statistics, 2015," CA: A Cancer Journal for Clinicians, 2015, 65(1):5-29.
Skrott et al., "Alcohol-abuse drug disulfiram targets cancer via p97 segregase adaptor NPL4," Nature, 2017, 552(7684):194-199.
Tardito et al., "Copper Compounds in Anticancer Strategies," Current Medicinal Chemistry, 2009, 16(11):1325-1348.
Tawari et al., "The cytotoxic mechanisms of disulfiram and copper(II) in cancer cells," Toxicology Research, 2015, 4(6):1439-1442.
Tisato et al., "Copper in diseases and treatments, and copper-based anticancer strategies," Medicinal Research Reviews, 2010, 30(4):708-749.
Tran et al., "Disulfiram neuropathy: two case reports," Journal of Medical Case Reports, 2016, 10, Article 72.
Vlahov et al., "Engineering folate-drug conjugates to target cancer: from chemistry to clinic," Bioconjugate Chemistry, 2012, 23(7):1357-1369.
Wang et al., "Poly lactic-co-glycolic acid controlled delivery of disulfiram to target liver cancer stem-like cells," Nanomedicine: Nanotechnology, Biology and Medicine, 2017, 13(2):641-657.
Wang et al., "Stimulus-Responsive Prochelators for Manipulating Cellular Metals," Accounts of Chemical Research, 2016, 49(11):2468-2477.
Wehbe et al., "A Perspective—can copper complexes be developed as a novel class of therapeutics?" Dalton Transactions, 2017, 46(33):10758-10773.
Wiggins et al., "Disulfiram-induced cytotoxicity and endo-lysosomal sequestration of zinc in breast cancer cells," Biochemical Pharmacology, 2015, 93(3):332-342.
Wu et al., "Design and Synthesis of Peptide Conjugates of Phosphoramide Mustard as Prodrugs Activated by Prostate-Specific antigens," Bioorganic and Medicinal Chemistry, 2016, vol. 24, pp. 2697-2706. p. 2697, col. 2, para. 2; p. 2699, Scheme 2, Compound 1; Scheme 4, Compound Ba (10 pages).
Zaengle-Barone et al., "Copper Influences the Antibacterial Outcomes of a β-Lactamase-Activated Prochelator against Drug-Resistant Bacteria," ACS Infectious Diseases, 2018, 4(6):1019-1029.
International Search Report and Written Opinion for Application No. PCT/US2018/040801 dated Sep. 20, 2018 (10 pages).
International Search Report and Written Opinion, PCT/US2018/040801, dated Sep. 20, 2018 (6 pages).

* cited by examiner

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: SSTT

<400> SEQUENCE: 1

Ser Ser Tyr Tyr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Ser Ser Phe Tyr
1

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Ser Ser Tyr Tyr Ser
1               5

<210> SEQ ID NO 4
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 4

Ser Ser Phe Tyr Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Ser Ser Tyr Tyr Ser Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Arg Ser Ser Tyr Tyr Ser Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Sythetic

<400> SEQUENCE: 7

Arg Ser Ser Tyr Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

His Ser Ser Lys Leu Gln
1               5
```

PROCHELATORS AS TARGETED PRODRUGS FOR PROSTATE CANCER AND METHODS OF MAKING AND USING SAME

CROSS-REFERENCE TO RELATED APPLICATIONS

This patent application is the U.S. national stage entry, under 35 U.S.C. §371, of International Application Number PCT/US2018/040801, filed Jul. 3, 2018, which claims the benefit of and priority to U.S. Provisional Patent Application No. 62/528,591, filed on Jul. 5, 2017, the entire contents of each of which are hereby incorporated herein by reference.

STATEMENT OF GOVERNMENT SUPPORT

This invention was made with government support under Grant Number CHE-1152054 awarded by the National Science Foundation and Grant Number CA014236 awarded by the National Institutes of Health. The government has certain rights in the invention.

SEQUENCE LISTING

The instant application includes a Sequence Listing which has been submitted electronically in ASCII format and is hereby incorporated by reference in its entirety. Said ASCII copy, created on Dec. 27, 2019, is named 028193-9303-US02_As_Filed_Sequence_Listing.txt and is 1,546 bytes in size.

FIELD

The present disclosure relates to compounds as prodrugs for treating prostate cancer, methods of making thereof, and method of using the same.

BACKGROUND

Metastatic castration resistant prostate cancer (mCRPC) is aggressive and often lethal. Although hormonal agents and chemotherapies targeting androgen receptors have improved treatment, there is a clear need to develop prostate cancer therapies that act on targets other than androgen receptors. An exciting and under-developed possibility is to target aspects of biological copper regulation that are linked to disease. Clinical observations that circulating and intratumoral copper levels are elevated in prostate cancer patients inspired a team of Duke researchers to define the mechanisms of Cu uptake in prostate cancer cells and discover molecules that are cytotoxic under such Cu-loaded conditions. That preclinical effort uncovered disulfiram, an FDA-approved drug used since 1948 for alcohol-aversion therapy. However, significant hurdles hinder the possibility that disulfiram itself will be an effective cancer treatment—a phase 1 study of disulfiram in mCRPC patients demonstrated significant toxicity without improvement in efficacy. Indeed, 6 of the 12 patients developed grade 3 adverse events including double vision, hearing loss, increase in liver function testing, ataxia, and diarrhea.

Although Cu has long been recognized as a factor in cancer cell proliferation, approaches to date have not optimally exploited this aspect for clinical effect. A challenge in this area is to discover ways to reallocate Cu selectively to the tumor or pre-tumor site without systemically altering healthy metal status. A clinical trial protocol has already been designed, which tests copper and disulfiram in patients with metastatic CPRC, with an FDA-approved IND. Disulfiram itself has clinical issues, however, that will require innovative solutions to maximize their potential benefit. For its approved use to curb alcohol consumption, disulfiram (DSF, FIG. 1) is itself a prodrug. Upon entering a cell, the disulfide form is readily reduced to a dithiocarbamate (DTC, FIG. 1), which can then react with protein thiols to form mixed disulfide protein adducts. Further metabolism in the liver leads to diethylthiocarbamate-sulfoxide and sulfone metabolites that ultimately inhibit aldehyde dehydrogenase, the desired target for causing an aversive build-up of acetaldehyde in patients who consume ethanol. These reactions and metabolites are counterproductive in terms of cancer therapy. Over the last 2 decades, a significant amount of research has shown that the active anti-cancer agent is the Cu complex of DTC.

Therefore, there remain a need for prodrug compounds that enable targeted delivery of DTC or its equivalents to cancer cells (in particular prostate cancer cells) with reduced toxicity or other side effects and/or improved efficacy in cancer therapy.

SUMMARY

The present disclosure addresses the problems of the previous studies by providing novel targeted dithiocarbamate compounds and compositions that leverage the conditional copper biology of prostate cancer, while potentially minimizing the multitude of side reactions and off-target pathways that impede disulfiram's anticancer potential. This innovation as disclosed herein is significant because it enables the development of novel agents that leverage a unique, untapped feature of prostate cancer to tackle the most aggressive, treatment-resistant cases for which there are currently no good options.

The present disclosure provides compounds, compositions, and methods for the treatment of cancer, such as prostate cancer.

One aspect of the present disclosure provides a composition for the treatment of prostate cancer, the composition comprising, consisting of, or consisting essentially of a dithiocarbamate prodrug and any salts, esters, and derivatives thereof.

In one aspect, disclosed is a dithiocarbamate prodrug compound of formula (I):

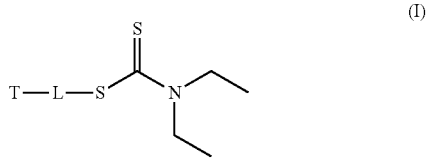

or a pharmaceutically accept salt, amide, or ester thereof, wherein
T is a targeting moiety for a cell; and
L is a linker.
In some embodiments, T is a substrate of an enzyme of a cell. In some embodiments, T binds to a protein of the cell.
In one embodiment, the dithiocarbamate prodrug comprises, consists of, or consists essentially of the prostate specific antigen activated prodrug PSA-DTC having the formula:

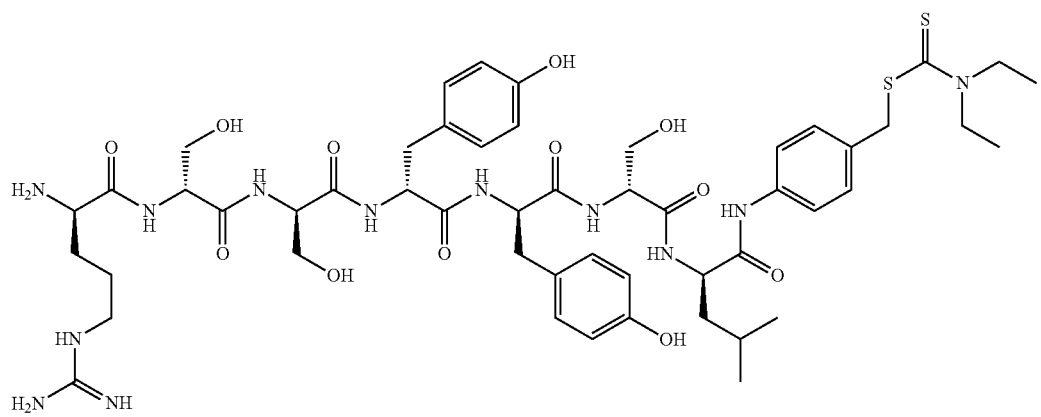 [SMILES: CCN(CC)C(=S)SCc1ccc(NC(=O)[C@@H](CC(C)C)NC(=O)[C@@H](CO)NC(=O)[C@@H](Cc2ccc(O)cc2)NC(=O)[C@@H](Cc2ccc(O)cc2)NC(=O)[C@@H](CO)NC(=O)[C@@H](CO)NC(=O)[C@H](N)CCCNC(=N)N)cc1]

and any salts, esters, and derivatives thereof.

In another embodiment, the dithiocarbamate prodrug comprises, consists of, or consists essentially of the γ-glutamyl transferase activated prodrug Glu-DTC having the formula:

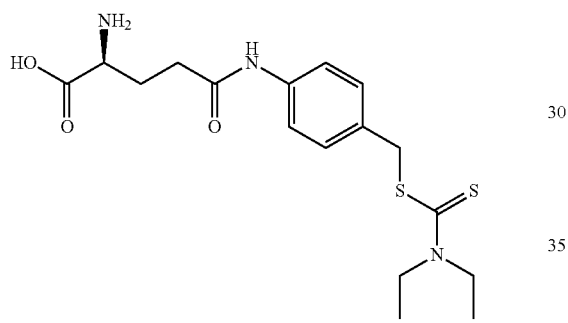

and any salts, esters, and derivatives thereof.

In another embodiment, the dithiocarbamate prodrug comprises, consists of, or consists essentially of the folic acid conjugated prodrug FA-DTC having the formula:

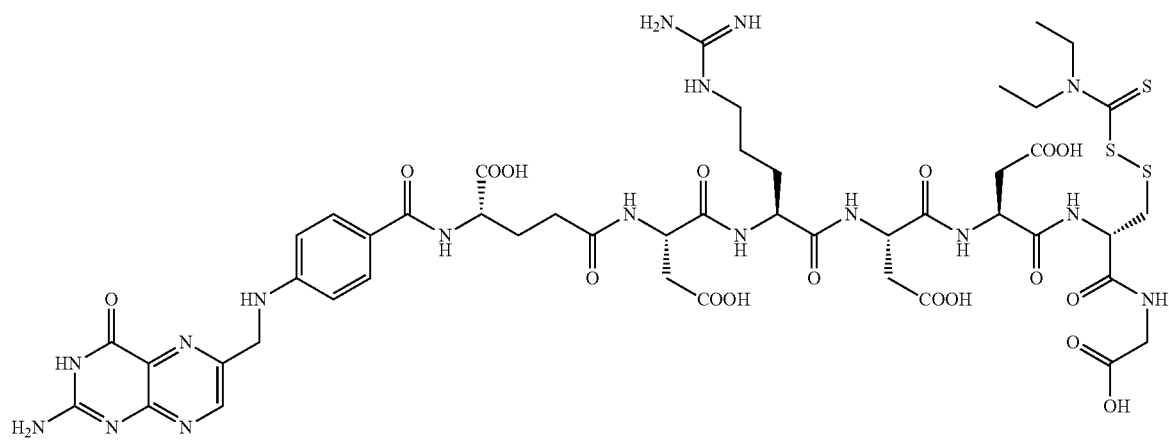 [SMILES: CCN(CC)C(=S)SSC[C@@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c1ccc(NCc2cnc3nc(N)[nH]c(=O)c3n2)cc1)C(=O)O)C(=O)NCC(=O)O]

and any salts, esters, and derivatives thereof.

In another embodiment, the dithiocarbamate prodrug comprises, consists of, or consists essentially of the prostate specific membrane antigen targeting prodrug PSMA-DTC having the formula:

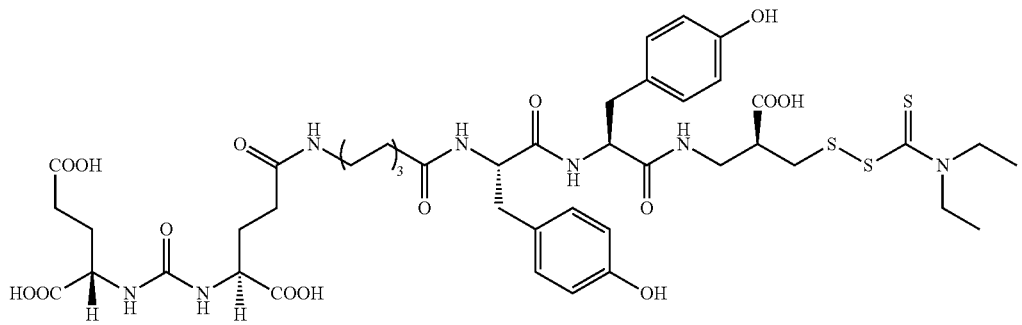

and any salts, esters, and derivatives thereof.

Another aspect of the present disclosure provides a method of treating a subject suffering from cancer comprising, consisting of, or consisting essentially of administering to the subject a therapeutically effective amount of a dithiocarbamate prodrug as described herein such that the cancer is treated.

Another aspect of the present disclosure provides a method of preventing cancer in a subject comprising, consisting of, or consisting essentially of administering to the subject a therapeutically effective amount of a dithiocarbamate prodrug as described herein such that the cancer is prevented.

Another aspect of the present disclosure provides a method of attenuating a cancer in a subject comprising, consisting of, or consisting essentially of administering to the subject a therapeutically effective amount of a dithiocarbamate prodrug as described herein such that the cancer is attenuated.

In some embodiments, the cancer comprises prostate cancer.

In other embodiments, the method(s) further comprises co-administering to the subject an additional anticancer therapy selected from the group consisting of radiation, chemotherapy, immunotherapy, targeted therapy, hormone therapy, surgery, stem cell transplants, precision medicine and combinations thereof. In some embodiments, the additional anticancer therapy is administered prior to the administration of the dithiocarbamate prodrug. In another embodiment, the additional anticancer therapy is administered concurrently with the administration of the dithiocarbamate prodrug. In yet another embodiment, the additional anticancer therapy is administered after the administration of the dithiocarbamate prodrug.

Another embodiment of the present disclosure provides for a kit for the treatment of a cancer comprising, consisting of, or consisting essentially of a dithiocarbamate prodrug as provided here, instruments for the administration of the dithiocarbamate prodrug, and instructions for use.

The present disclosure further provides for methods of making the dithiocarbamate prodrugs provided herein.

Yet another aspect of the present disclosure provides all that is disclosed and illustrated herein.

BRIEF DESCRIPTION OF THE DRAWINGS

The foregoing aspects and other features of the disclosure are explained in the following description, taken in connection with the accompanying drawings, herein.

Figure 1:
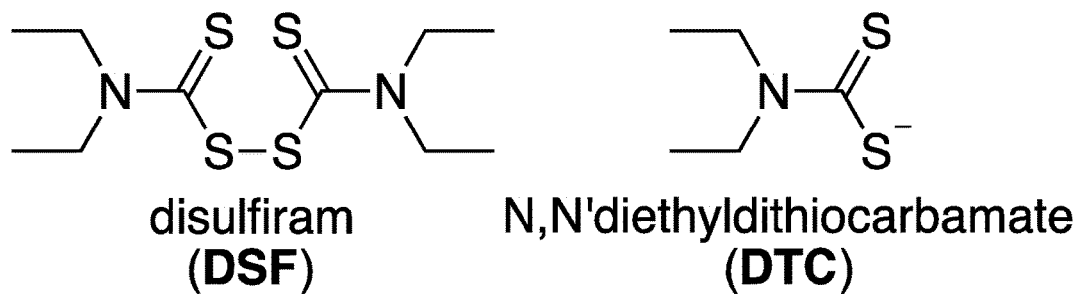
FIG. 1 shows the chemical structures of Disulfiram (DSF), and its active component (DTC).

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

1. Definitions

The use of "including," "comprising," "having" and variations thereof, as used herein, are meant to encompass the items listed thereafter and equivalents thereof as well as additional items. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Articles "a" and "an" are used herein to refer to one or to more than one (i.e. at least one) of the grammatical object of the article. By way of example, "an element" means at least one element and can include more than one element. As used in this specification and the appended claims, the term "or" is generally employed in its sense including "and/or" unless the context clearly dictates otherwise.

Unless otherwise defined, all technical terms used herein have the same meaning as commonly understood by one of ordinary skill in the art to which this disclosure belongs.

"Amino acid" as used herein refers to the complete or partial (or residue) structures of naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. In particular, the term "amino acid" as used herein to represent a moiety of a compound may refer to a structure of formula (AA-1)

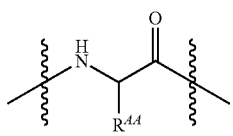

(AA-1)

wherein $R^{AA}$ is H or a side chain of a natural or synthetic amino acid molecule.

A "linker moiety" is adapted for connecting a partial structure (such as a dithiocarbamate group) to the remaining part of a molecule in the various embodiments of the invention. As used herein, the term "attach" refers to any manner of association between two or more molecules, or between two or more partial structures, to form a single entity, including covalent bonding, complexation, chelation, ion-pairing, and the like.

The term "peptide" as used herein refers to the complete or partial (or residue) structure of a sequence of two or more, but no greater than approximately 50, amino acids linked by peptide bonds. In some embodiments, the peptide is between 2 and 10 amino acids long. The peptide can be natural, synthetic, or a modification or combination of natural and synthetic. The peptide may be modified by the addition of sugars, lipids or other moieties not included in the amino acid chain. All peptides except cyclic peptides have an N-terminal and C-terminal residue at the end of the peptide, generally amino acids in a peptide chain are listed N-terminus to C-terminus, unless otherwise indicated. Amino acids that have been incorporated into peptides are termed "residues" due to the release of either a hydrogen ion from the amine end or a hydroxyl ion (OH⁻) from the carboxyl (COOH) end, or both, as a water molecule is released during formation of each amide bond. In particular, the term "peptide" as used herein to represent a moiety of a compound may refer to a structure of formula (AA-2)

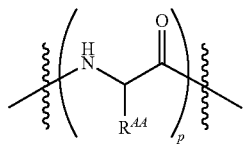

(AA-2)

wherein $R^{AA}$ is H or a side chain of a natural or synthetic amino acid molecule, and p is 2-50. In some embodiments, p is 2-20, 2-10, or 2-8. In some embodiments, p is 2, 3, 4, 5, or 6. Exemplary peptides include Ser-Ser-Tyr-Tyr (SEQ ID NO:1), Ser-Ser-Phe-Tyr (SEQ ID NO:2), Ser-Ser-Tyr-Tyr-Ser (SEQ ID NO:3), Ser-Ser-Phe-Tyr-Ser (SEQ ID NO:4), Ser-Ser-Tyr-Tyr-Ser-Leu (SEQ ID NO:5), or Arg-Ser-Ser-Tyr-Tyr-Ser-Leu (SEQ ID NO:6), Arg-Ser-Ser-Tyr-Tyr (SEQ ID NO:7), His-Ser-Ser-Lys-Leu-Gln (SEQ ID NO:8), and Ser-Leu.

A "prodrug" is a derivative of a known drug or therapeutic, which when administered to a subject, may be converted in to an active form. The conversion may be due to enzymatic and/or chemical hydrolytic cleavage of the prodrug and may occur in such a manner that the known drug form is released, and the moiety or moieties split off remain nontoxic or are metabolized. In some embodiments, the prodrug may be activated by enzymatic cleavage by γ-glutamyl transferase (GGT) GGT and/or Prostate Specific Antigen (PSA). In some embodiments the prodrug may contain a targeting moiety which directs the prodrug to a specific location within the subject. In some embodiments the targeting moiety may facilitate an interaction with a receptor found in discrete locations or to discrete cell types within a subject; such as the Folate Receptor or Prostate Specific membrane Antigen (PSMA). In some embodiments the targeting moiety may also include the site for enzymatic and/or chemical hydrolytic cleavage of the prodrug.

As used herein, the term "dithiocarbamate" refers to an analog of carbamate in which both oxygen atoms are replaced by sulfur atoms. In particular, dithiocarbamate compounds may refer to N,N'-dietheyldithiocarbamate compounds (FIG. 1).

For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

If substituents are described as being "independently" selected from a group, each substituent is selected independent of the other. Each substituent, therefore, may be identical to or different from the other substituent(s).

2. Compounds

Prostate cancer is the most common cancer among men. While androgen deprivation therapy can be effective at initial stages, there are many cases where disease continues to progress despite therapy and becomes metastatic. Metastatic castration resistant prostate cancer (mCRPC) is often lethal. Although chemotherapies have improved treatment, off-target activities of these drugs have necessitated the search for novel and selective drugs for mCRPC. The metallobiology of mCRPC offers a unique avenue for targeting prostate cancer cells because they differ from normal cells by having higher levels of copper-trafficking proteins and hence relatively high levels of copper ions. The present disclosure provides compounds or compositions (e.g. drugs or prodrugs) that may manipulate the copper biology of these cells thereby providing a potent therapeutic for mCRPC. The compounds or compositions provided herein may be further activated only in mCRPC tissue thereby eluding off-target activity and side reactions.

Accordingly, one aspect of the present disclosure provides a compound or a composition for the treatment of prostate cancer, the composition comprising, consisting of, or consisting essentially of a dithiocarbamate prodrug and any salts, esters, and derivatives thereof.

In one aspect, disclosed is a compound of formula (I):

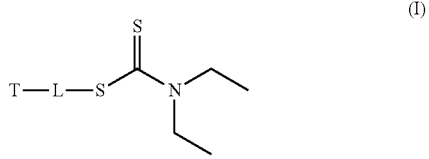

(I)

or a pharmaceutically accept salt, amide, or ester thereof, wherein

T is a targeting moiety for a cell; and

L is a linker.

In general, T may be a moiety that targets or recognize a cell. As described herein, the capability of a compound or a structural moiety of a compound to target or recognize a cell refers to the property of the compound or moiety to specifically interact with a component (e.g. a protein) of the cell. For example, the compound or moiety may be a substrate of an enzyme of the cell, or a ligand that binds to a receptor, a transporter, a signaling protein, or other functional proteins of the cell. As a result, the compound may have a higher affinity to the cells that are targeted or recognized by the compound, as compared to the untargeted or unrecognized cells (e.g. cells that do not contain the enzyme or the functional protein specifically interacting with the compound). In some embodiments, the cell is a cancer cell, such as a prostate cancer cell.

In some embodiments, T is a substrate of an enzyme of a cell, such as a cancer cell. In some embodiments, T is a substrate of a protease of a cancer cell, such as a prostate cancer cell. In some embodiments, T binds to a protein of a cell, such as a cancer cell. In some embodiments, T binds to a transporter of a cancer cell, such as a prostate cancer cell.

In some embodiments, T is an amino acid or a peptide. In some embodiments, T is a peptide, which is a substrate of a protease. For example, T may be a peptide having 2-10 amino acids, which may be cleaved by a protease. In some embodiments, T is a peptide, which is a substrate of Prostate Specific Antigen (PSA). Examples of peptides that are substrates of PSA include, but are not limited to, the peptides disclosed in Coombs et al. (Chemistry and Biology, 1998, 5:475-488), Denmeade et al. (Cancer Research, 1997, 57, 4924-4930), and Denmeade et al. (Journal of the National Cancer Institute, Vol. 95, No. 13, 990-1000), the contents of which are incorporated herein by reference in their entirety.

In some embodiments, T is peptide that includes a Ser-Ser-Tyr-Tyr (SEQ ID NO:1), Ser-Ser-Phe-Tyr (SEQ ID NO:2), Ser-Ser-Tyr-Tyr-Ser (SEQ ID NO:3), Ser-Ser-Phe-Tyr-Ser (SEQ ID NO:4), Ser-Ser-Tyr-Tyr-Ser-Leu (SEQ ID NO:5), Arg-Ser-Ser-Tyr-Tyr-Ser-Leu (SEQ ID NO:6), Arg-Ser-Ser-Tyr-Tyr (SEQ ID NO:7), or His-Ser-Ser-Lys-Leu-Gln (SEQ ID NO:8) sequence of amino acids. In a particular embodiments, T is

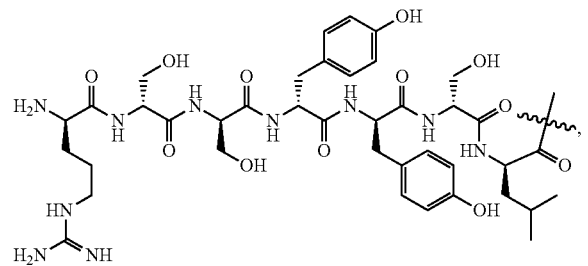 [SMILES: *C(=O)[C@@H](CC(C)C)NC(=O)[C@@H](CO)NC(=O)[C@@H](Cc1ccc(O)cc1)NC(=O)[C@@H](Cc1ccc(O)cc1)NC(=O)[C@@H](CO)NC(=O)[C@@H](CO)NC(=O)[C@H](N)CCCNC(=N)N]

which may be cleaved by a protease, such as PSA.

In some embodiments, T is a substrate that may be hydrolyzed by a cellular enzyme, such as γ-glutamyl transferase. In a particular embodiment, T is an amino acid (such as a glutamic acid), which may be hydrolyzed by a cellular enzyme (such as γ-glutamyl transferase). For example, T is glutamic acid attached to the remaining part of the compound through the carboxylic acid group on the side chain, having a structure of

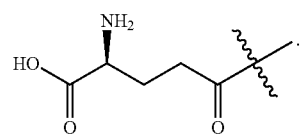 [SMILES: *C(=O)CC[C@H](N)C(=O)O]

In some embodiments, T is a moiety derived from a compound that binds to a receptor, a transporter, a signaling protein, or other functional proteins of a cell. In a particular embodiment, T is a moiety derived from folic acid or analogues thereof. In a particular embodiment, T is

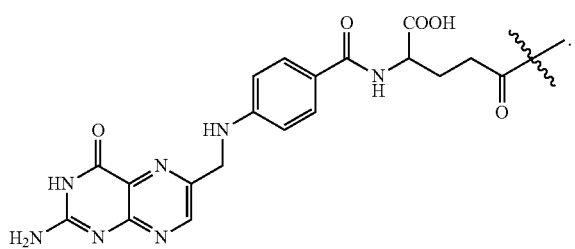 [SMILES: *C(=O)CCC(NC(=O)c1ccc(NCc2cnc3nc(N)[nH]c(=O)c3n2)cc1)C(=O)O]

For example, T may have a structure of

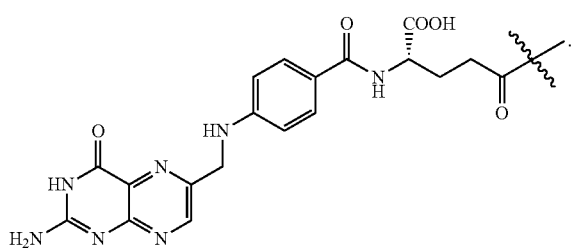 [SMILES: *C(=O)CC[C@H](NC(=O)c1ccc(NCc2cnc3nc(N)[nH]c(=O)c3n2)cc1)C(=O)O]

In another embodiment, T is a moiety derived from a compound that binds to a membrane-bound protein, such as 2-[3-(1,3-dicarboxypropyl)ureido] pentanedioic acid (DUPA), having a structure of

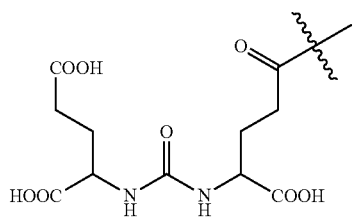

For example, T may have a structure of

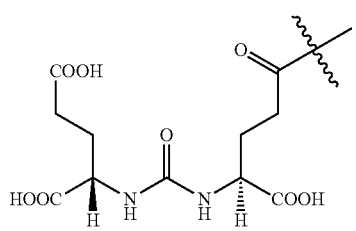

L is a linker between the cell targeting moiety (T) and the diethyldithiocarbamate (DTC) moiety,

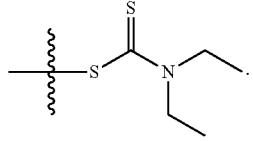 [SMILES: *SC(=S)N(CC)CC]

In some embodiments, L is a self-immolative moiety. In some embodiments, L is attached to the DTC moiety through a disulfide bond (—S—S—).

In some embodiments, L is

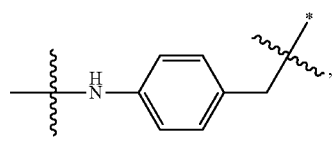

W, or —NH(CH$_2$)$_n$—C(O)—W; wherein W is

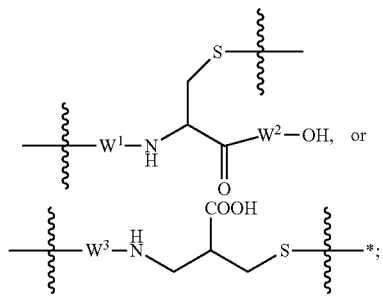

* indicates the attachment to

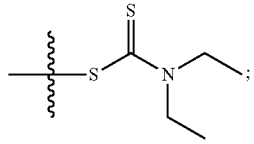

W$^1$, W$^2$, and W$^3$ are each independently a bond, an amino acid, or a peptide; and n is 1, 2, 3, 4, 5, 6, 7, 8, 9, or 10.

In some embodiments, n is 4, 5, 6, 7, or 8. In some embodiments, n is 4, 6, or 8. In some embodiments, n is 6.

In some embodiments, L is a self-immolative moiety, such as

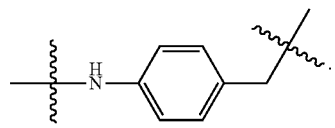 [SMILES: *Cc1ccc(N*)cc1]

In some embodiments, L is W or —NH(CH$_2$)$_n$—C(O)—W, wherein W is

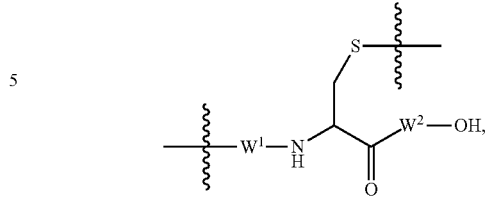

W$^1$ and W$^2$ are each independently a bond, an amino acid, or a peptide. For example, W$^1$ and W$^2$ each independently may be a bond, an amino acid, or a peptide having 2-8 amino acids. In some embodiments, W$^1$ is an amino acid, or a peptide having 2-8 amino acids, and W$^2$ is a bond or an amino acid.

In some embodiments, L is W or —NH(CH$_2$)$_n$C(O)—W, wherein W is

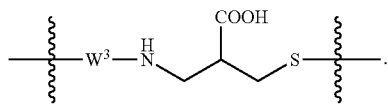

In some embodiments, W$^3$ is an amino acid or a peptide. For example, W$^3$ may be an amino acid or a peptide having 2, 3, 4, 5, 6, 7, or 8 amino acids.

In some embodiments, L is

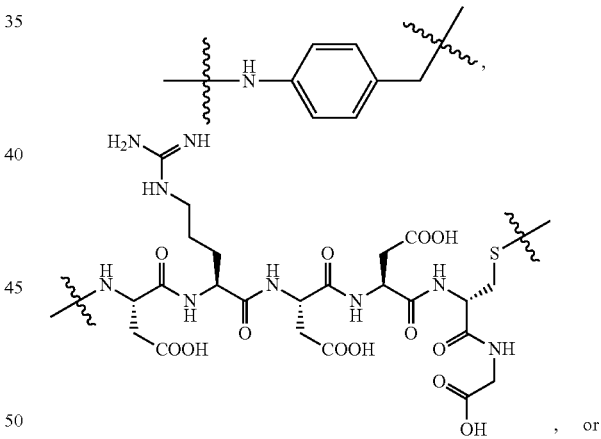

, or

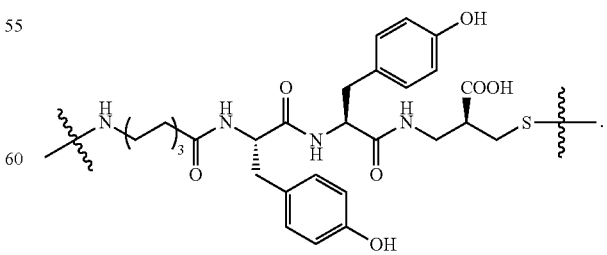

In some embodiments, T is an amino acid or a peptide having 2-10 amino acids, and L is

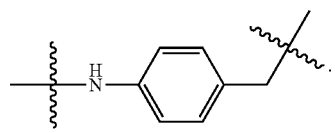 [SMILES: *Cc1ccc(N*)cc1]

In some embodiments, T is a moiety derived from folic acid or analogues thereof, such as

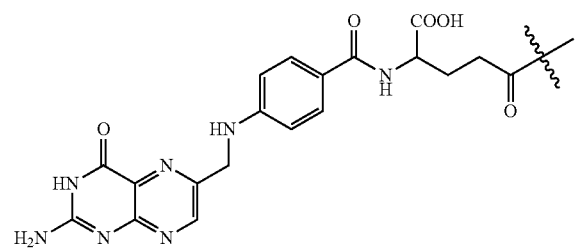

or a moiety derived from a compound that binds to a membrane-bound protein, such as

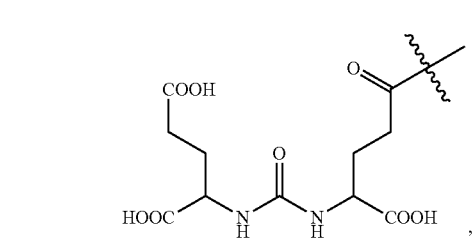 [SMILES: *C(=O)CCC(NC(=O)NC(CCC(=O)O)C(=O)O)C(=O)O]

and L is W or —NH(CH$_2$)$_n$C(O)—W.

In some embodiments, T is a moiety derived from folic acid or analogues thereof, such as

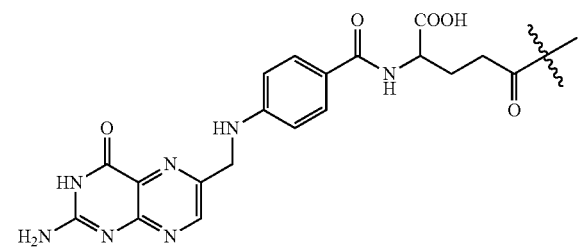 [SMILES: *C(=O)CCC(NC(=O)c1ccc(NCc2cnc3nc(N)[nH]c(=O)c3n2)cc1)C(=O)O]

and L is W. For example, in such compounds, W may be

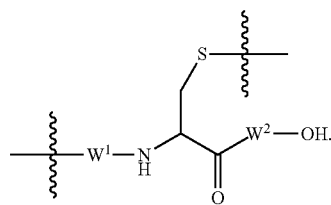

In a particular embodiment, T is

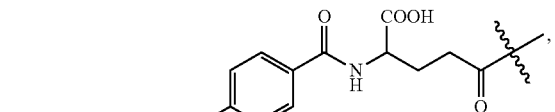

L is W, W is

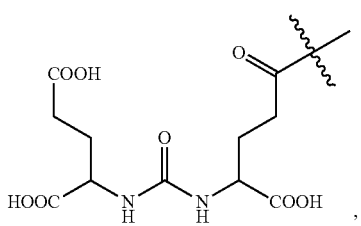 [SMILES: *C(=O)CCC(NC(=O)NC(CCC(=O)O)C(=O)O)C(=O)O]

and W$^1$ and W$^2$ are each independently a bond, an amino acid, or a peptide having 2-8 amino acids. For example, in such compounds, W$^1$ and W$^2$ each independently may be an amino acid or a peptide having 2-8 amino acids. Alternatively, in such compounds, W$^1$ may be an amino acid or a peptide having 2-8 amino acids, and W$^2$ may be a bond or an amino acid.

In some embodiments, T is a moiety derived from a compound that binds to a membrane-bound protein, such as

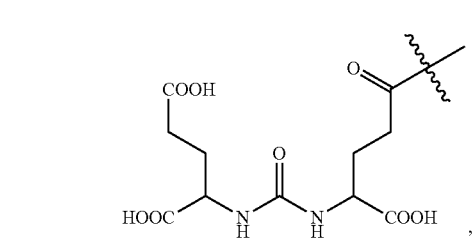 [SMILES: *C(=O)CCC(NC(=O)NC(CCC(=O)O)C(=O)O)C(=O)O]

and L is —NH(CH$_2$)$_n$C(O)—W. For example, in such compounds, W may be

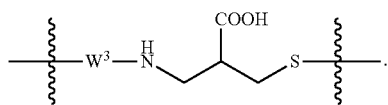

In a particular embodiment, T is
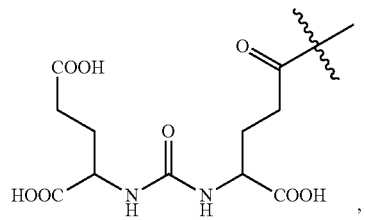 [SMILES: *C(=O)CCC(NC(=O)NC(CCC(=O)O)C(=O)O)C(=O)O]
L is —NH(CH$_2$)$_n$—C(O)—W, W is
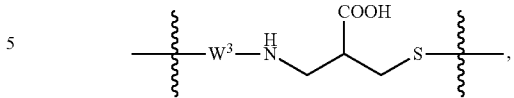
and W$^3$ is an amino acid or a peptide having 2-6 amino acids. For example, in such compounds, W3 may be a peptide having 2, 3, or 4 amino acids.
Representative compounds of formula (I) include, but are not limited to:
(PSA-DTC)
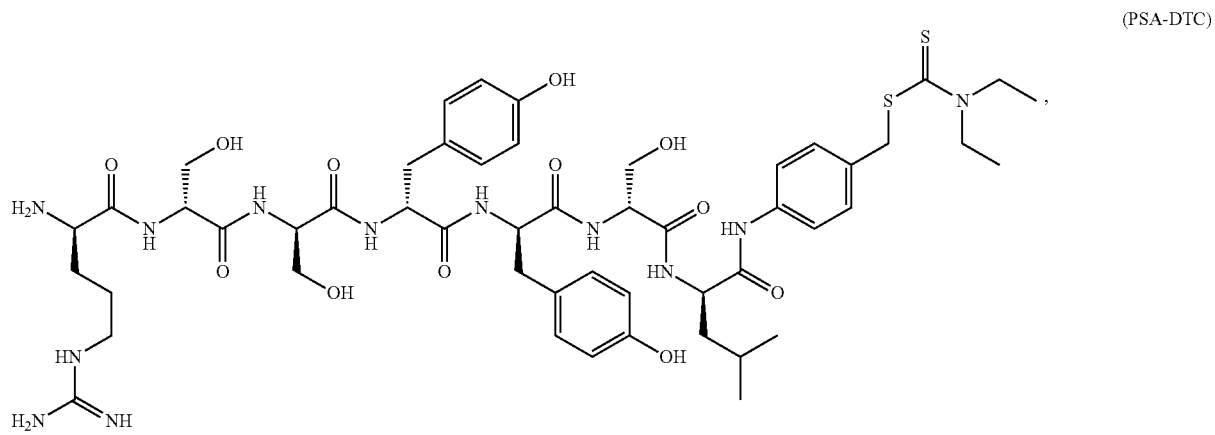
(Glu-DTC)
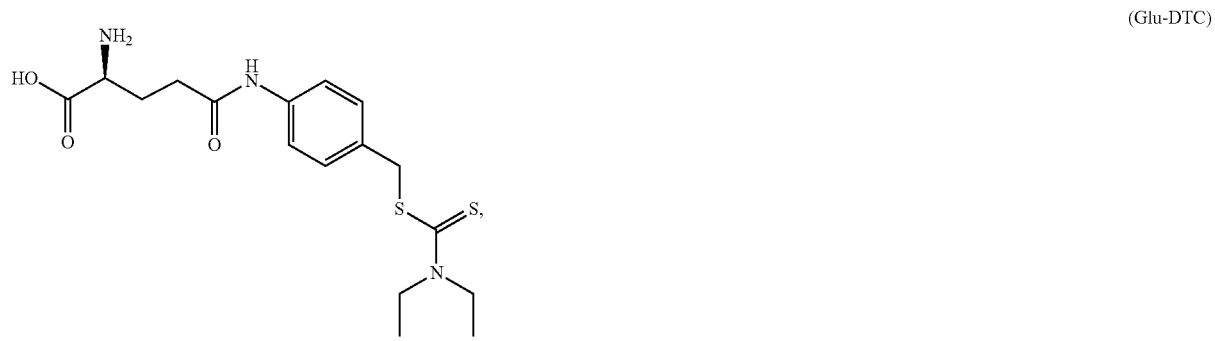
(FA-DTC)
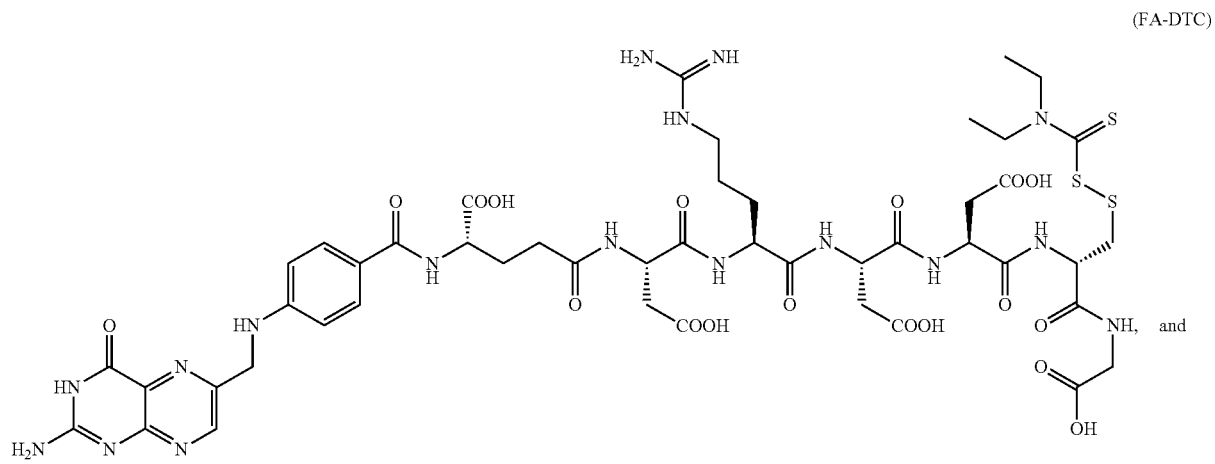
and

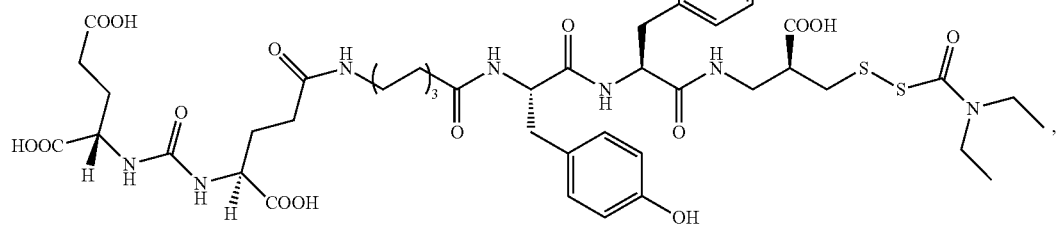

(PSMA-DTC)

or a pharmaceutically accept salt, amide, or ester thereof

Representative Classes of Compounds

The disclosed compound may function as dithiocarbamate prodrugs. In some embodiments, the disclosed compounds may be divided into two representative classes: enzyme activated dithiocarbamate prodrugs and receptor targeting dithiocarbamate prodrugs.

Class 1: Enzyme Activated Dithiocarbamate Prodrugs

In some embodiments, a dithiocarbamate (DTC) moiety is conjugated to an enzyme targeting peptide or amino acid via a linker, such as self-immolative linker. The enzyme cleaves the substrate to release the DTC. By targeting specific enzymes overexpressed in cancer cells (such as prostate cancer) the DTC could be selectively released in cancer tissue.

A. Prostate Specific Antigen (PSA) Activated Prodrug (PSA-DTC)

Figure 2:
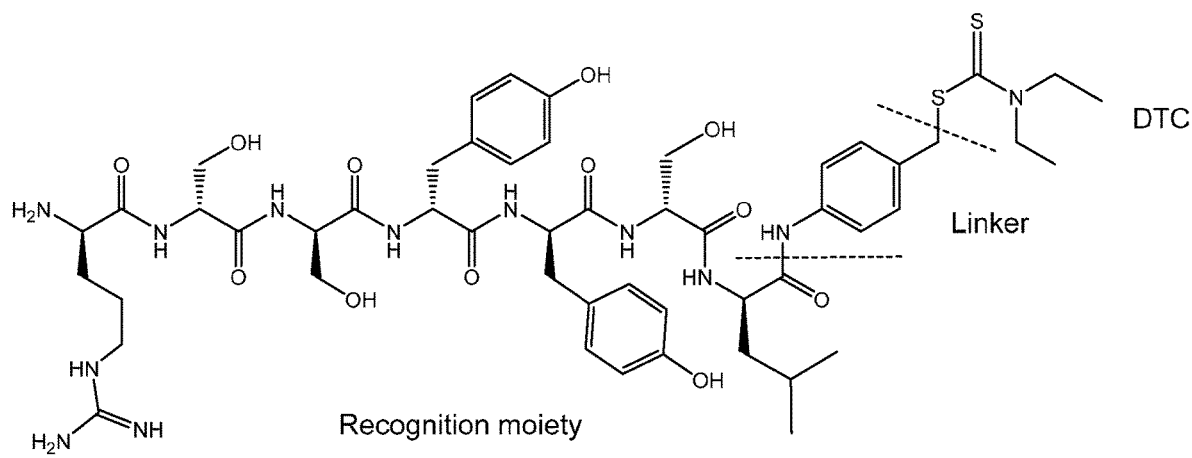
FIG. 2 shows the chemical structure of PSA-DTC, including: the Recognition moiety—PSA cleavable peptide; the Linker—PAB and the Chelator—diethyldithiocarbamate (DTC). Arg-Ser-Ser-Tyr-Tyr-Ser-Leu (SEQ ID. No. 6) is one example of peptide substrate. Other dithiocarbamates in addition to DTC are also possible in accordance with one embodiment of the present disclosure.

In some embodiments, the dithiocarbamate prodrug comprises, consists of, or consists essentially of the prostate specific antigen activated prodrug PSA-DTC having the formula as showing in FIG. 2 and any salts, esters, and derivatives thereof. In some embodiments, disclosed are representative compounds that include a Prostate Specific Antigen (PSA) targeting or recognizing moiety, such as the compound shown in FIG. 2, or a pharmaceutically accept salt, amide, or ester thereof.

In some embodiments, the disclosed compounds leverage the overexpression and excretion of a protease, Prostate Specific Antigen (PSA), by prostate cancer cells to conditionally release the active and Cu-binding form of DTC preferentially in the prostate tumor microenvironment. PSA is a clinical biomarker for prostate cancer. PSA-induced drug release has been successful in pre-clinical models for several cytotoxic agents, including vinblastine, thapsigargin, and doxorubicin, the latter having passed a Phase I trial. The PSA target molecule may contain, for example, Arg-Ser-Ser-Tyr-Tyr-Ser-Leu (SEQ ID NO:6), as shown in the literature for PSA-selective release of doxorubicin. In some embodiments, a p-aminobenzyl linker (PAB) is used as it has been reported to self-immolate upon release of conjugated by peptide. PAB is generally employed with an oxygen-containing nucleophile. As disclosed herein, PAB may be used to mask the thiol group of DTC. Without being limited by any theory, it is hypothesized that PSA may initially hydrolyze the Tyr-Ser bond in the peptide, with non-specific cellular proteases trimming the final two residues to initiate the 1,6 benzyl elimination of the self-immolative PAB linker to release the DTC cargo.

B. γ-Glutamyl Transferase (GGT) Activated Prodrug (Glu-DTC)

Figure 3:
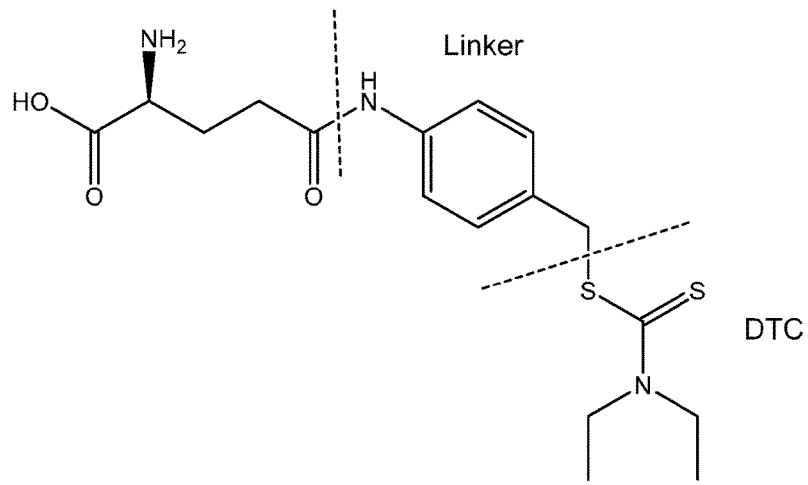
FIG. 3 shows the chemical structure of Glu-DTC, including: the Recognition moiety—γ-Glutamate; the Linker—PAB; the Chelator—DTC.

GGT is an enzyme that is present in the cell membrane and is involved in the metabolism of glutathione. GGT has been reported to be overexpressed in cancer tissues especially in cis-platin resistant strains. GGT is involved in glutathione (GSH) metabolism to Cys-Gly dipeptide which protects the cells from oxidative stress. While GGT has been targeted with GGT antibodies and by modifying cysteinyl thiol of GSH, γ-Glu may be used in the compounds disclosed herein as a recognition moiety. Without being limited by any theory, it is hypothesized that γ-Glu may be hydrolyzed by GGT, followed by 1,6 benzyl elimination to release DTC specifically in cancer cells In some embodiments, the dithiocarbamate prodrug comprises, consists of, or consists essentially of the γ-glutamyl transferase activated prodrug Glu-DTC having the formula shown in FIG. 3 and any salts, esters, and derivatives thereof. In some embodiments, disclosed are representative compounds that include a γ-glutamyl transferase (GGT) targeting or recognizing moiety, such as the compound shown in FIG. 3, or a pharmaceutically accept salt, amide, or ester thereof Class 2: Receptor Targeting Dithiocarbamate Prodrugs In some embodiments, the disclosed compounds may function as receptor targeting prodrugs, which target overexpressed receptors for enhanced uptake in the cancer cells. In some embodiments, the DTC moiety is attached the remaining part of the disclosed compounds via a disulfide bond. Intracellular condition may reduce the disulfide linkage and release DTC.

A. Folic Acid (FA) Conjugated Prodrug, FA-DTC

In some embodiments, the disclosed compounds include a folic acid moiety. These folic acid conjugated dithiocarbamate compounds may take advantage of the high affinity of the vitamin folic acid for the membrane-anchored Folate Receptor, a recognized tumor antigen. A number of folate-drug conjugates have been evaluated in clinical trials, including a Phase 3 for Endocyte's folate-vinblastine conjugate vitafolide. In some embodiments, the disclosed compounds include a folic acid moiety conjugated to DTC through a cysteine containing peptide via a disulfide linker. The peptide may serve as a spacer to preserve optimal folate binding to its receptor, as well as to increase water solubility of the construct. In some embodiments, upon entering a cell, the DTC moiety may be released from the disclosed compounds by the intracellular disulfide reduction processes.

Figure 4:
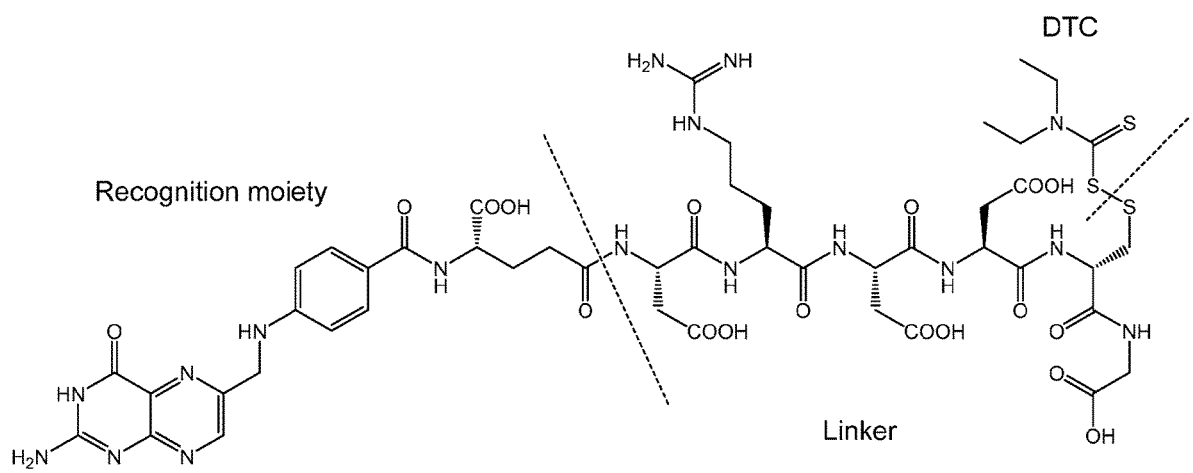
FIG. 4 shows the chemical structure of FA-DTC, including: the Recognition moiety—Folic Acid; the Linker—Cysteine containing peptide; the Chelator—DTC.

In some embodiments, the dithiocarbamate prodrug comprises, consists of, or consists essentially of the folic acid conjugated prodrug FA-DTC having the formula shown in FIG. 4 and any salts, esters, and derivatives thereof. In some embodiments, disclosed are representative compounds that include a folate receptor targeting or recognizing moiety, such as the compound shown in FIG. 4, or a pharmaceutically accept salt, amide, or ester thereof.

B. Prostate Specific Membrane Antigen (PSMA) Targeting Prodrug (PSMA-DTC)

Figure 5:
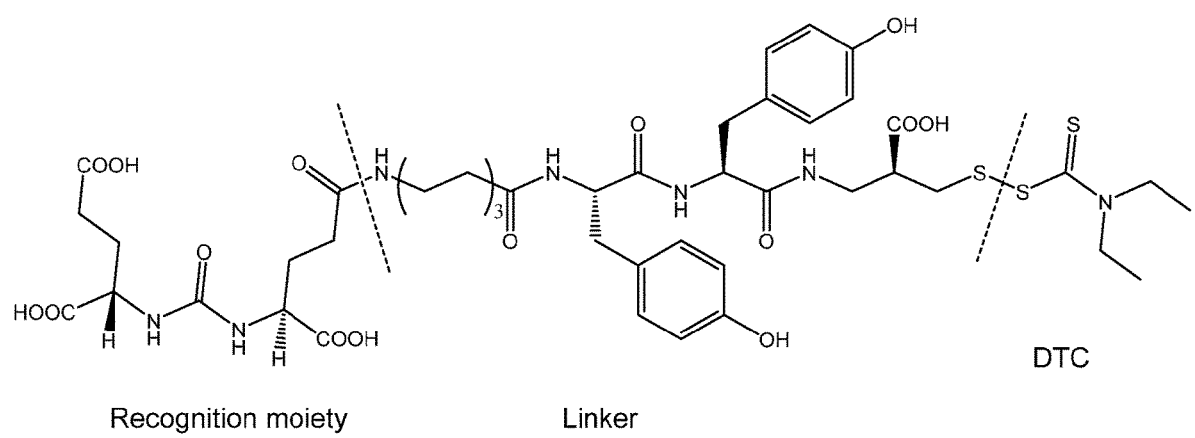
FIG. 5 shows the chemical structure of DUPA-DTC, including: the Recognition moiety—DUPA; the Linker—Cysteine containing peptide; the Chelator—DTC.

In some embodiments, the disclosed compounds may include a moiety that targets or recognizes prostate specific membrane antigens. For example, disclosed is a dithiocarbamate prodrug comprising, consisting of, or consisting essentially of the prostate specific membrane antigen targeting prodrug PSMA-DTC having the formula shown in FIG. 5 and any salts, esters or derivatives thereof.

In some embodiments, the disclosed PSMA-DTC compounds exploit the affinity of 2-[3-(1,3-dicarboxypropyl)ureido] pentanedioic acid, DUPA, to Prostate Specific Membrane Antigen (PSMA), which is overexpressed in prostate tumor. PSMA targeted radioimaging agents for prostate tumor have been synthesized by conjugating $^{99}$Tc complex to DUPA. DUPA has also been conjugated to various cytotoxic drugs to develop targeted delivery of anticancer agents. In some embodiments, the disclosed compounds include a dithiocarbamate conjugated to DUPA through disulfide conjugation from cysteine containing linker. Without being limited by any theory, it is hypothesized that the disclosed compounds may target prostate cancer cells via the membrane receptors (e.g. PSMA), and upon entering the cells the DTC may be released from the disclosed compounds by intracellular reduction of disulfide.

While there is some precedent of these particular prodrug strategies for improving the efficacy of existing clinical anticancer drugs, no one has used the approaches as disclosed here to deliver an agent that operates based on the altered copper biology of a disease state. Upon release of DTC, it is hypothesized that $[Cu(DTC)_2]$ forms in situ in the relatively high Cu environment of cancer cells (such prostate cancer cells) to act as the toxic agent.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present invention also includes an isotopically-labeled compound, which is identical to those recited in the present disclosure, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of the present disclosure are $^{11}$C, $^{13}$N, $^{15}$O, and $^{18}$F. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

The disclosed compounds may exist as pharmaceutically acceptable esters or amides. For example, compounds having a carboxylic acid group may have the corresponding esters or amides compounds as derivatives or precursors. Representative carboxylic acid esters include, for example, methyl, ethyl, isopropyl, or n-butyl, aryl, acyloxymethyl, alkyloxycarbonyloxymethyl, benzoyloxymethyl, (oxodioxolyl)methyl, aminocarbonyloxymethyl, or N-alkyl-N-alkyloxycarbonylaminomethyl (NANOCAM)) esters.

3. Pharmaceutical Compositions

In one aspect, disclosed is a pharmaceutical composition comprising an effective amount of a compound of formula (I) as described herein, or a pharmaceutically accept salt, amide, or ester thereof, and a pharmaceutically acceptable carrier.

In some embodiments, the pharmaceutical composition includes an effective amount of a compound selected from the group consisting of

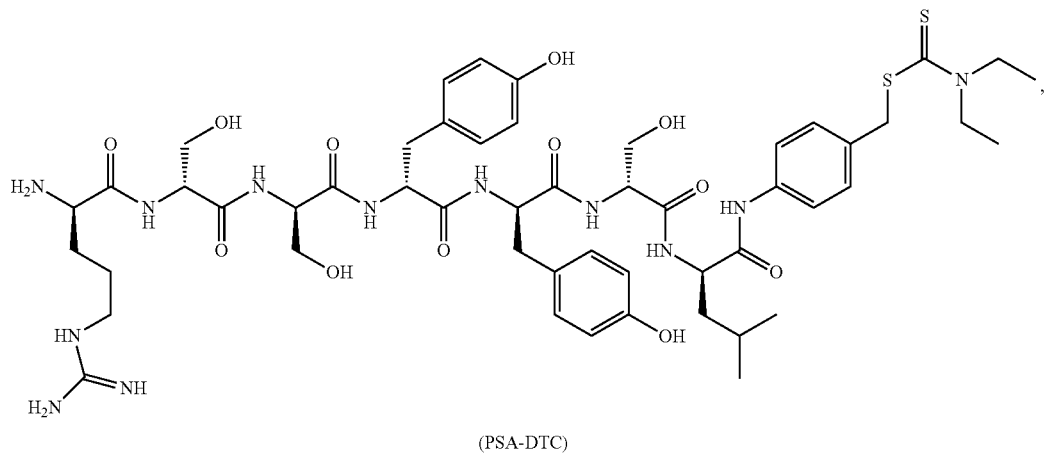

(PSA-DTC)

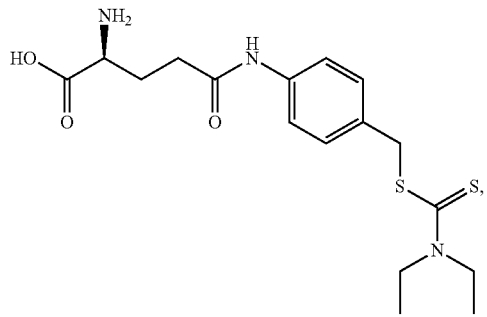

(Glu-DTC)

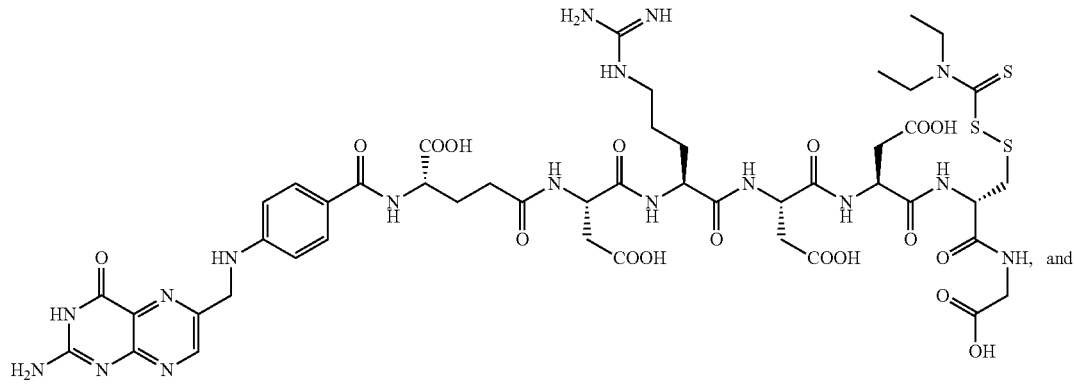

(FA-DTC)

-continued

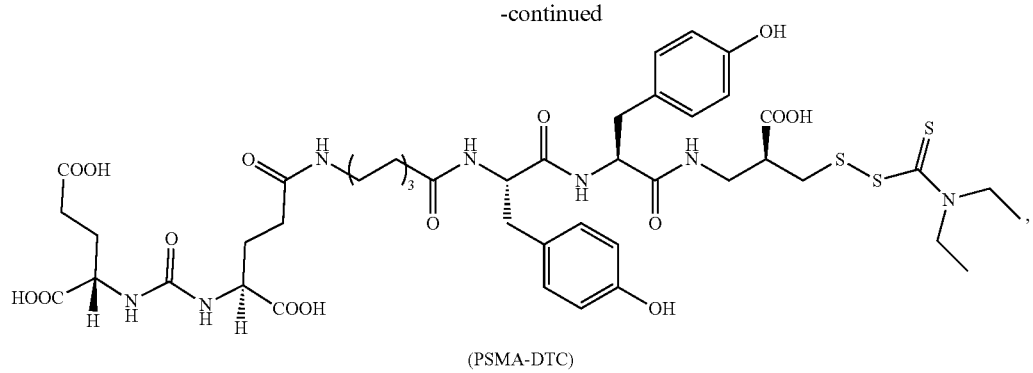

(PSMA-DTC)

or a pharmaceutically accept salt, amide, or ester thereof.

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the disclosed compound. A "therapeutically effective amount" refers to an amount effective, at dosages and for periods of time necessary, to achieve the desired therapeutic result, such as beneficial or desirable biological and/or clinical results. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the disclosed compounds and their physiologically acceptable salts, amide, or ester may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active compound and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound, and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

The compounds and processes of the invention will be better understood by reference to the following examples, which are intended as an illustration of and not a limitation upon the scope of the invention.

4. Methods of Use

The compounds, compositions, and methods provided herein exploit the unique microenvironment of drug-resistant cancer cells to conditionally form cytotoxic Cu-dithiocarbamate complexes exclusively in cancer cells, in particular prostate cancer cells. The targeted DTC derivatives disclosed herein may minimize cellular uptake by normal, healthy cells, which will in turn minimize off-target protein inhibition and undesirable metabolite activity that constitute the usual bioactivities of disulfiram. Furthermore, the prodrug compounds disclosed herein may prevent Cu coordination prior to cancer cell entry, thereby maximizing the cytotoxic synergy between the drug and the increased copper accumulation inherent in prostate cancer biology.

Another aspect of the present disclosure provides a methods of treating a subject suffering from cancer comprising, consisting of, or consisting essentially of the steps of administering to the subject a therapeutically effective amount of a dithiocarbamate prodrug as described herein such that the cancer is treated.

In one embodiment, disclosed is a method of treating cancer in a subject in need thereof, which comprises administering to the subject a therapeutically effective amount of a compound of formula (I) as described herein, or a pharmaceutically accept salt, amide, or ester thereof, whereby the cancer is treated.

As is known in the art, a cancer is generally considered as uncontrolled cell growth. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer comprises pancreatic cancer. In certain embodiments, the cancer comprises prostate cancer.

The term "subject" and "patient" are used interchangeably and refer to any animal being examined, studied or treated. It is not intended that the present disclosure be limited to any particular type of subject. In some embodiments of the present disclosure, humans are the preferred subject, while in other embodiments nonhuman animals are the preferred subject, including but not limited to mice, monkeys, ferrets, cattle, sheep, goats, pigs, chicken, turkeys, dogs, cats, horses and reptiles. In some embodiments, the subject is suffering from cancer. In certain embodiments, the subject is suffering from prostate cancer.

As used herein, the terms "treat," "treatment," and "treating" refer to the reduction or amelioration of the severity, duration and/or progression of a condition or one or more symptoms thereof resulting from the administration of one or more therapies. Such terms may refer to a reduction in UV damage to a cell, tissue or organ, or a reduction and/or loss of function in the cell, tissue or organ. The term "treatment," as used herein in the context of treating cancer may pertain to treatment and therapy of a human or an animal, in which a desired therapeutic effect is achieved. For example, treatment may include prophylaxis and may ameliorate or remedy the condition or symptom of cancer, or treatment may inhibit the progress of cancer (e.g., reduce the rate of cancer progression or halt the rate of cancer progression).

In another aspect, the present disclosure provides a method of preventing or attenuating cancer in a subject comprising, consisting of, or consisting essentially of administering to the subject a therapeutically effective amount of a dithiocarbamate prodrug as described herein such that the cancer is prevented or attenuated.

In one embodiment, disclosed is a method of preventing cancer in a subject in need thereof, which comprises administering to the subject a therapeutically effective amount of a compound of formula (I) as described herein, or a pharmaceutically accept salt, amide, or ester thereof, whereby the cancer is prevented.

In another embodiment, disclosed is a method of attenuating a cancer in a subject in need thereof, which comprises administering to the subject a therapeutically effective amount of a compound of formula (I) as described herein, or a pharmaceutically accept salt, amide, or ester thereof such that the cancer is attenuated.

The term "effective amount" or "therapeutically effective amount" as used herein in the context of treating, results preventing, or attenuating a cancer refers to an amount sufficient to effect beneficial or desirable biological and/or clinical.

As used herein, the term "prevent" refers to the prevention of the formation of a cancer in a subject. The term "attenuate" refers to the lessening or reduction of a cancer.

In certain embodiments, disclosed are methods of treating, preventing, or attenuating prostate cancer in a subject in need thereof, which comprises administering to the subject a therapeutically effective amount of a compound of formula (I) as described herein, or a pharmaceutically accept salt, amide, or ester thereof, whereby the prostate cancer is treated, prevented, or attenuated.

In particular embodiments, disclosed are methods of treating, preventing, or attenuating a cancer (such as prostate cancer) in a subject in need thereof, which comprises administering to the subject a therapeutically effective amount of a compound selected from the group consisting of

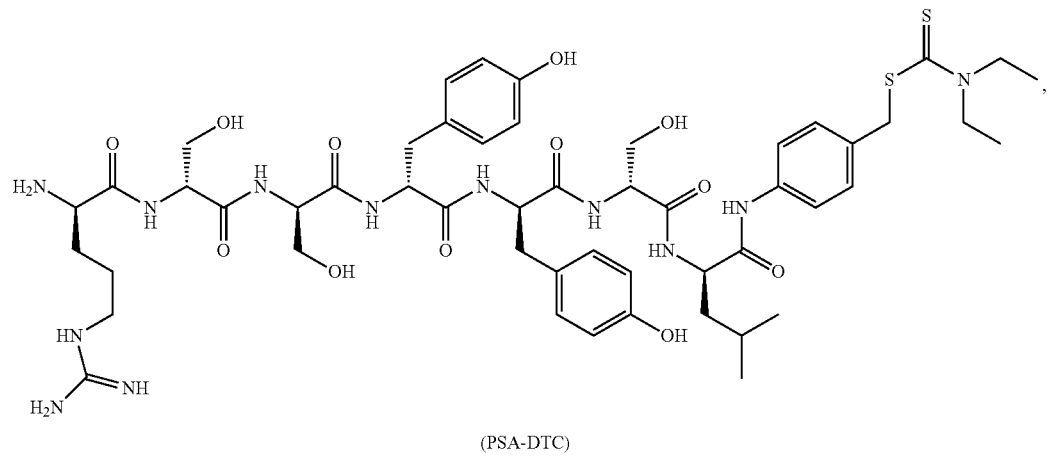

(PSA-DTC)

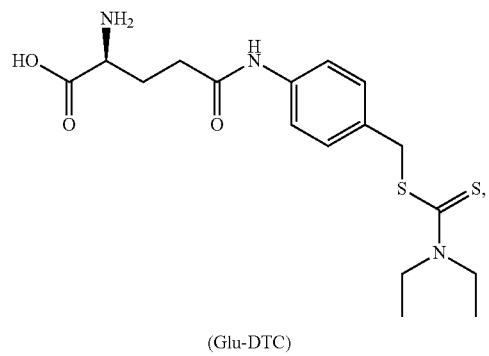

(Glu-DTC)

-continued

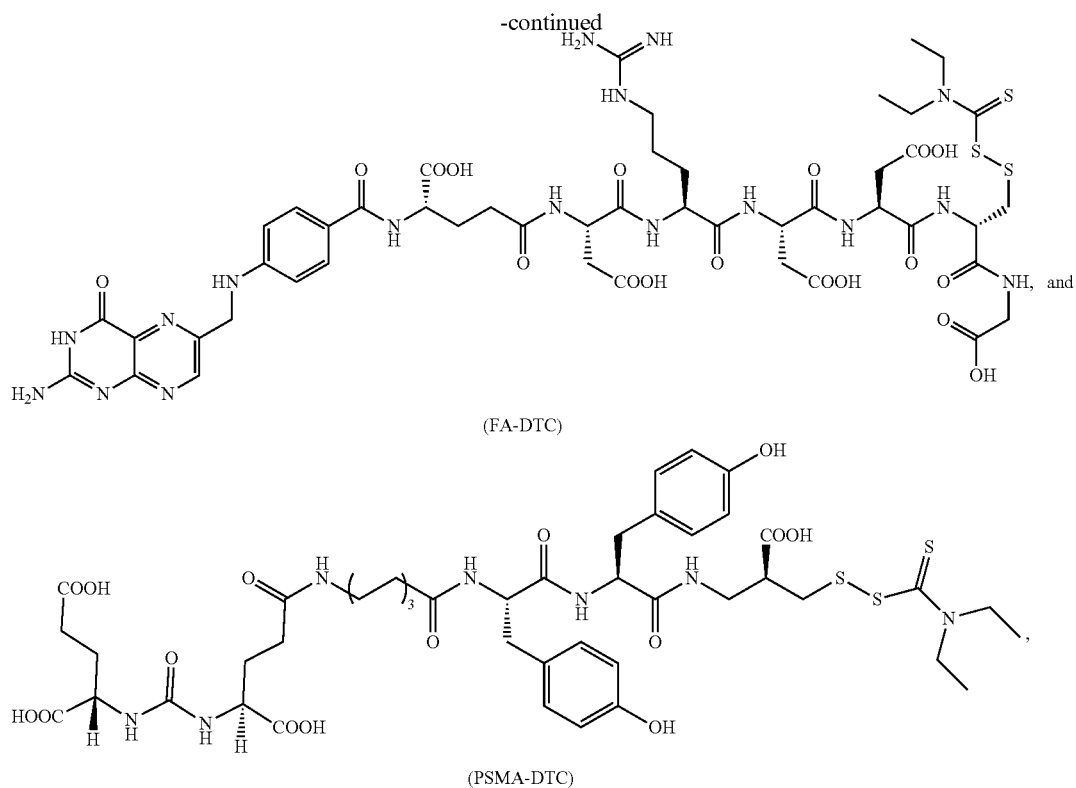

(FA-DTC)

(PSMA-DTC)

or a pharmaceutically accept salt, amide, or ester thereof, whereby the cancer is treated, prevented, or attenuated.

In other embodiments, the methods as described herein further comprises co-administering to the subject an additional anticancer therapy. As used herein, the terms "anticancer therapy," "anticancer treatment" and/or "anticancer therapy regimen" refer to the clinical intervention made in response to a disease, disorder or physiological condition (e.g., cancer) manifested by a patient or to which a patient may be susceptible. The aim of treatment includes the alleviation or prevention of symptoms, slowing or stopping the progression or worsening of a disease, disorder, or condition and/or the remission of the disease, disorder or condition. Anticancer treatments may include, but are not limited to, radiation, chemotherapy, immunotherapy, targeted therapy, hormone therapy, surgery, stem cell transplants, precision medicine and combinations thereof.

In some embodiments, the anticancer therapy is administered prior to the administration of the compound of formula (I) as described herein or a pharmaceutically accept salt, amide, or ester thereof.

In some embodiments, the anticancer therapy is administered concurrently with the administration of the compound of formula (I) as described herein, or a pharmaceutically accept salt, amide, or ester thereof.

In some embodiments, the anticancer therapy is administered after the administration of the compound of formula (I) as described herein, or a pharmaceutically accept salt, amide, or ester thereof.

5. Kits

In another aspect, the present disclosure also provides a kit for the treatment of a cancer comprising, consisting of, or consisting essentially of a dithiocarbamate prodrug as provided here, instruments for the administration of the dithiocarbamate prodrug, and instructions for use.

In one embodiment, provided is a kit for the treatment of a cancer comprising a compound of formula (I) as described herein, or a pharmaceutically accept salt, amide, or ester thereof, instruments for the administration of the compound, and instructions for use. For example, the kit may include the disclosed compound or a pharmaceutically accept salt, a pharmaceutical composition thereof, or both; and information, instructions, or both, regarding methods of application or administration of the disclosed compound or a pharmaceutically accept salt, or of composition, with the benefit of treating, preventing, or attenuating cancer in mammals (e.g., humans).

6. Examples

Abbreviations used in the examples and reaction schemes that follow are:
ACN acetonitrile
Boc tert-butyloxycarbonyl
DBU 1,8-Diazabicyclo [5.4.0]undec-7-ene
DCM dichloromethane
DMEM Dulbecco's modified eagle medium
DMF N,N-dimethylformamide
DMSO dimethyl sulfoxide
DSF disulfiram
DTC diethyldithiocarbamate
DUPA 2-[3-(1,3-dicarboxypropyl)ureido]pentanedioic acid
EDTA ethylenediaminetetraacetic acid
E-pNA, γE-pN or γ-Glu(p-NA) 1-glutamic acid γ-(p-nitroanilide)
FA folic acid or folate
Fmoc fluorenylmethyloxycarbonyl GGT γ-glutamyl transferase
GSH glutathione
h or hr hour
HBTU N,N,N',N'-Tetramethyl-O-(1H-benzotriazol-1-yl) uronium hexafluorophosphate
HPLC high-performance liquid chromatography
$IC_{50}$ half maximal inhibitory concentration
LC-MS liquid chromatography-electrospray mass spectrometry
MeOH methanol
min minute(s)
NMM N-methylmorpholine
PAB p-aminobenzyl alcohol
PBS phosphate buffered saline
PSA prostate-specific antigen
PSMA prostate-specific membrane antigen
rt or r.t. room temperature
THF tetrahydrofuran
TLC thin-layer chromatography Example 1: Materials and Methods All solvents were purchased from Fisher Scientific and were of ACS grade unless otherwise noted. All commercially available compounds were used without further purification unless otherwise noted. All water used was deionized and distilled. Liquid chromatography-electrospray mass spectrometry (LC-MS) was performed on an Agilent 1100 series HPLC in line with an MSD ion trap and a Daly conversion dynode detector. HPLC was performed using a Waters Delta 600 HPLC utilizing a Hychrom Ultrasphere 5 ODS (250×4.6 mm) analytical C-18 column with the UV-Vis detector set at 225 and 254 nm. $^1$H NMR and $^{13}$C NMR spectra were collected in either $CDCl_3$ or $(CD_3)_2SO$ (Cambridge Isotope Laboratories, Cambridge, Mass.) at 25° C. on a Varian 600 MHz spectrometer. Microplate absorbance and fluorescence readings were performed on a PerkinElmer Victor 1420 plate reader. Working solutions of $CuSO_4$ were diluted from a 100-mM stock solution that was standardized for [Cu] by titration against EDTA with a Murexide endpoint.

Calcein assay: In a 96-well plate 12.5 μM prodrug or DTC chelator was dissolved in PBS (pH=7.4) from a 20 mM stock solution in DMSO. To each well Calcein (Cu) was added to reach a final concentration of 1 μM. The fluorescence of calcein was measured using a plate reader with λex=485 nm and λem=535 nm. After measuring the initial fluorescence, Gly-Gly and GGT were added in each well to make up to a final concentration of 1 mM and 20 U/L respectively. The plate was scanned at various time points to observe prodrug turnover via the development of a fluorescent signal caused by Cu removal from Calcein. The fluorescence emission was plotted as percentage with fluorescence of 1 μM Calcein in PBS as 100% and 1 μM (Cu)Calcein as 0%. The experiment was repeated in triplicate and standard deviations are represented as error bars.

GGT Enzyme cleavage assay: In order to detect DTC liberated from prodrug by reactivity with GGT, 100 μM Glu-DTC was exposed to 100 U/L GGT in the presence of 1 mM Gly-Gly (PBS; pH 7.4; 37° C.). After 15 min, 500 μM $CuSO_4$ was added to the vial, mixed well, then analyzed by LC/MS using an $H_2O$: acetonitrile gradient for 25 min starting with 95% $H_2O$:acetonitrile to 5% $H_2O$:acetonitrile. A peak eluting at 12 min was observed corresponding to Glu-DTC as detected by MS, while a second peak eluting at 22 min corresponded to $Cu(DTC)_2$ as detected by MS. A decrease in Glu-DTC peak and formation of $Cu(DTC)_2$ was observed upon treatment with GGT enzyme.

Competition experiments vs. γE-pNA for GGT: To perform the inhibition study, a serial dilution of γE-pNA was performed ranging from 1 mM to 3 μM in PBS with 1 mM Gly-Gly (dilution factor=0.5; pH 7.4; 10% DMSO; 100 μL) using a clear, flat bottom 96 well plate. GGT binding molecules, as indicated, were added to separate sets of triplicate wells to reach a final concentration of 10 and 100 μM. Before the addition of enzyme, the plate was cooled to 4° C. for 15 min. To initiate the assay, 10 μL of 50 U/L GGT was added to each well and an initial absorbance scan was performed. Subsequent scans were performed every 10 min for ~2 h. In between each scan, the plates were stored at 37° C. in a humidified incubator to reduce solvent evaporation. The experiment was repeated in triplicate.

Glu-DTC cleavage in cell culture: 22Rv1 and PWR-1E cell lines were plated into a 24 well plate (2×105 cells/well) with their respective growth media and allowed to adhere overnight. The following day, the growth media was removed, and each cell line was washed with PBS. 2 mL of 100 μM Glu-DTC in serum free media along with 1 mM Gly-Gly was added to the cells. One batch of 22Rv1 were treated with 2 mM Acivicin, a GGT inhibitor, along with Glu-DTC and Gly-Gly. 100 μL aliquots were taken at various time points over 72 h. Each aliquot was analyzed via HPLC to generate chromatographs of the progress of Glu-DTC digestion. Caffeine was added as reference and the ratio of Glu-DTC peak area with respect to caffeine was plotted as percentage considering initial Glu-DTC level as 100%.

Determination of GGT activity in cells: GGT activity was measured in 22Rv1, LNCaP, MCF-7, PC-3, and PWR-1E cells. Cells (2×105 cells/well) were seeded in a 24 well plate and allowed to adhere for 24 h. The cells were dosed with 1 mM γ-Glu(p-NA) and 1 mM Gly-Gly in serum free medium (RPMI medium for 22Rv1, LNCaP, and PC-3; DMEM for MCF-7; Keratinocyte-SFM for PWR-1E). The cells were then incubated for 72 h at 37° C. during which 100 μL aliquots were taken at multiple time points and absorbance at 405 nm was measured. Turnover rates (ΔA/min) were acquired via linear regression of the compiled data. A standard curve for GGT activity was obtained by measuring the turnover rates of γ-Glu(p-NA) for varying amounts of a standard isolated GGT enzyme. Turnover rates from cellular activity were interpolated to standard curve to obtain the GGT activity in the cells. All experiments were performed in triplicate and the experiments were repeated three times. Standard deviation is reported as error. PWR-1E cells displayed <0.1 U/L activity which was the least measurable activity at the given conditions and duration of the experiment.

Antiproliferation assay: To determine the amount of Cu(II) required for cell studies a checkerboard assay was performed by varying the prodrug or drug concentration and Cu(II) concentration. 22RV1, LNCaP, PC3, MCF-7, and PWR-1E (5,000 cells/well) were seeded in 96-well plates with regular media (22Rv1, LNCaP, and PC-3 in RPMI with 10% FBS; MCF-7 in DMEM with 10% FBS; PWR-1E in Keratinocyte-SFM) and let adhere for 24 h. The following day, the media was replaced with serum free media and cells were treated as indicated for an additional 24 h or 72 h. Cell proliferation was measured using a fluorometric resazurin reduction method. 20 μL of 700 μM Resazurin (Sigma R7017) was added in each well and incubated at 37° C. for 2 h. Fluorescence at 580 nm was measured by exciting at 555 nm with a plate reader. Each experiment was performed in triplicate, and the experiments were repeated three times. Viability vs drug concentration plot from a representative experiment are shown with standard deviation from the experiment as error bar. The error bar in IC50 values represents standard deviation from three different experiments.

Example 2: PSA Cleavable Prodrug

Synthesis of PSA Cleavable Prodrug, PSA-DTC

PSA targeted prodrug was synthesized via scheme 1. The PSA targeting peptide was synthesized by solid phase peptide synthesis. Commercially available Fmoc-protected leucine was coupled with p-aminobenzyl alcohol (PAB) by following standard amide coupling protocol. Following bromination, intermediate 2 was reacted with sodium diethyl dithiocarbamate to give 3. Fmoc deprotection of 3 affords Leu-PAB-DTC 4. Compound 4 was coupled to the PSA targeting peptide synthesized via solid phase peptide synthesis to give PSA-DTC, PSA-targeting prodrug (Scheme 1).

In Vitro Release of the PSA Cleavable Prodrug

Two isomers of PSA-DTC were synthesized. One with all L-amino acids (PSA-DTC) and one with D-Ser in second position from C-terminal (dPSA-DTC). Enzymes tend to act generally on L-amino acid more efficiently than D-amino acids.

Figure 6A:
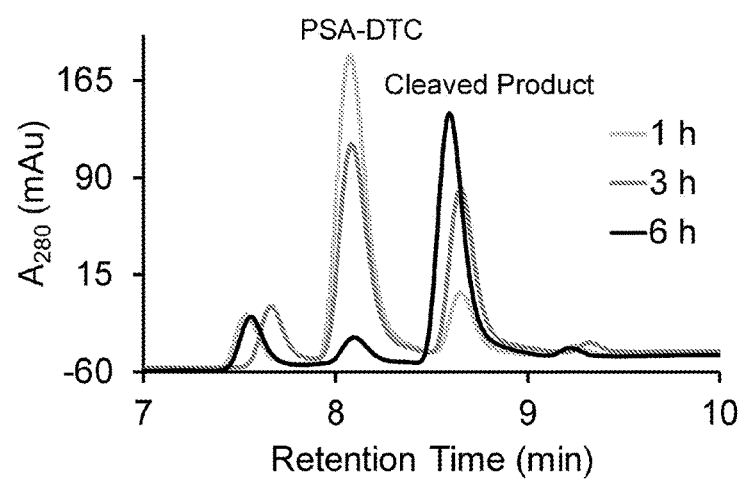
FIGS. 6A-6B shows Liquid Chromatography trace at 280 nm for PSA-DTC (FIG. 6A) and dPSA-DTC (FIG. 6B) at different timepoint of exposure (1 h, 3 h, 6 h) to 20 μg/mL PSA enzyme in accordance with one embodiment of the present disclosure.
Figure 6B:
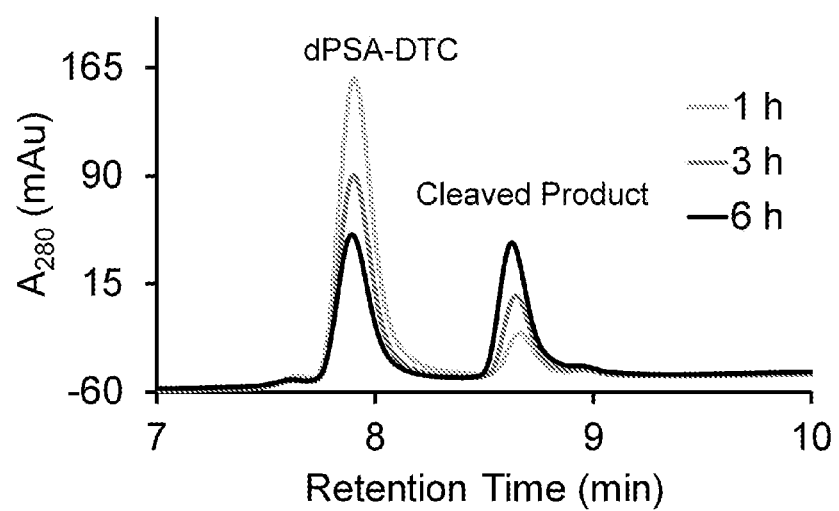

It is hypothesized that the SA enzyme cleaves the peptide bond between Tyr and Ser. The cleaved products are shown in Scheme 2. When treated with 20 µg/mL of PSA, PSA-DTC was completely converted to products within 6 h (FIG. 6A). While only partial conversion was observed for dPSA-DTC within 6 h (FIG. 6B). Further treatment with aminopeptidases led to the release of DTC in PSA-DTC whereas aminopeptidases could not cleave the d-Ser-Leu-PAB-DTC. Based on these in vitro results PSA-DTC is expected to be more active than dPSA-DTC that cannot release DTC.

Scheme 1: Synthesis of PSA targeting prodrug.

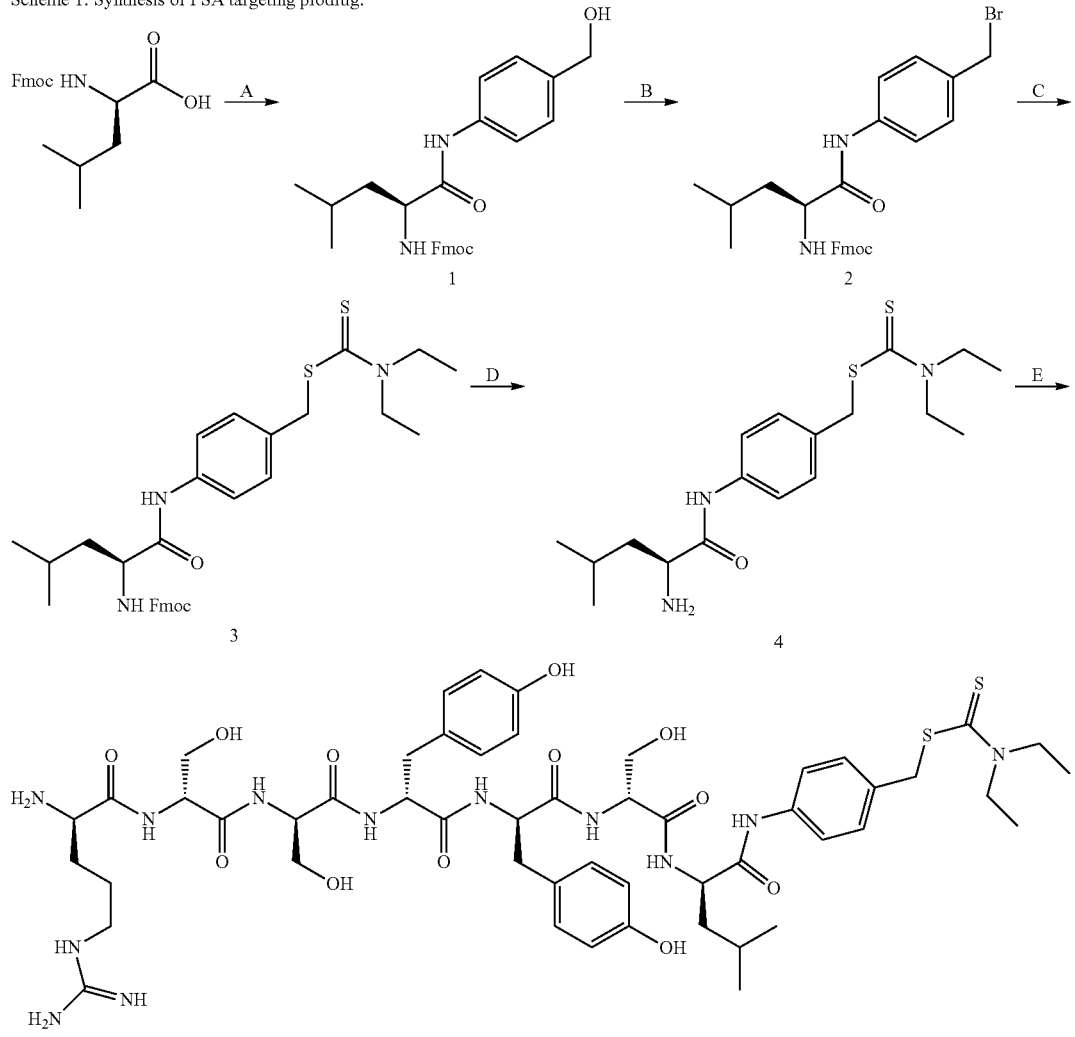

PSA-DTC

A) p-Aminobenzyl alcohol, HBTU, 4% NMM in DMF, 3 h, rt, 63% B) PBr3, Dry THF, 3 h, 0° C., 78%;
C) (i) Sodium diethyldithiocarbamate, Dry, THF, 12 h, rt (ii) 1% DBU in THF, 5 min, rt, 85%; D) FmocRSSYYS, HOBt, EDC, DIPEA, DMF, 12 h, rt; E) 20% piperidine in DMF, 3 h, rt.

Scheme 2: PSA enzyme cleavage products Arg-Ser-Ser-Tyr and Ser-Leu-PAB-DTC of the prodrug.

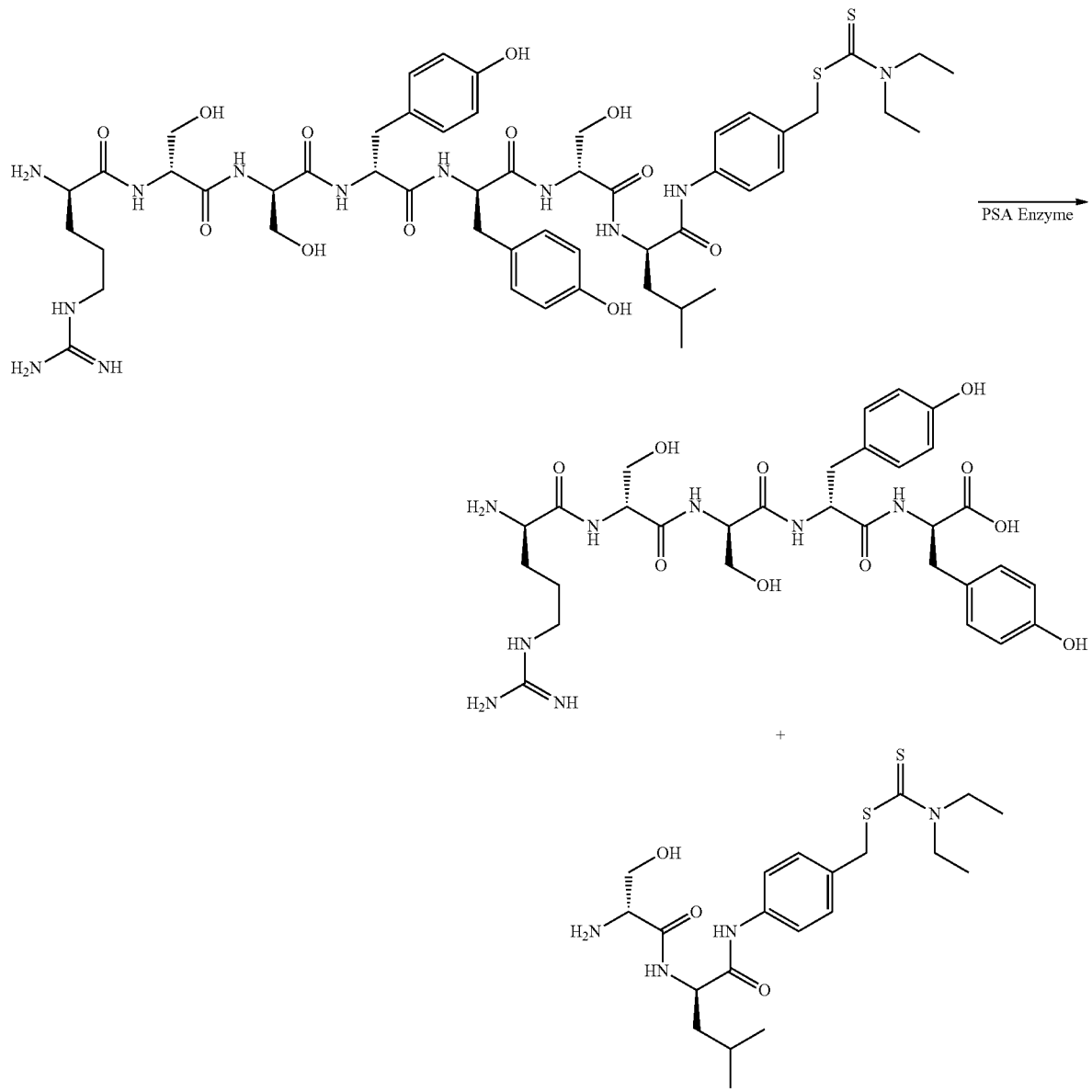

Biological Activity of the PSA Cleavable Prodrug

Figure 7A:
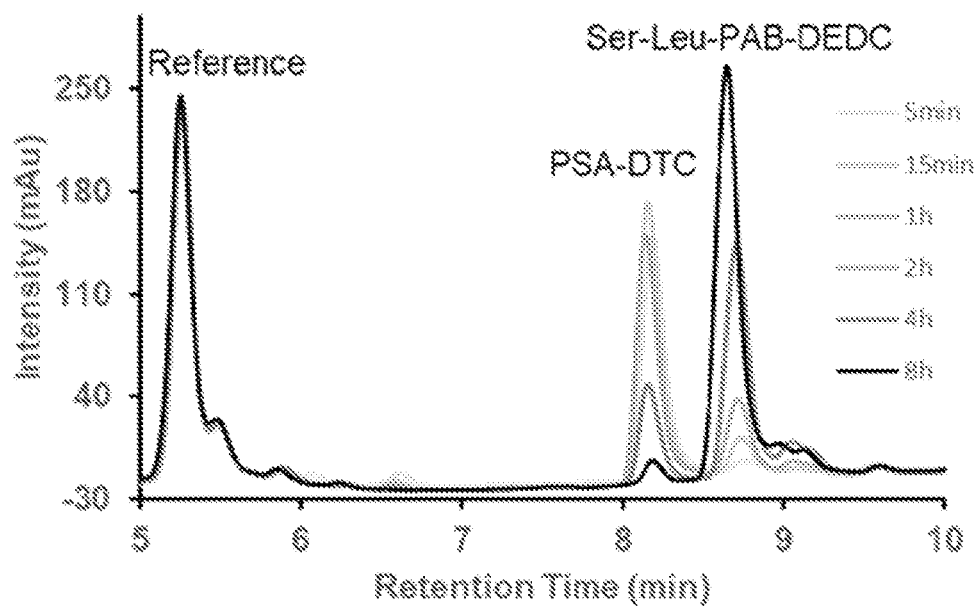
FIG. 7A shows a LC traces of PSA-DTC at different timepoints in the LNCaP conditioned media with caffeine as reference.
Figure 7B:
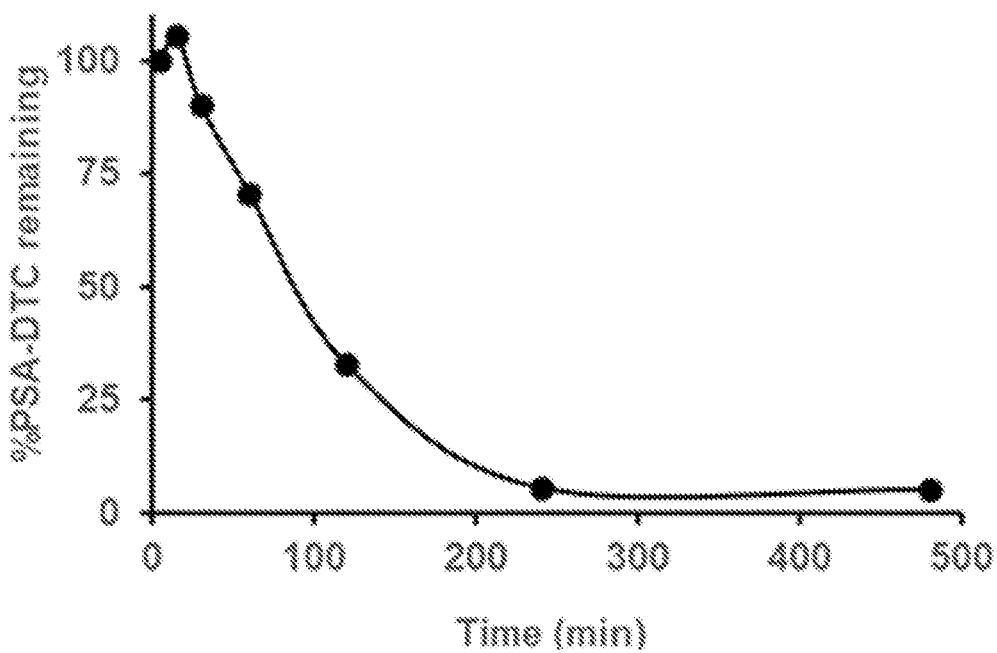
FIG. 7B shows the percentage PSA-DTC remaining as calculated from the LC-peak at 280 nm.
Figure 7C:
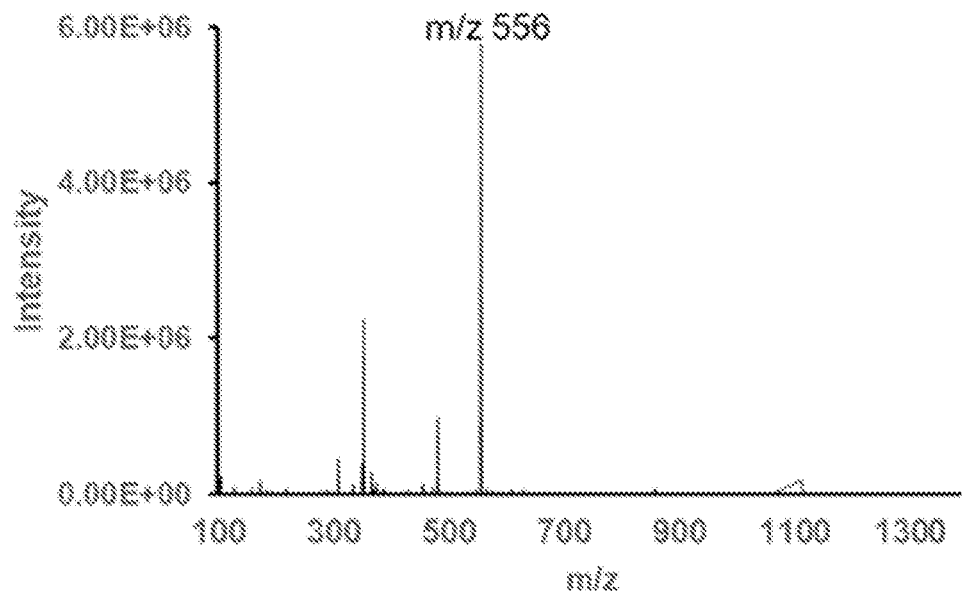
FIG. 7C shows the mass spectra of the LC-peak at 8.2 min showing m/z 556 for PSA-DTC.
Figure 7D:
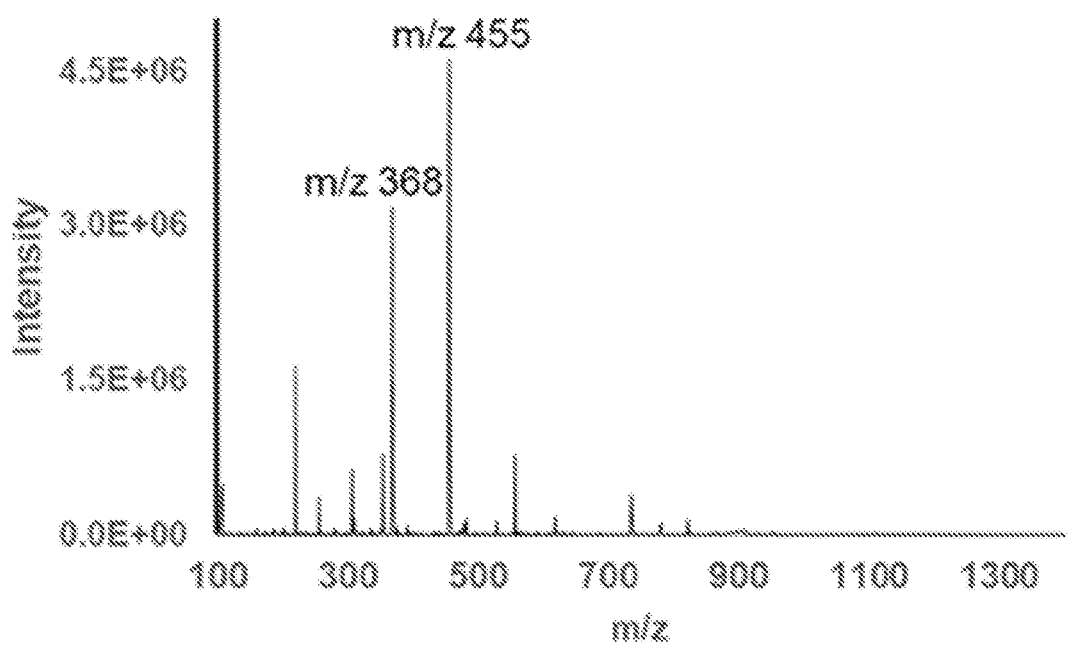
FIG. 7D shows the mass spectra of the LC-peak at 8.8 min showing m/z 368 and 456 for Ser-Leu-PAB-DTC and Leu-PAB-DTC in accordance with one embodiment of the present disclosure.

Conditioned media from prostate cancer cell line, LNCaP, was used to test the cleavage of prodrug. Liquid chromatography-mass spectrometry (FIG. 7A) showed that PSA-DTC (retention time 8.2 min, m/z 556, FIG. 7A and FIG. 7C) was cleaved to release Ser-Leu-PAB-DTC (retention time 8.8 min, m/z 455, FIG. 7A and FIG. 7D), Leu-PAB-DTC (retention time 8.8 min, m/z 368, FIG. 7A and FIG. 7D) and DTC. Since DTC is not observed in the UV or mass spectrometer, Cu(II) was added before recording mass spectra to visualize the release of DTC. Cu(DTC)$_2$ complex was observed indicating the release of DTC. PSA-DTC was completely cleaved within 4 h. These data validate the expected outcome of release of DTC under cell culture conditions.

Figure 8A:
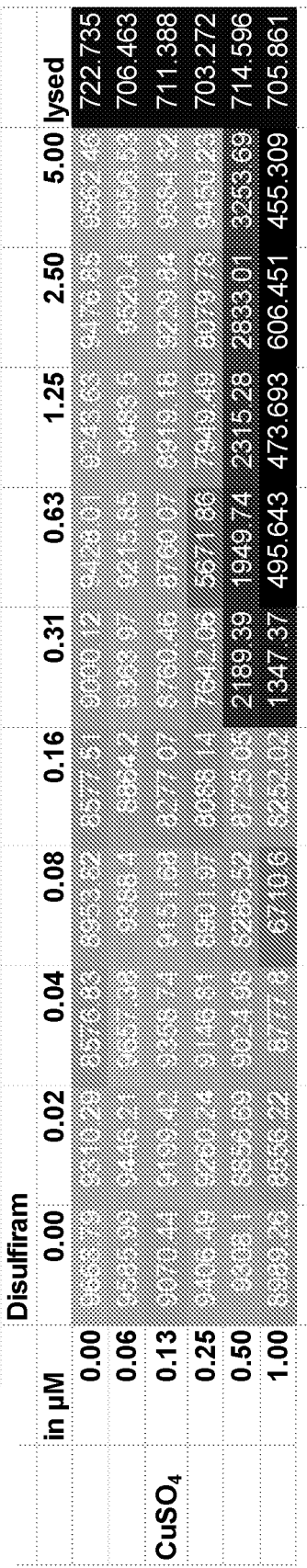
FIG. 8 shows a checker board assays in LNCaP cells with varying copper concentrations and prodrug concentrations in μM in RPMI media containing 10% FBS. The results range from most viable to least viable. Numbers in each block corresponds to resazurin fluorescence used to measure viability. Right most lane is negative control with complete lysis. Results for disulfiram (FIG. 8A), PSA-DTC (FIG. 8B), and dPSA-DTC (FIG. 8C) are shown in accordance with one embodiment of the present disclosure.
Figure 8B:
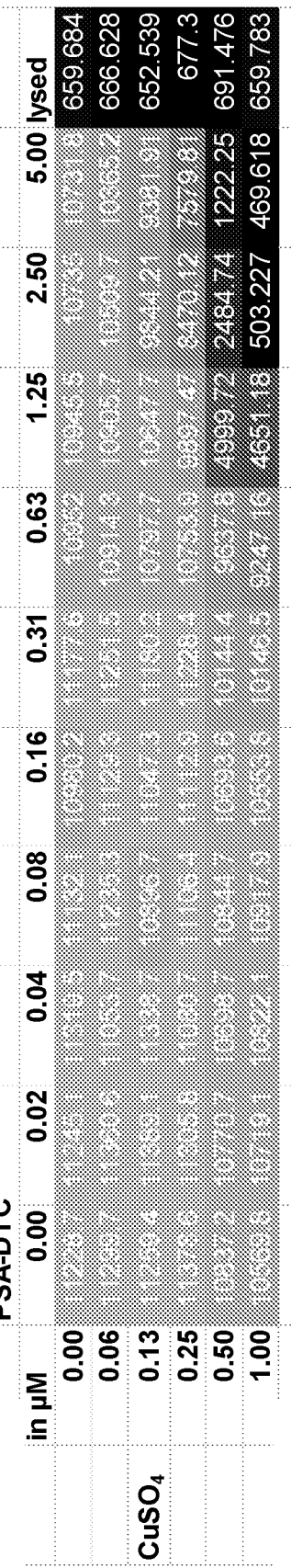
Figure 8C:
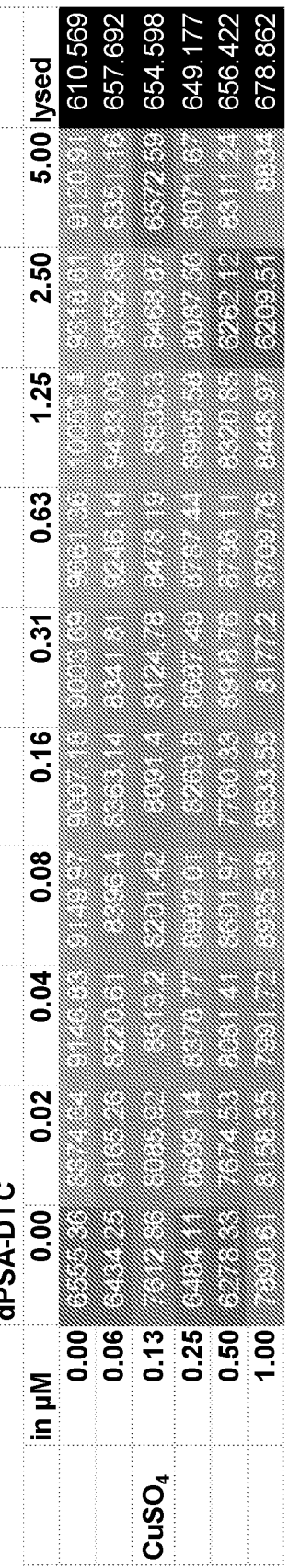

The activity of the PSA cleavable prodrugs was tested in prostate cancer cell lines. Both PSA-DTC and dPSA-DTC were tested in LNCaP cell lines and compared to Disulfiram. Checker board assays with varying concentration of Cu and prodrug were performed in LNCaP prostate cancer cell line. Disulfiram as expected showed a synergy in cytotoxicity with Cu (FIG. 8A). The effect could be seen within 24 h. dPSA-DTC did not show antiproliferative activity even after 72 h (FIG. 8C). PSA-DTC showed antiproliferative activity in the presence of Cu within 24 h. The synergy with Cu was also observed. The synergy pattern was comparable to disulfiram for PSA-DTC (FIG. 8B). This clearly indicates that the efficacy of the prodrug depends on the enzymatic release of the peptide conjugate. The above results prove that the activity of diethyldithiocarbamate, the active component of disulfiram, can be masked and unmasked.

PSA-DTC was further tested in other prostate cancer (PC3 and 22Rv1), prostate normal (PWR-1E), and breast cancer (MCF-7) cell lines. The IC$_{50}$ values are tabulated in Table 1. Based on mRNA levels of PSA (data not shown), activity of PSA-DTC is not expected in PC3, PWR-1E and MCF-7 cells. The comparable $IC_{50}$ of these non PSA-expressing cell lines to $IC_{50}$ in PSA-expressing LNCaP cells suggest other serine proteases, which are ubiquitously expressed in all these cell lines, contribute to the mechanism of action of PSA-DTC in addition to PSA itself. In vitro, cell lines do not express as much active PSA as in vivo. Reports on a similar peptide substrate conjugated to doxorubicin though did not show much selectivity in vitro, although the conjugate demonstrated very good selectivity in vivo in xenograft models. This result is likely due to the higher expression levels of PSA in vivo. Hence it becomes important to further test the molecules in vivo for their efficacy and tolerance when compared to disulfiram.

TABLE 1

| | $IC_{50}$ values in μM | | | | |
|---|---|---|---|---|---|
| Compound | LNCaP | 22Rv1 | PC-3 | PWR-1E | MCF-7 |
| DSF | 0.12 | 0.065 | 0.066 | 0.072 | 0.13 |
| PSA-DTC | 0.39 | 0.77 | 0.49 | 0.50 | 0.33 |

Example 3: GGT Cleavable Prodrug

Synthesis of GGT Cleavable Prodrug

A GGT targeted prodrug was synthesized via the following Scheme 3. Fmoc and methyl protected L-glutamic acid was coupled with p-aminobenzyl alcohol from γ-carboxylic acid followed by bromination. The brominated intermediate was then coupled to diethyldithiocarbamate which was then deprotected to yield the final desired product.

Scheme 3: Synthesis of GGT targeting prodrug.

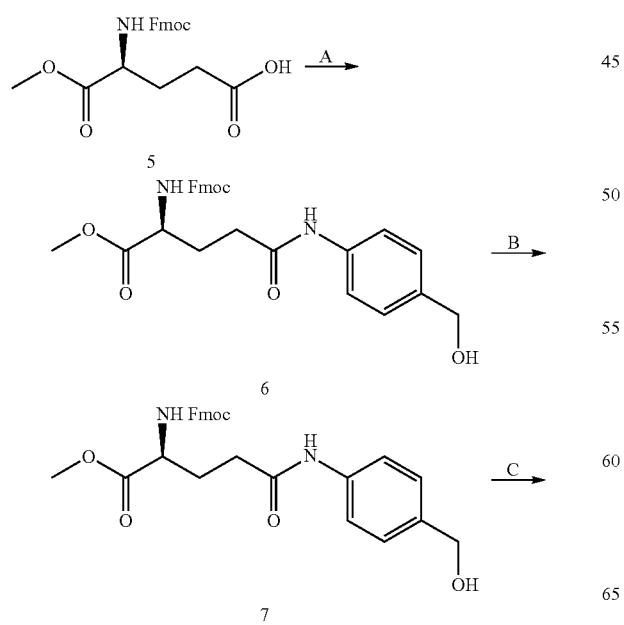

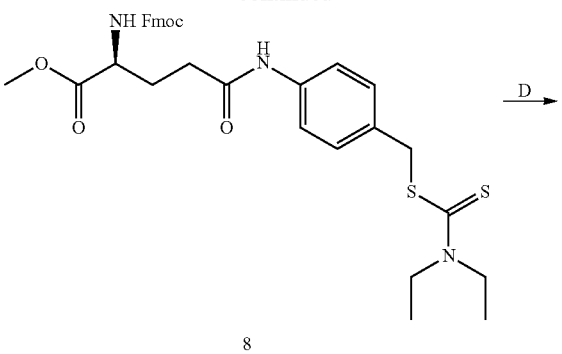

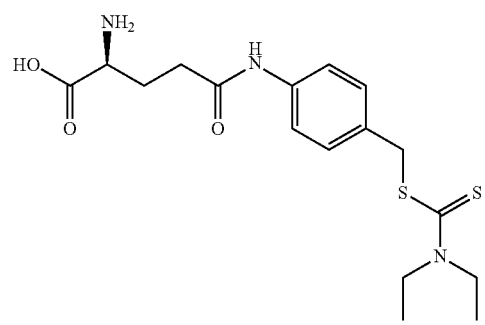

Glu-DTC

A) p-Aminobenzyl alcohol, HBTU, 4% NMM in DMF, 3 h, rt, 74%;
B) PBr3, Dry THF, 3 h, 0° C., 43%; C) (i) Sodium diethyldithiocarbamate, Dry THF, 12 h, rt, 48% (ii) LiOH in THF and $H_2O$, 30 min, rt, D) 20% piperidine in DMF, 1 h, rt, 48%.

Alternatively, the GGT targeted prodrug was synthesized by conjugating commercially available Boc-L-glutamic acid α-tertbutyl ester to p-aminobenzylalcohol using HBTU coupling to generate compound 10 (Scheme 4). Reaction of 10 with $PBr_3$ converted the alcohol functionality to bromide while simultaneously removing the Boc and t-butyl protecting groups to give 11, which was subsequently reacted with sodium diethyldithiocarbamate to yield the final Glu-DTC after purification by HPLC.

Scheme 4: Alternate synthesis of GGT targeting prodrug.

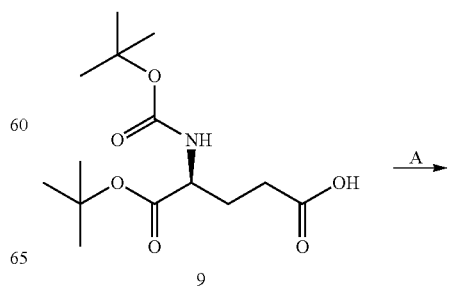

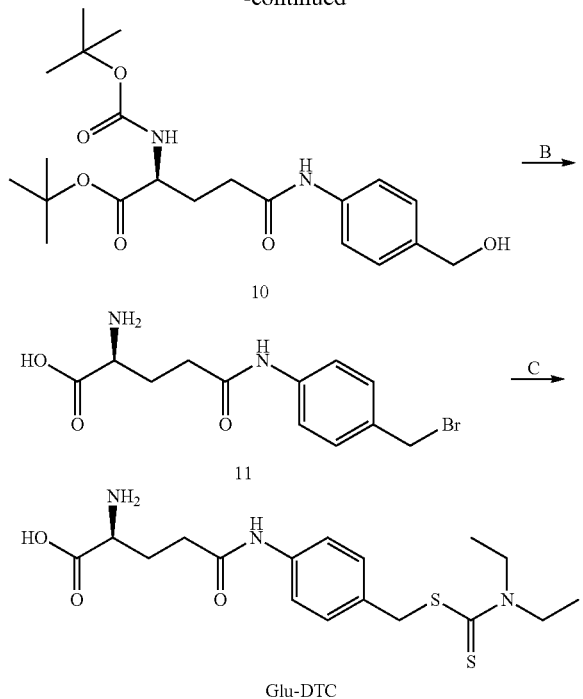

Glu-DTC

A) p-Aminobenzyl alcohol. HBTU, 4% NMM in DMF, 3 h, rt; B) PBr₃, Dry THF, 1 h, 0° C.; C) Sodium diethyldithiocarbamate, Dry ACN, 2 h, rt. Overall yield 11.6%

Boc-GluPAB(OH)-OtBu (10; GluPAB): To a solution of Boc-Glu(OH)-OtBu (155 mg, 0.51 mmol) dissolved in 5 mL of 4% NMM in DMF was added first a portion of HBTU (291 mg, 0.77 mmol), which was left to stir under $N_2$ for 15 min, followed by a portion of p-aminobenzyl alcohol (63 mg, 0.51 mmol). After stirring for 5 h at rt, the full consumption of Boc-E(OH)-OtBu was confirmed by TLC and the reaction mixture was added to 100 mL of DCM and washed 3 times with 100 mL of 10% LiCl in water. The organic layer was dried over sodium sulphate and evaporated to dryness under vacuum. Flash silica-gel chromatography (3.5% MeOH in $CH_2Cl_2$) afforded 10 as a white solid (159 mg, 76%). $^1$H NMR (400 MHz, $CDCl_3$, 298K) δ (ppm) 8.90 (s, 1H), 7.45 (d, J=8 Hz, 2H), 7.2 (d, J=8 Hz, 1H), 5.44 (d, J=8 Hz, 1H), 5.25 (s, 1H), 4.54 (s, 2H), 4.09-4.13 (m, 1H), 2.35 (t, J=6 Hz, 2H), 2.13 (br, 1H), 1.86 (br, 1H). $^{13}$C NMR (100 MHz, DMSO-d6, 298K) δ (ppm) 171.6, 170.2, 155.5, 137.9, 137.1, 126.9, 118.8, 80.3, 78.1, 62.6, 53.9, 38.9, 38.3, 32.6, 28.2, 27.9, 27.7, 26.2. HRMS (m/z): calculated for [MH+] $C_{21}H_{32}N_2O_6$ 409.2333, observed 409.2332.

Boc-GluPAB(Br)—OH (11): A portion of 10 (60 mg; 0.15 mmol) was dissolved in 10 mL anhydrous THF with stirring and cooled to 4° C. under $N_2$. A portion of PBr₃ (21 μL, 0.22 mmol) was slowly added under $N_2$ and the reaction was kept at 4° C. for 2 h. The solvent was evaporated to yield a yellow solid. The highly reactive brominated intermediate was transferred to a 50-mL centrifuge tube with trifluoroacetic acid. TFA was dried under $N_2$. To the residue, dry diethylether was added, cooled with liquid $N_2$, and centrifuged to obtain a yellow solid which was washed with dry ether 3 times. 11 obtained as a precipitate was taken forward for the next step without further purification. HRMS (m/z): calculated for [MH+] $C_{12}H_{15}BrN_2O_3$ 315.0339 and 317.0320, observed 315.0344 and 317.0324.

Glu-DTC: 11 obtained from above was suspended in dry acetonitrile and Na diethyl dithiocarbamate trihydrate was added and stirred for 2 h. The precipitate obtained was filtered and washed with ether. The solid obtained was purified by HPLC using a linear gradient running from 80%-2% $H_2O$: acetonitrile containing 0.1% TFA over 40 min to yield Glu-DTC (8.5 mg; 15.2% yield). $^1$H NMR (400 MHz, DMSO-d6) δ 10.52 (s, 1H), 7.56 (d, J=8.2 Hz, 2H), 7.28 (d, J=8.3 Hz, 2H), 4.41 (s, 2H), 3.96 (q, J=7.0 Hz, 2H), 3.71 (q, J=7.1 Hz, 2H), 3.28 (t, J=6.4 Hz, 1H), 1.95 (q, J=7.5 Hz, 2H), 1.18 (td, J=6.9, 4.9 Hz, 6H). $^{13}$C NMR (125 MHz, DMSO-d6) δ 193.6, 170.9, 170.0, 138.6, 130.3, 129.5, 119.1, 53.5, 49.0, 46.5, 40.7, 32.9, 27.0, 12.4, 11.4. HRMS (m/z): calculated for [MH+] $C_{21}H_{32}N_2O_6$ 384.1410, observed 384.1402.

In Vitro Release of the GGT Cleavable Prodrug

The design for a γ-glutamyl prodrug uses γ-glutamate (γ-Glu) as a selective recognition and trigger moiety for prochelator activation. In principle, this strategy leverages two different processes to differentially target cancer cells: their overexpression of GGT and their altered copper biology. To maintain the required γ-glutamyl amide bond for GGT recognition, DTC was conjugated to γ-glutamate via a self-immolative p-aminobenzyl (PAB) linker. Once the amide bond is hydrolyzed by GGT, 1,6 benzyl elimination of the PAB linker is expected to release DTC specifically in the vicinity of cells expressing GGT, where it is free to bind available metal ions (Scheme 5).

Scheme 5: GGT enzyme cleavage products

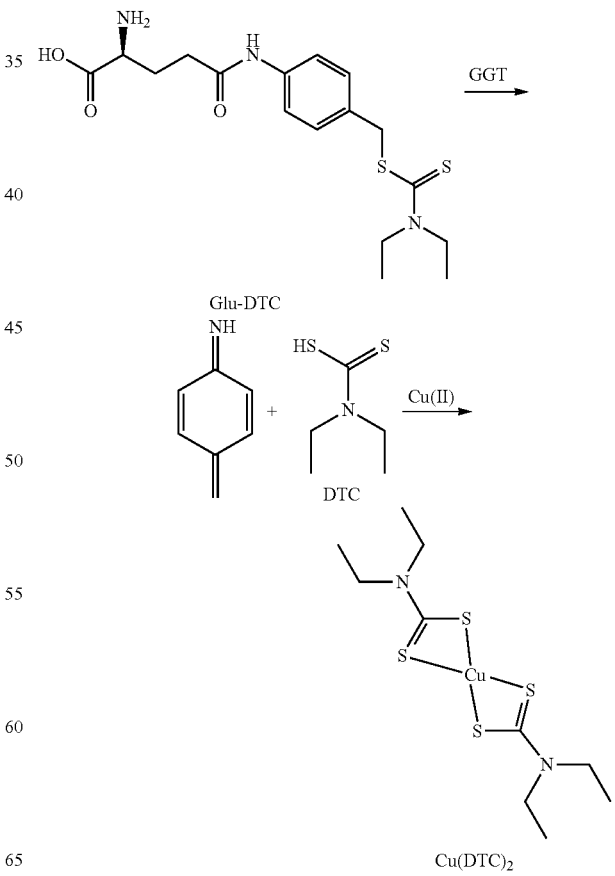

Figure 9A:
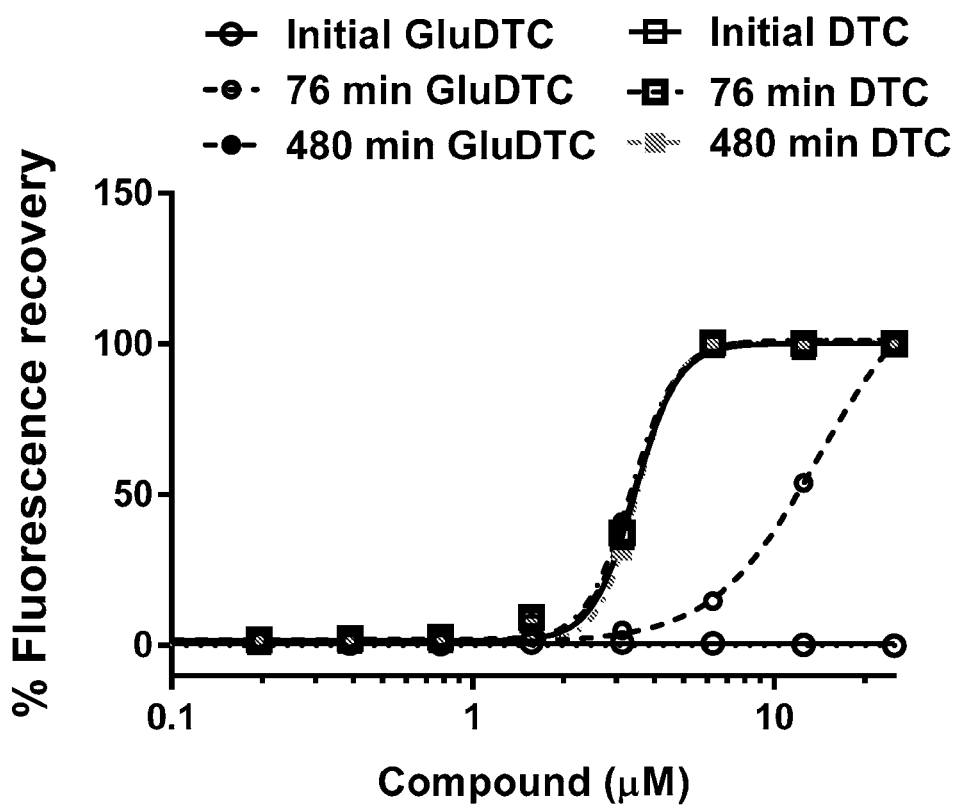
FIG. 9A shows the % fluorescence recovered of calcein plotted against concentration of DTC and Glu-DTC. Plots at different timepoint of GGT exposure in accordance with one embodiment of the present disclosure.
Figure 9B:
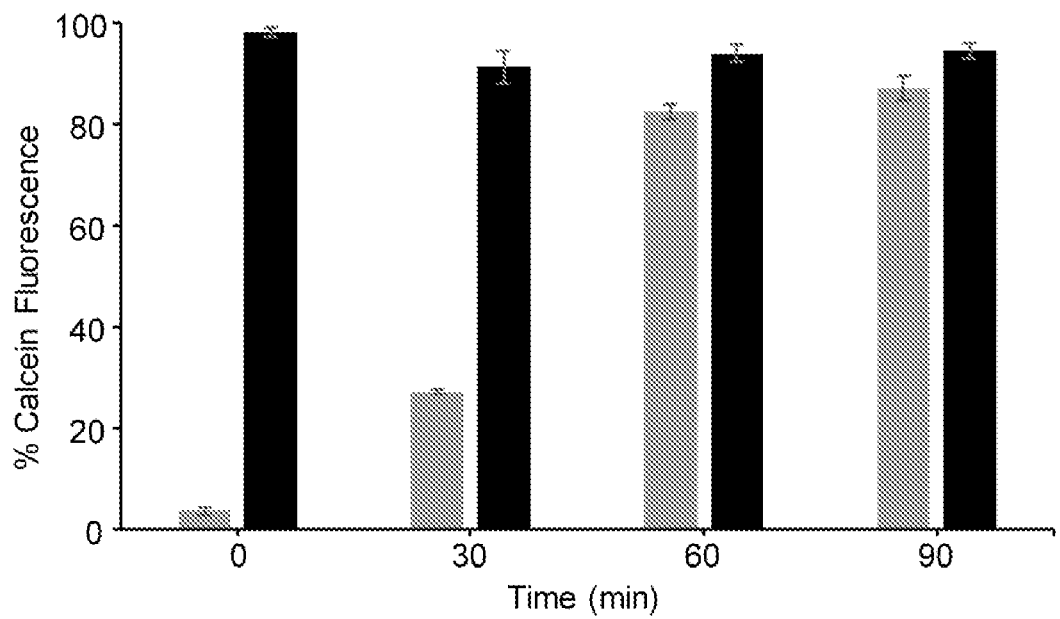
FIG. 9B shows the results of copper-calcein competition assay showing recovery of calcein fluorescence as a function of added chelator or prochelator in the presence of GGT enzyme over time. Solutions contained 1 μM CuSO4, 1 μM calcein, 20 U/L of GGT enzyme, and 12.5 μM of either Glu-DTC (grey) or DTC (black) in PBS buffer pH 7.4 with 1 mM Gly-Gly; 37° C.
Figure 14:
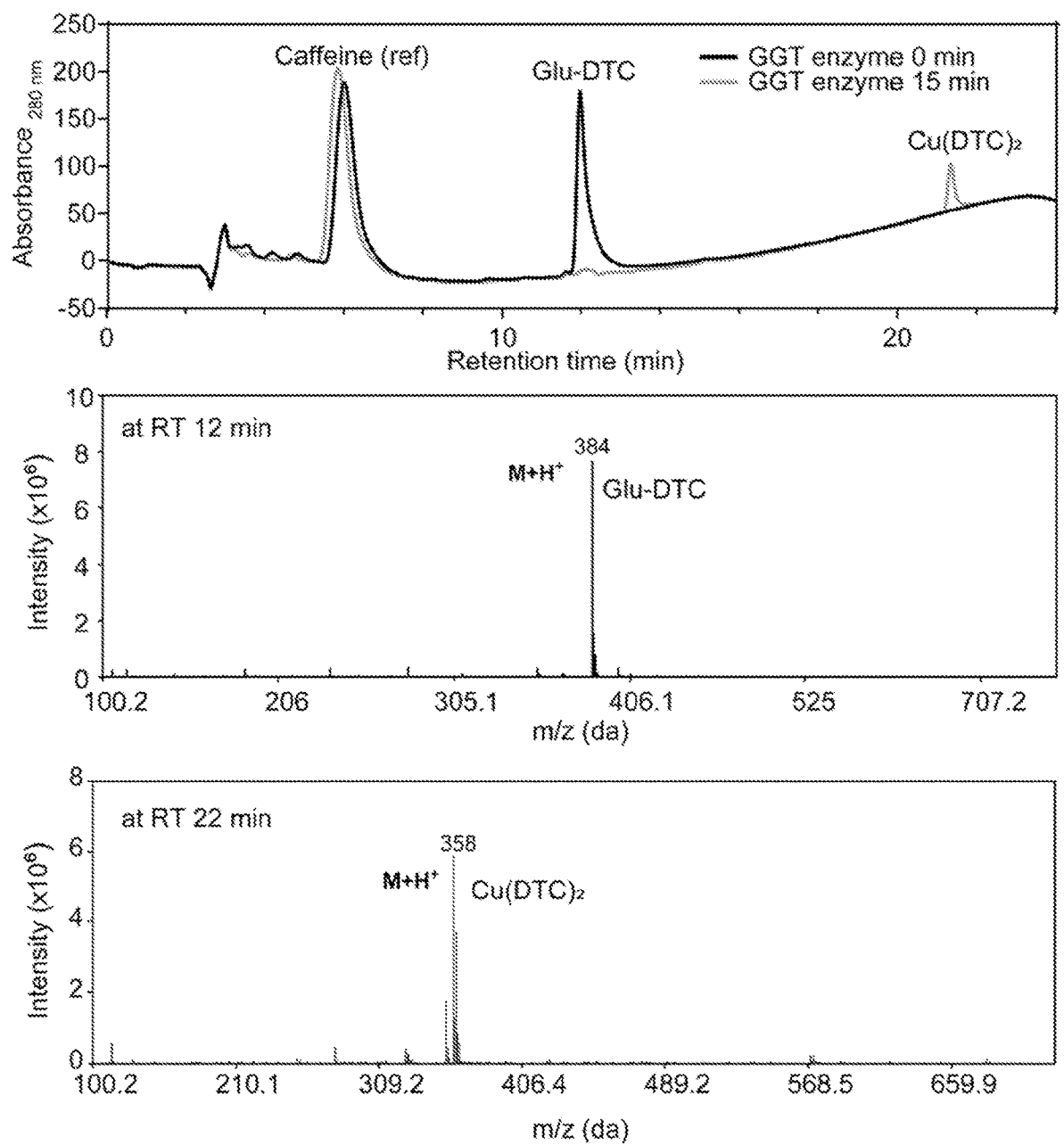
FIG. 14 shows an LC-MS trace (top) of Glu-DTC observed at 280 nm absorbance before and after exposure to 100 U/L of GGT enzyme for 15 min. A gradient of 10% Solvent A (90:10 $H_2O$:MeOH with 0.1% formic acid) to 90% Solvent B (90:5:5 ACN:H2O:MeOH with 0.1% formic acid) was run for 25 minutes through C18 column followed by 100% solvent B. A mass spectrum at retention time 12 min (middle) displays the mass of Glu-DTC. A mass spectrum at retention time 22 min (bottom) displays the mass of $Cu(DTC)_2$ complex.

A competitive calcein assay was used to test the hypothesis that masking DTC as a prodrug impedes its ability to bind to copper. Calcein is a fluorophore for which fluorescence is quenched upon binding to Cu(II). A Cu(II) chelator competes with calcein for Cu(II) binding, thus restoring its fluorescence. While DTC could restore the fluorescence, the prochelator Glu-DTC could not compete with calcein for Cu binding. However, exposure of Glu-DTC to the GGT enzyme, resulted in recovery of calcein fluorescence over time (FIG. 9A and FIG. 9B), indicating that the reaction with GGT released a product capable of chelating Cu(II). Indeed, the presence of $Cu(DTC)_2$ as a product was confirmed by HPLC and mass spectral analysis of solutions following exposure of Glu-DTC to GGT enzyme in the presence of Cu(II) (FIG. 14). Together, these results validate the concept of masking metal-chelating competency in Glu-DTC and support our molecular mechanism that GGT activation induces DTC release.

Figure 15A:
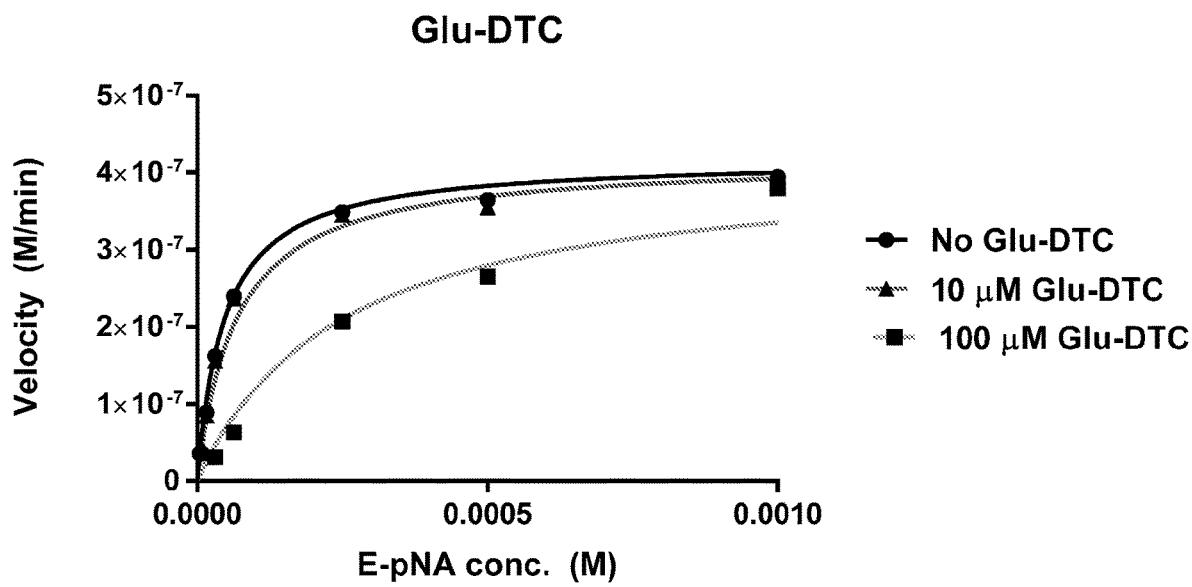
FIG. 15A, FIG. 15B and FIG. 15C show the results from GSH competition experiments. Determination of GGT $K_i$ values for Glu-DTC (FIG. 15A), DTC (FIG. 15B), and GSH (FIG. 15C) were determined by monitoring p-nitroaniline release (Abs 405 nm) versus the colorimetric substrate E-pNA.
Figure 15B:
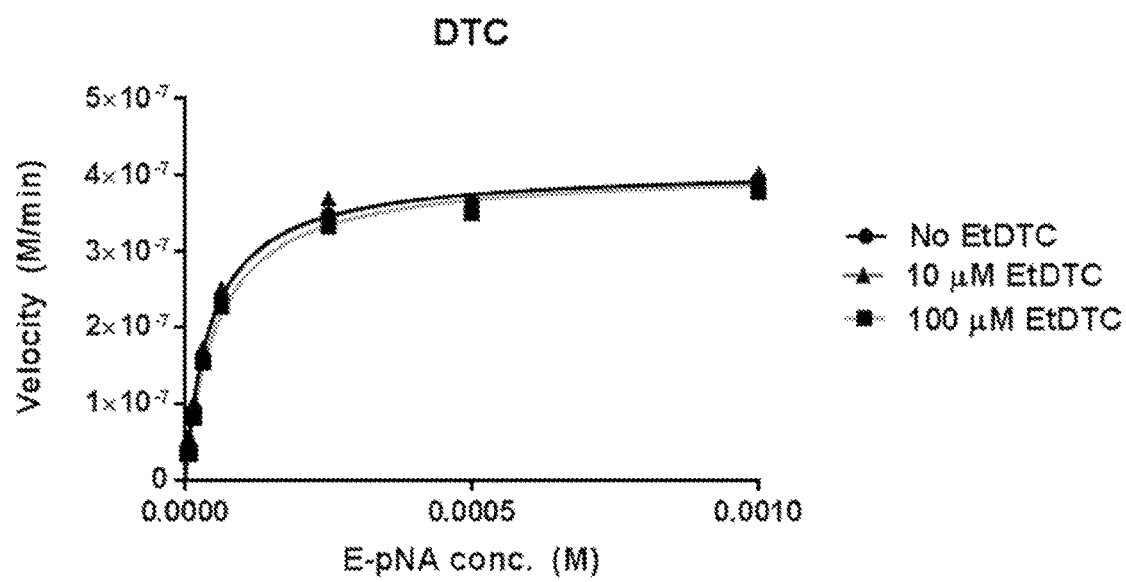
Figure 15C:
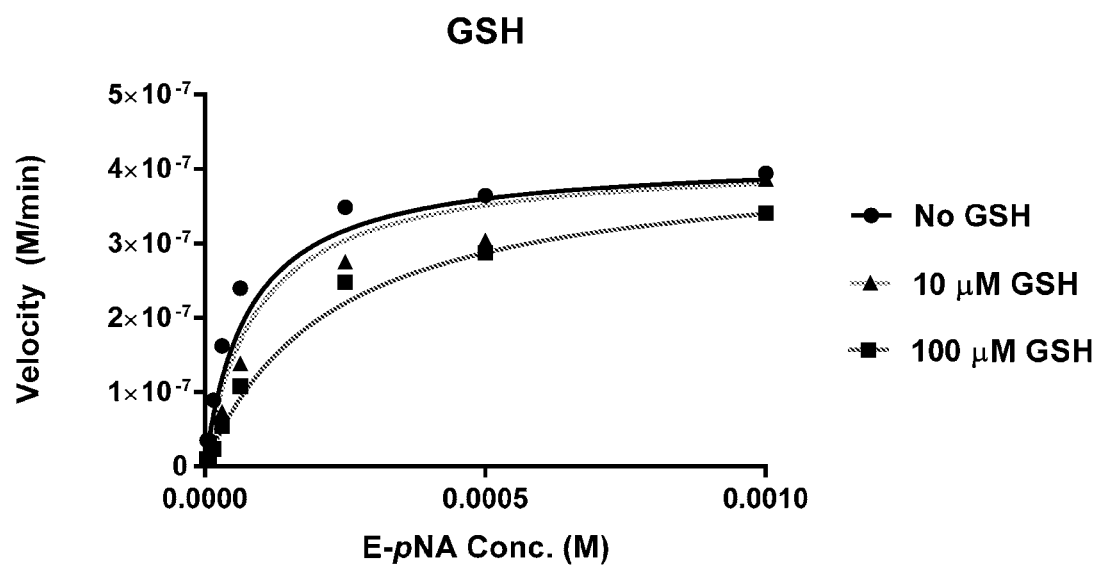

To probe the reactivity of Glu-DTC in comparison to the enzyme's natural substrate GSH, competition experiments were conducted against the colorimetric substrate L-glutamic acid γ-(p-nitroanilide) [E-pNA]. The colorimetric assay involves monitoring p-nitroaniline release by absorbance at 405 nm upon reaction of the probe substrate E-pNA with GGT in the presence of an inhibiting substrate, either Glu-DTC (FIG. 15A) or GSH (FIG. 15C). The $K_i$ for glutathione (GSH) was found to be 99±7 µM (under the experimental conditions: PBS, pH 7.4, 1 mM GlyGly) which falls in similar range as reported earlier (73±6 µM). With a $K_i$ of 23±5 µM, Glu-DTC was found to have greater affinity for GGT than glutathione. This finding shows that Glu-DTC should be preferentially cleaved over GSH. The assay also confirmed that the presence of DTC does not affect enzyme kinetics.

Biological Activity of the GGT Cleavable Prodrug

Prostate cancer cell lines are reported to overexpress GGT. In initial experiments three cell lines, two prostate cancer lines and one prostate normal cell line, with varying GGT expression levels were chosen for the preliminary study. To detect the activity of GGT in different cell lines L-glutamic acid γ-(p-nitroanilide) [E-pNA] was used as a colorimetric indicator of GGT activity. GGT releases p-nitroaniline from the above substrate which can be monitored via change in absorbance at 405 nm. Based on the p-nitroanilide assay, LNCaP cells expressed 1.6 U/L GGT while PC3 cells expressed 0.3 U/L GGT. Prostate normal cell lines expressed <0.1 U/L of GGT. Glu-DTC displayed an $IC_{50}$ of 0.76 µM after 24 h against LNCaP cells in the presence of 1 µM supplemental Cu(II) added to the growth medium. In PC3 cells the $IC_{50}$ was about 12 µM. Glu-DTC did not show much toxicity in PWR-1E within the tested concentration of 10 µM. The $IC_{50}$ follows the opposite trend of GGT expression, i.e. the higher the GGT expression level the lower the $IC_{50}$. This result confirms that a toxic component is selectively released only upon exposure to GGT, thus preventing activation in normal cells.

Figure 11:
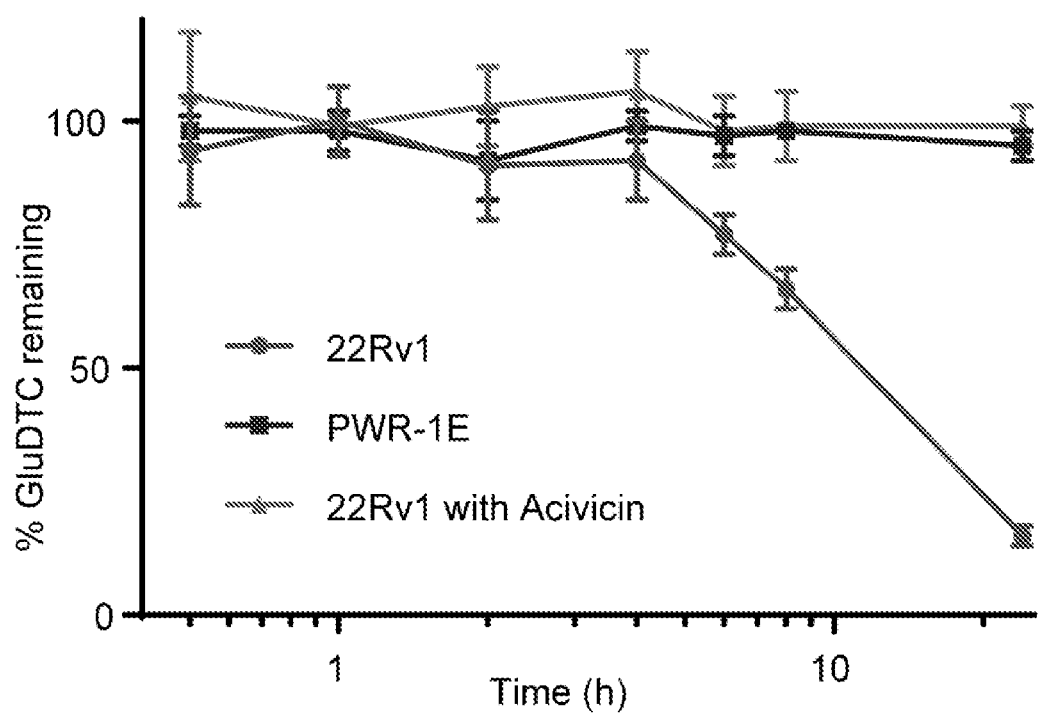
FIG. 11 shows the levels of intact Glu-DTC observed by HPLC analysis of supernatants of cells incubated with 100 µM Glu-DTC for 24 h at 37° C. in medium supplemented with 1 mM GlyGly. Glu-DTC depletion was observed over 24 h in 22Rv1 cells, whereas Glu-DTC levels were unchanged in 22Rv1 treated with GGT-inhibitor Acivicin or in PWR-1E cells.

A more exhaustive study was undertaken to test the stability, anticancer activity and GGT activity across a series of cell lines. To test the stability of Glu-DTC and the selectivity of its activation in human cells, an HPLC assay was performed on cell culture supernatants after incubation with Glu-DTC. Representative examples from two cell lines: 22Rv1, an aggressive prostate cancer cell line that tested positively for GGT activity, and PWR-1E, a normal prostate epithelial line which tested negatively for GGT activity under these conditions (vide infra) are shown in FIG. 11. Exposure of 100 µM Glu-DTC to 22Rv1 cells caused a significant loss of detectable Glu-DTC. Co-exposure with the GGT inhibitor Acivicin, however, completely reversed this trend and Glu-DTC was found to be stable for at least 24 h. The level of intact Glu-DTC was also found to be unchanged in the GGT(-) PWR-1E cells. Together, these results provide evidence for the selectivity of the prodrug for GGT activation and its stability against non-specific degradation processes in cellular environments.

Figure 12:
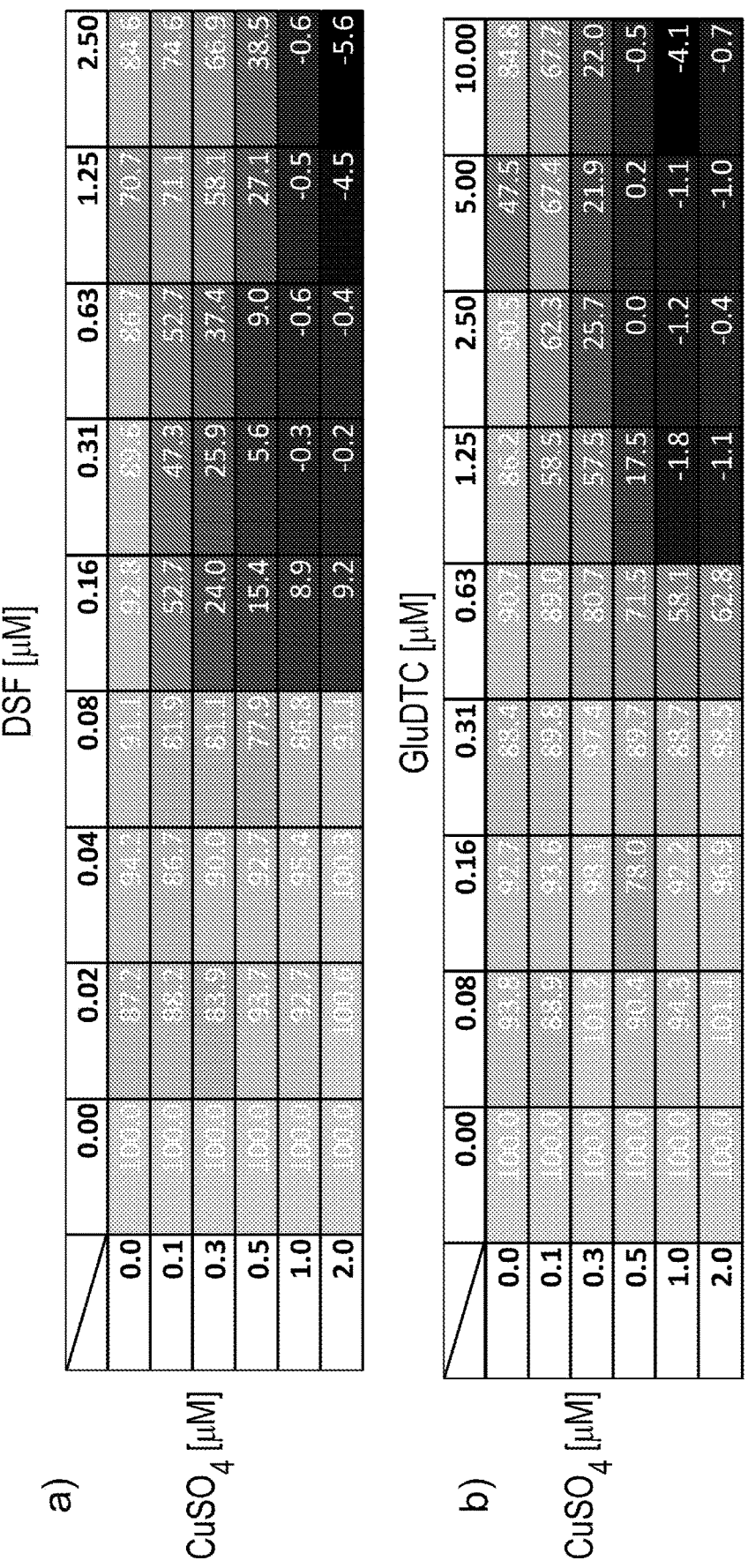
FIG. 12 shows checker board assays with varying copper concentrations (0-2 µM) and DSF (0-2.5 µM) and Glu-DTC (0-10 µM) concentrations. % viability is shown. The results range from more viability to less viability.
Figure 13A:
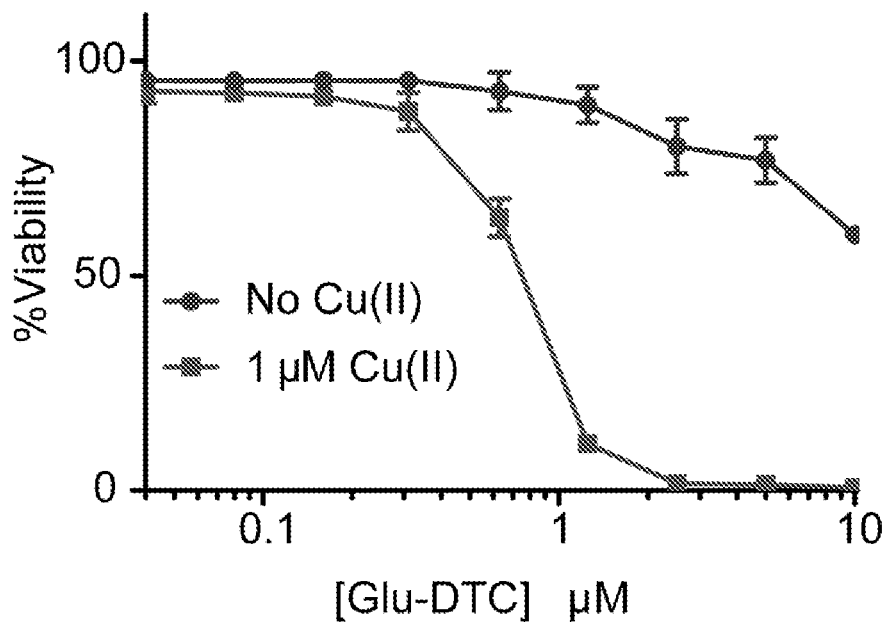
FIG. 13A and FIG. 13B show representative dose-response curves for Glu-DTC with and without supplemental $CuSO_4$ for prostate cancer LNCaP (A) and prostate normal epithelial PWR-1E cell lines (B), as determined by a resazurin viability assay measured at 24 h.
Figure 13B:
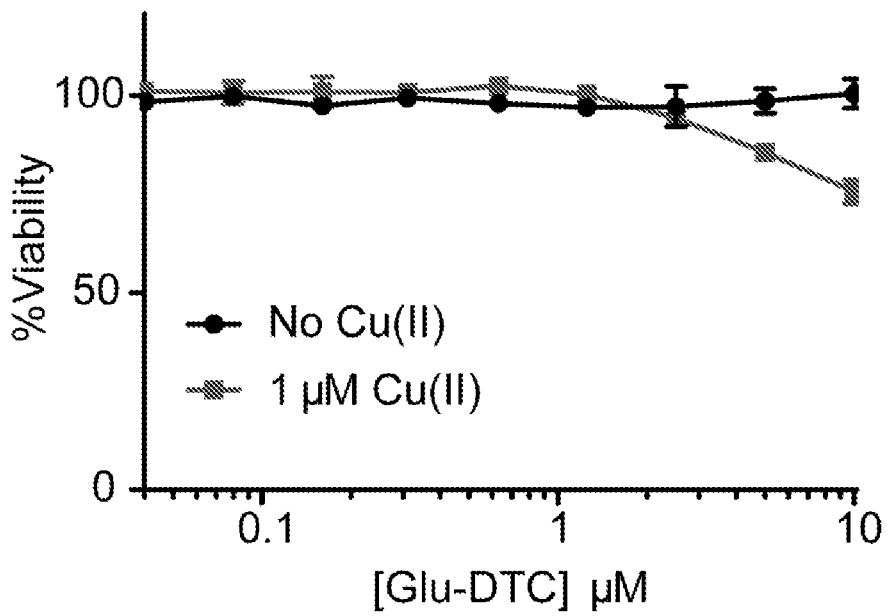

In order to evaluate the potential anticancer activity of Glu-DTC, the prodrug and DSF were tested for their ability to inhibit cell growth of aggressive prostate cancer cells 22Rv1, LNCaP, and PC3, as well as PWR-1E prostate epithelial cells, and MCF-7 breast cancer cells. Because Cu is known to be required for disulfiram's antiproliferative activity, checkerboard assays were performed to establish the Cu dependence of DSF and Glu-DTC for inhibition of cell viability under our conditions. Pilot studies in 22Rv1 cells revealed that antiproliferative activity of both DSF and Glu-DTC required as low as 300 nM Cu(II) added to the growth medium, with 1 µM Cu providing a robust response for both compounds (FIG. 12). Subsequent studies were therefore conducted in medium supplemented with 1 µM CuSO4. Representative dose-response curves for Glu-DTC with and without supplemental Cu are shown for LNCaP cells (FIG. 13A) and for PWR-1E cells (FIG. 13B), with $IC_{50}$ values for all cell lines in the Cu-supplemented condition shown in FIG. 13C (right bars). The data were collected at 24 h, where the difference in the antiproliferative activity of Glu-DTC across the cell lines is already evident, with $IC_{50}$ values ranging from 800 nM in 22Rv1 and LNCaP cancer cell lines to over 15 µM in normal prostate PWR-1E cells. The difference in antiproliferative activity of Glu-DTC across these cell lines narrows but persists after 72 h continuous exposure, with $IC_{50}$ values ranging from 300 nM in 22Rv1 to 1.5 µM in PWR-1E cells. (Table 2). In contrast, DSF was robustly effective across all cell lines, with $IC_{50}$ values in the 40-150 nM range at 72 h, consistent with prior studies (Table 2). Since DSF is a dimer of DTC, the $IC_{50}$ per monomer is therefore 80-300 nM at 72 h.

TABLE 2

| | IC50 (µM) with 1 µM CuSO4 in different cell lines arranged in the order of decreasing GGT activity | | | | |
|---|---|---|---|---|---|
| Cell line | Aggressive prostate cancer; 22Rv1 | Prostate Cancer, LNCaP | Breast Cancer, MCF-7 | Prostate Cancer, PC-3 | Prostate normal, PWR-1E |
| Disulfiram at 24 h | 0.072 ± 0.01 | 0.13 ± 0.02 | 0.18 ± 0.01 | 0.07 ± 0.01 | 0.08 ± 0.02 |
| Glu-DTC at 24 h | 0.76 ± 0.09 | 0.62 ± 0.04 | 1.7 ± 0.1 | 5.5 ± 0.1 | 16.8 ± 4.4 |
| Disulfiram at 72 h | 0.092 ± 0.005 | 0.14 ± 0.01 | 0.047 ± 0.002 | 0.057 ± 0.01 | 0.07 ± 0.01 |

TABLE 2-continued

| | IC50 (μM) with 1 μM CuSO$_4$ in different cell lines arranged in the order of decreasing GGT activity | | | | |
|---|---|---|---|---|---|
| Cell line | Aggressive prostate cancer; 22Rv1 | Prostate Cancer, LNCaP | Breast Cancer, MCF-7 | Prostate Cancer, PC-3 | Prostate normal, PWR-1E |
| Glu-DTC at 72 h | 0.29 ± 0.11 | 0.5 ± 0.09 | 0.48 ± 0.04 | 1.32 ± 0.25 | 1.55 ± 0.02 |

Figure 13C:
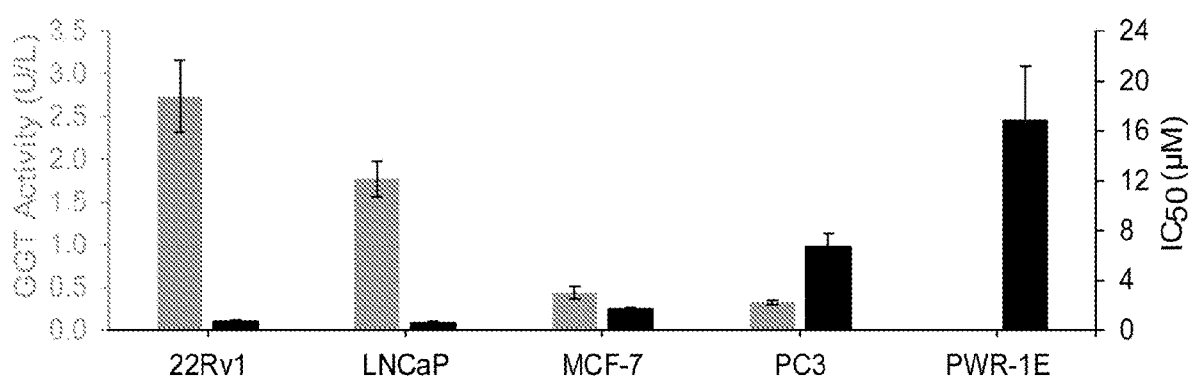
FIG. 13C shows GGT activity (left bar) measured by E-pNA colorimetric assay, and $IC_{50}$ values of Glu-DTC (right bar) across multiple cell lines in FBS-free medium with 1 µM $CuSO_4$ for 24 h. Antiproliferative activity of Glu-DTC correlates with levels of GGT enzyme activity.
Figure 16A:
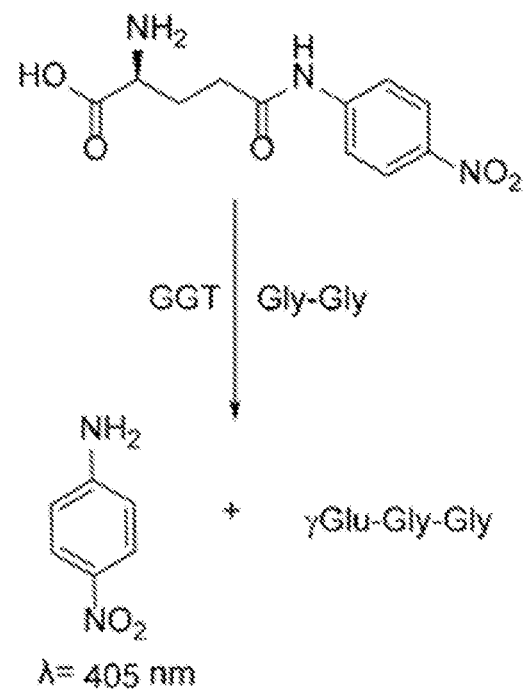
FIG. 16A shows a scheme for p-nitroaniline release from γ-glutamate p-nitroanilide by GGT enzyme.
Figure 16B:
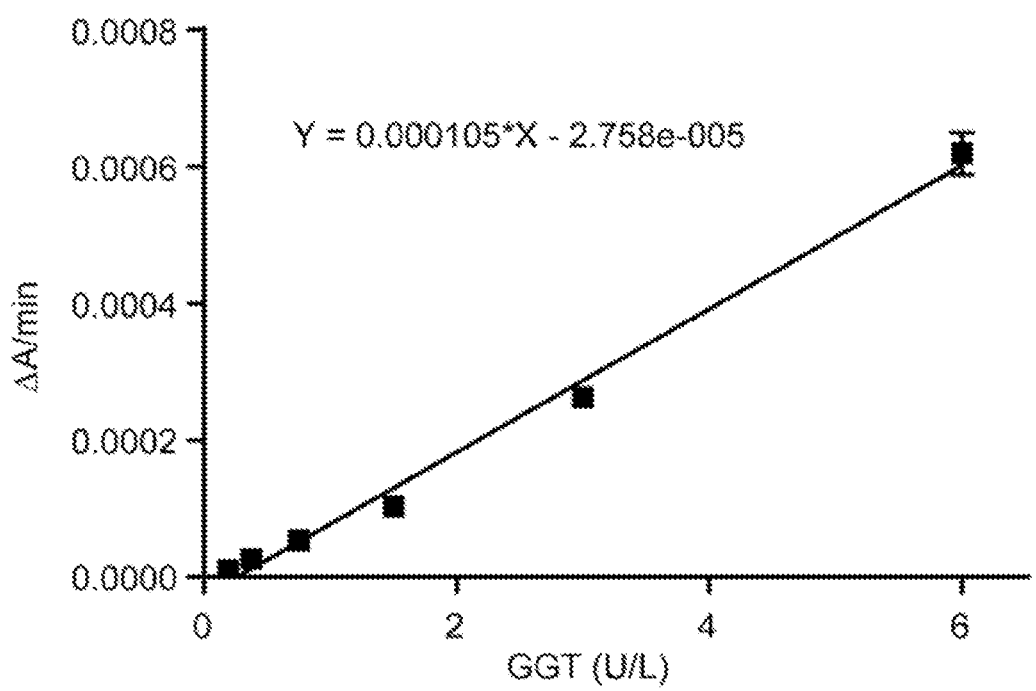
FIG. 16B shows the standard curve for the determination of GGT activity.
Figure 16C:
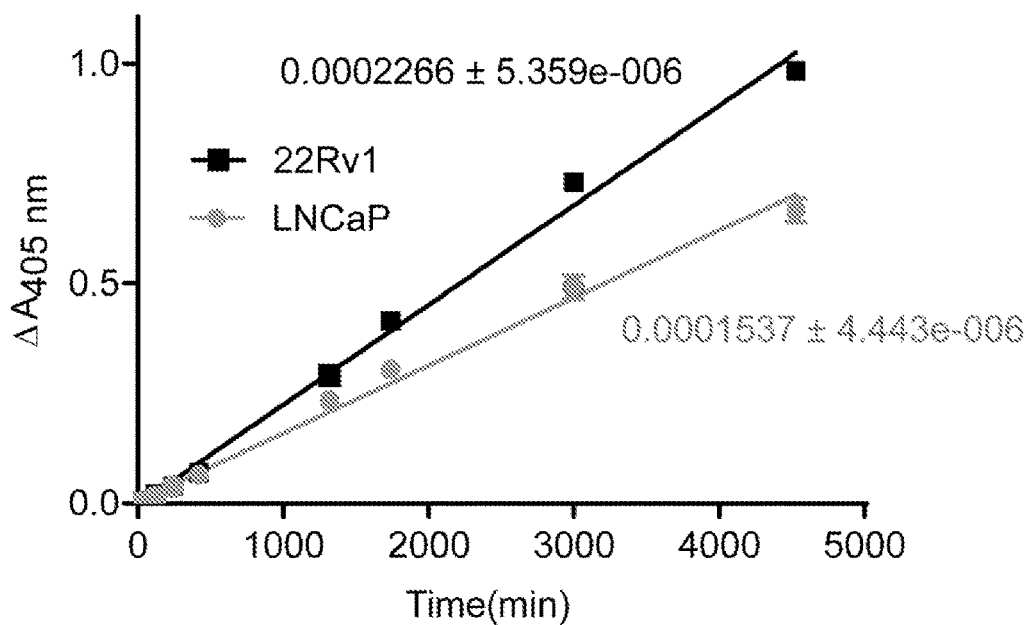
FIG. 16C and FIG. 16D show representative plots of change in absorbance vs time for 22Rv1 (squares, FIG. 16C), LNCaP (circles, FIG. 16C), MCF-7 (squares, FIG. 16D), PC-3 (triangles, FIG. 16D), and PWR-1E (circles, FIG. 16D). Slope obtained through linear fit mentioned in the plots. The obtained slope is interpolated in standard curve in FIG. 16B to obtain GGT activity. PWR-1E data points did not fit in a straight line but demonstrated change in absorbance around 72 h.
Figure 16D:
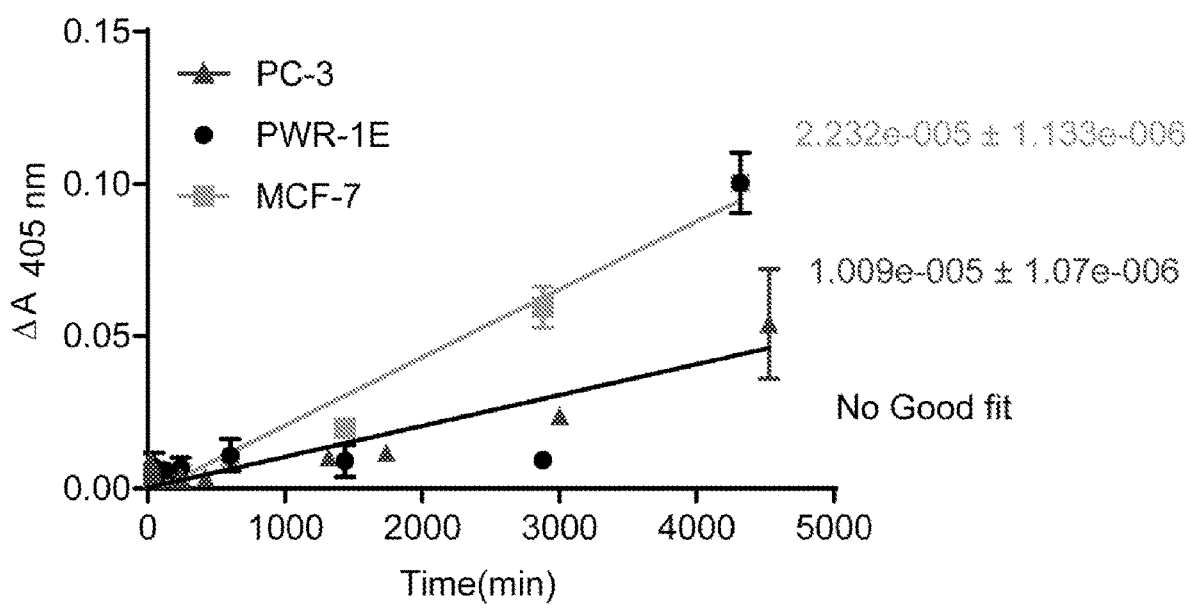

In parallel to the cell viability assays, the GGT activity of each cell line was measured by using the colorimetric test substrate E-pNA (FIG. 16A). The aggressive prostate cancer lines 22Rv1 and LNCaP showed high GGT activity (FIG. 16C), consistent with expectations of over-active GGT activity in these cells (FIG. 13C, left bars). In contrast, MCF-7 and PC3 revealed measurable but lower activity, while PWR-1E showed no detectable activity at 24 h, with some activity emerging by 72 h (FIG. 16D). The emergence of GGT activity over long incubation times for these cells explains the reduction in IC$_{50}$ of Glu-DTC in PWR-1E cells at 72 h (Table 2). Importantly, the trend in GGT activity correlates with antiproliferative efficacy of Glu-DTC: the more active the cell line, the lower the IC$_{50}$ for Glu-DTC.

Figure 10A:
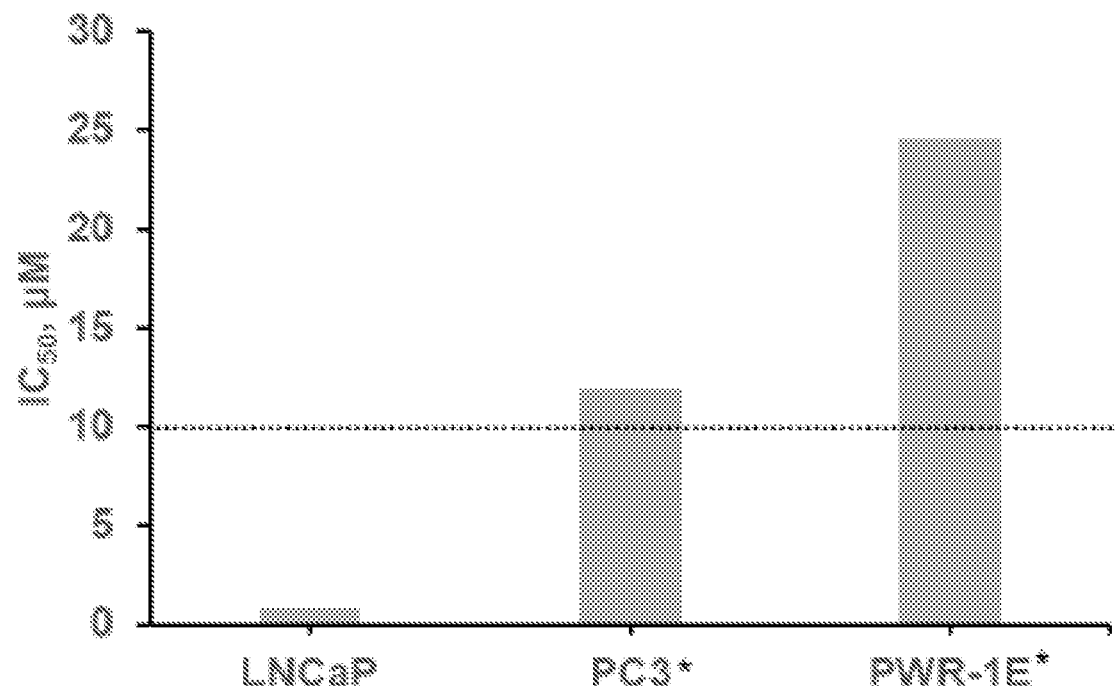
FIG. 10A plots $IC_{50}$ values of Glu-DTC in different cell lines at 24 h. Dotted line represent maximum Concentration tested. * IC50 values obtained by extrapolation of the curve.
Figure 10B:
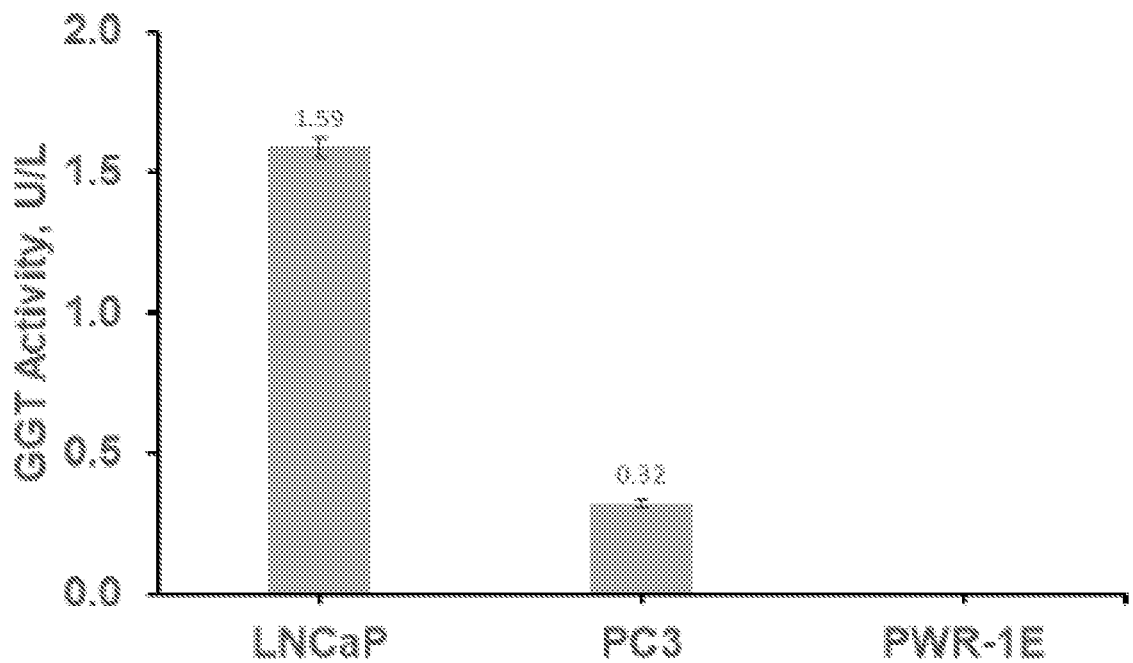
FIG. 10B shows GGT activity levels in different cell lines in accordance with one embodiment of the present disclosure.

Thus, a prodrug of DTC (Glu-DTC) activated only in the presence of GGT has been developed. Cancer specific activation of Glu-DTC could prevent the off-target activity of DTC and thus has potential as a targeted therapeutic (FIG. 10).

Example 4: Folate Receptor Targeted Prodrug

Synthesis of Folic Acid Conjugated Prodrug FA-DTC

Scheme 6 describes the synthesis of a folic acid conjugated prodrug. The cysteine containing peptide was synthesized via solid phase peptide synthesis. Folic acid was coupled to the peptide on resin using PyBOP. The folic acid conjugated peptide was cleaved and purified. The cysteine in the folic acid conjugated peptide was activated by forming a mixed disulfide with 2-mercaptopyridine. Reacting Compound 13 with sodium diethyldithiocarbamate lead to disulfide exchange and formation of desired FA-DTC construct.

Scheme 6: Synthesis of FA-DTC conjugate.

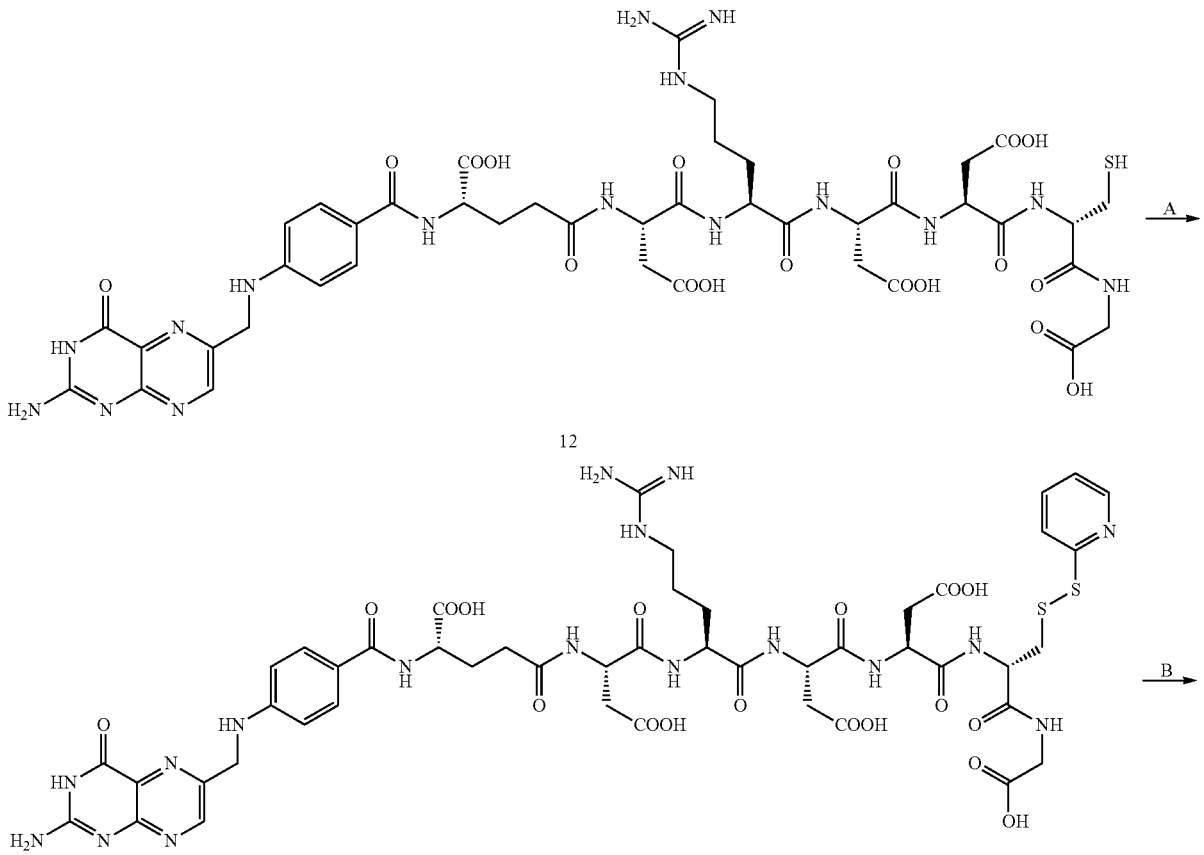

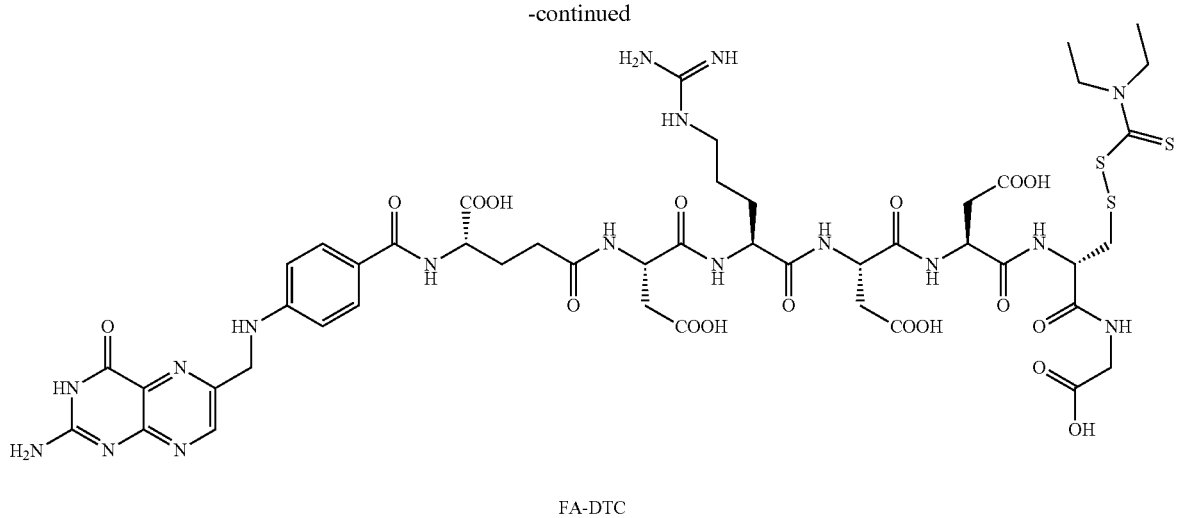

FA-DTC

A) Aldrithiol, MeOH, 12 h B) Na diethyldithiocarbamate, MeOH, 12 h.

Example 5: Prostate Specific Membrane Antigen (PSMA) Targeted Prodrug

Synthesis of DUPA Conjugated Prodrug DUPA-DTC

Scheme 7 describes the synthesis strategy for DUPA-DTC. DUPA is synthesized from carbinyldiimidazole. The carbonyl diimidazole was monosubstituted with tertbutyl protected glutamate by slow addition to obtain compound 15. Second substitution was done with α-tertbutyl-γ-benzyl protected glutamate to obtain 16. Benzyl deprotection was achieved by reductive elimination via in situ generation of $H_2$. DUPA moiety thus obtained can be further used to couple to the peptide via solid phase peptide synthesis. Cleavage of peptide from resin can also deprotect the tert-butyl groups from the DUPA moiety. DTC coupling could be achieved using aldrithiol, similar to FA-DTC synthesis strategy.

Scheme 7: Synthesis strategy for DUPA-DTC

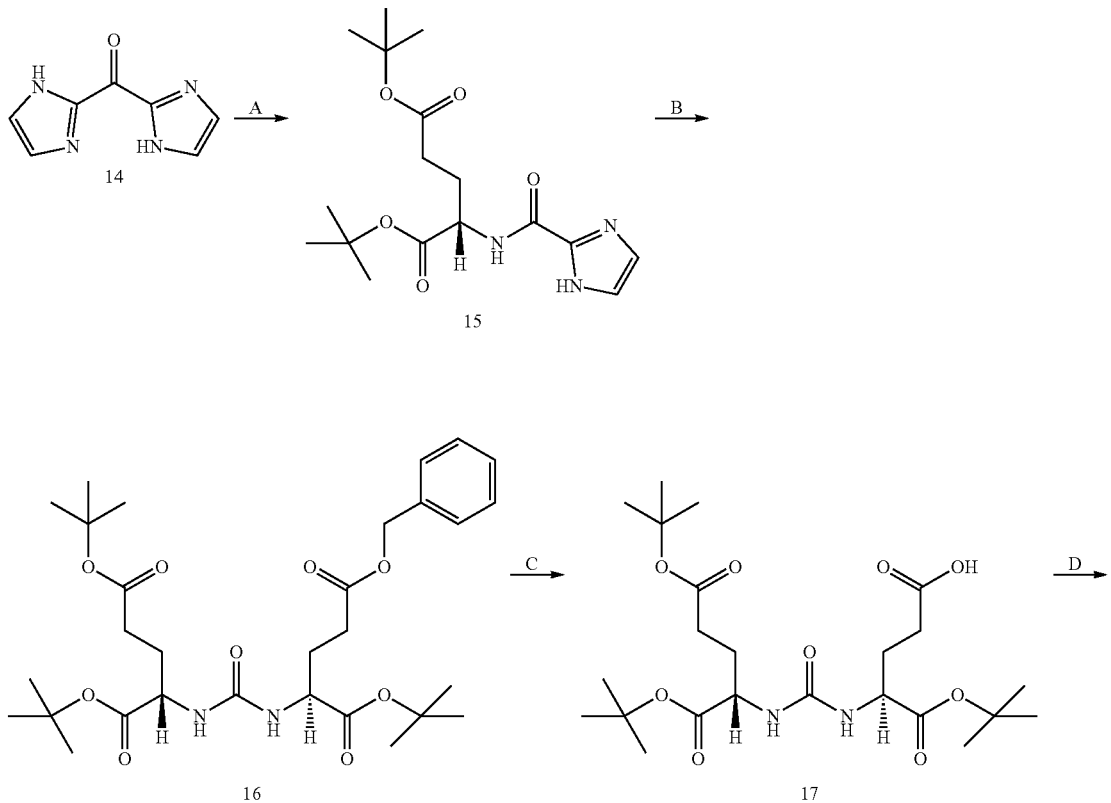

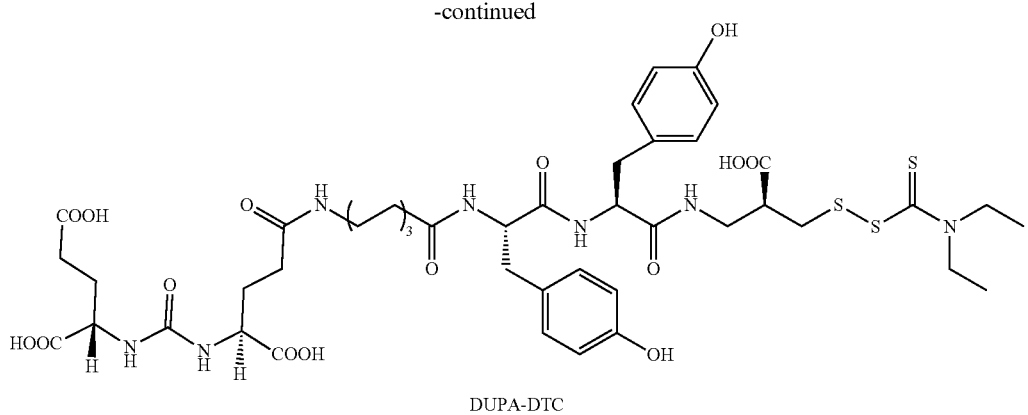

DUPA-DTC

The foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

For reasons of completeness, various aspects of the invention are set out in the following numbered clauses:

Clause 1. A compound of formula (I),

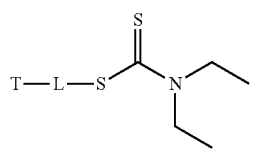

(I)

or a pharmaceutically accept salt, amide, or ester thereof, wherein

T is a targeting moiety for a cell; and

L is a linker.

Clause 2. The compound of clause 1, or a pharmaceutically accept salt, amide, or ester thereof, wherein T is a substrate of an enzyme of the cell, or T binds to a protein of the cell.

Clause 3. The compound of any one of clauses 1-2, or a pharmaceutically accept salt, amide, or ester thereof, wherein T is an amino acid, a peptide,

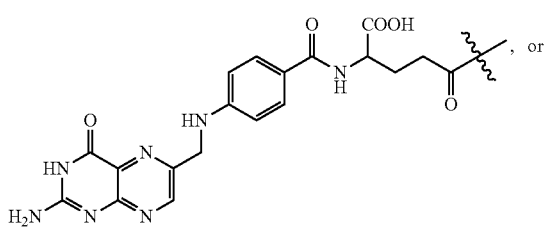

, or

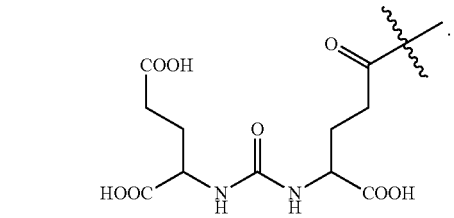

.

Clause 4. The compound of any one of clause 1-3, or a pharmaceutically accept salt, amide, or ester thereof, wherein T is an amino acid or a peptide having 2-10 amino acids.

Clause 5. The compound of any one of clause 1-4, or a pharmaceutically accept salt, amide, or ester thereof, wherein T is a peptide, which is a substrate of Prostate Specific Antigen (PSA).

Clause 6. The compound of any one of claims 1-5, or a pharmaceutically accept salt, amide, or ester thereof, wherein T is

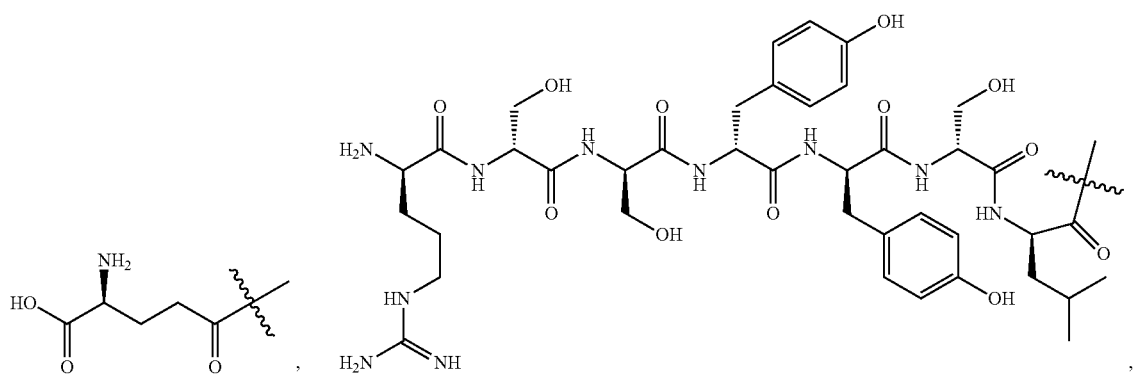

,

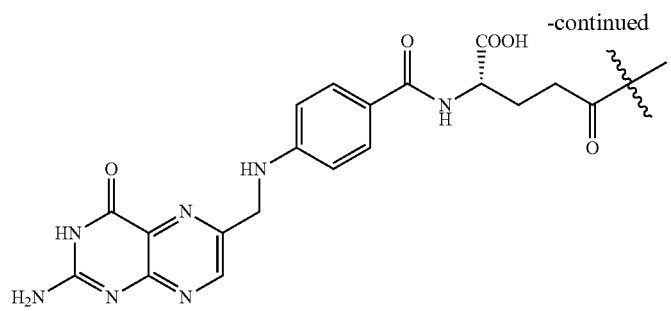

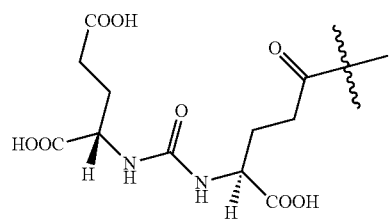, or

Clause 7. The compound of any one of clause 1-6, or a pharmaceutically accept salt, amide, or ester thereof, wherein
L is

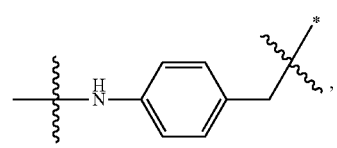

W, or —NH(CH$_2$)$_n$C(O)—W;
W is

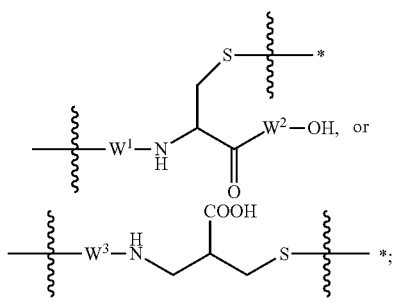

* indicates the attachment to

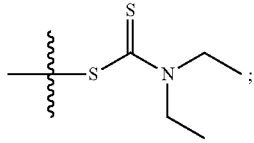 [SMILES: *SC(=S)N(CC)CC]

W$^1$, W$^2$, and W$^3$ are each independently a bond, an amino acid, or a peptide; and
n is 1, 2, 3, 4, 5, 6, 7, 8, 9, or 10.

Clause 8. The compound of any one of clause 1-7, or a pharmaceutically accept salt, amide, or ester thereof, wherein L is

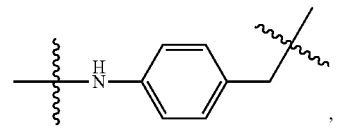

-continued

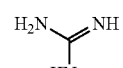

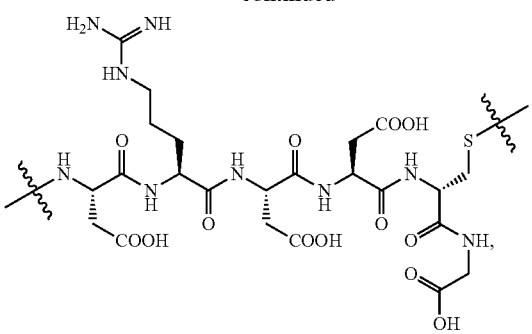, or

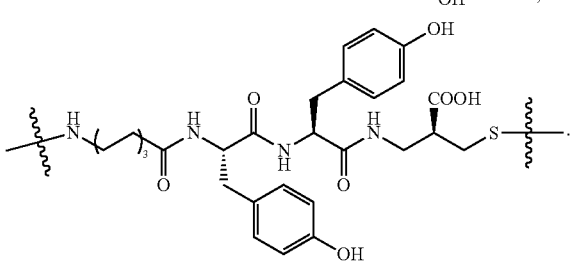.

Clause 9. The compound of any one of clause 1-8, or a pharmaceutically accept salt, amide, or ester thereof, wherein T is an amino acid or a peptide having 2-10 amino acids, and L is

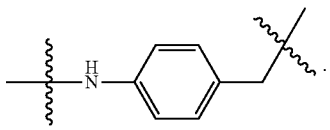 [SMILES: *Cc1ccc(N*)cc1]

Clause 10. The compound of any one of clause 1-8, or a pharmaceutically accept salt, amide, or ester thereof, wherein T is

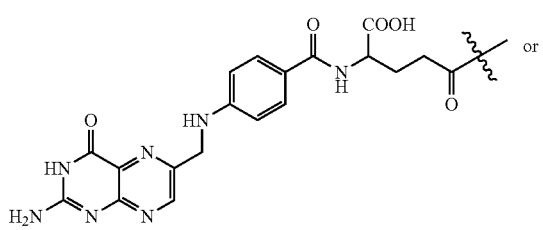 or

-continued

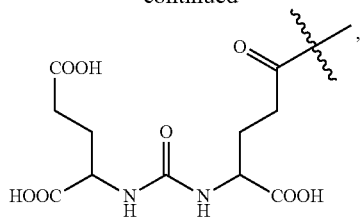

and L is W or —NH(CH$_2$)$_n$C(O)—W.

Clause 11. The compound of any one of clause 1-8 and 10, or a pharmaceutically accept salt, amide, or ester thereof, wherein T is

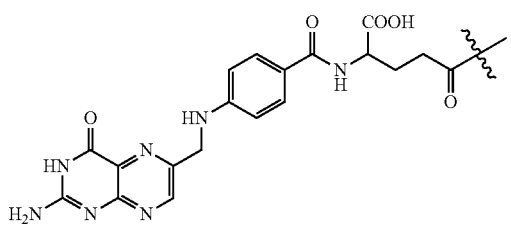 [SMILES: *C(=O)CCC(NC(=O)c1ccc(NCc2cnc3nc(N)[nH]c(=O)c3n2)cc1)C(=O)O]

and L is W.

Clause 12. The compound of clause 11, or a pharmaceutically accept salt, amide, or ester thereof, wherein W is

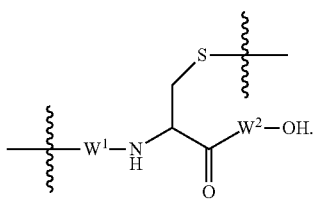

Clause 13. The compound of clause 12, or a pharmaceutically accept salt, amide, or ester thereof, wherein W$^1$ and W$^2$ are each independently an amino acid or a peptide having 2-8 amino acids.

Clause 14. The compound of any one of clause 1-8 and 10, or a pharmaceutically accept salt, amide, or ester thereof, wherein T is

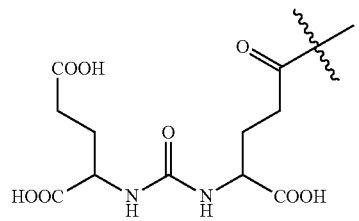 [SMILES: *C(=O)CCC(NC(=O)NC(CCC(=O)O)C(=O)O)C(=O)O]

and L is —NH(CH$_2$)$_n$—C(O)—W.

Clause 15. The compound of clause 14, or a pharmaceutically accept salt, amide, or ester thereof, wherein W is

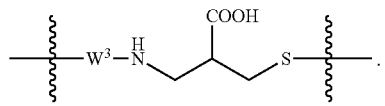

Clause 16. The compound of clause 15, or a pharmaceutically accept salt, amide, or ester thereof, wherein W$^3$ is an amino acid or a peptide having 2-6 amino acids.

Clause 17. The compound of clause 1, selected from the group consisting of

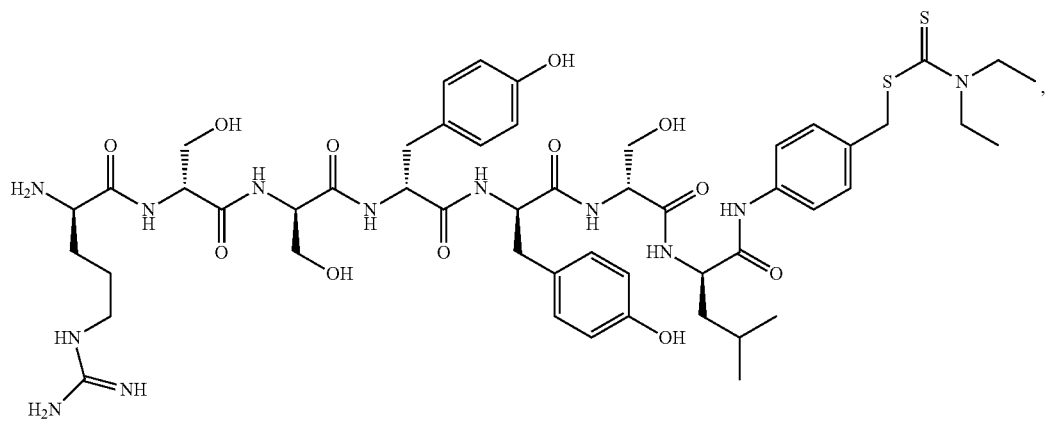

(PSA-DTC)

-continued

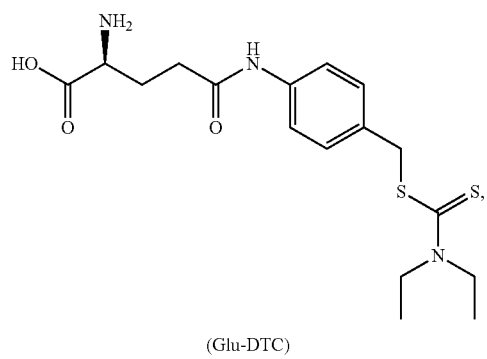
(Glu-DTC)

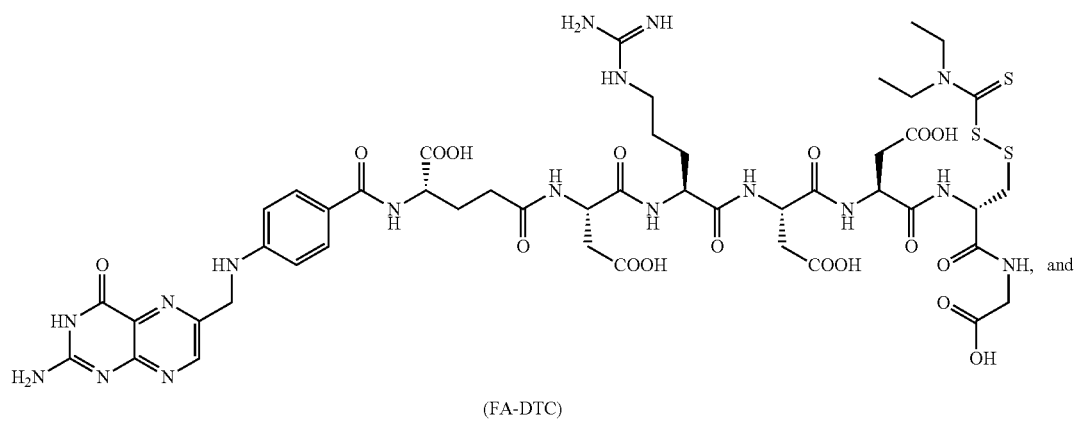
(FA-DTC)

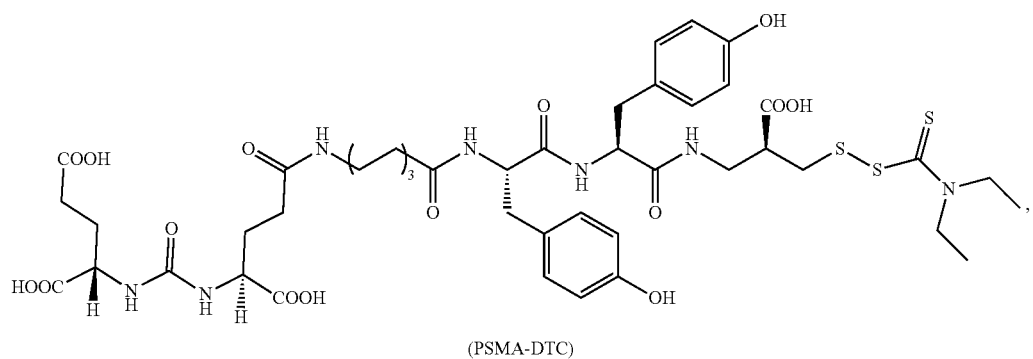
(PSMA-DTC)

or a pharmaceutically accept salt, amide, or ester thereof.

Clause 18. A pharmaceutical composition comprising an effective amount of a compound of any one of clauses 1-17, or a pharmaceutically accept salt, amide, or ester thereof, and a pharmaceutically acceptable carrier.

Clause 19. The pharmaceutical composition of claim 18, comprising an effective amount of a compound selected from the group consisting of

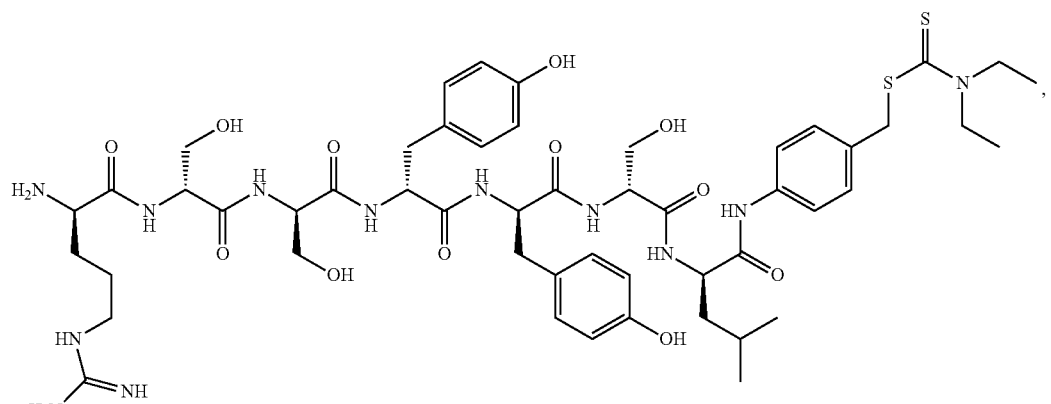
(PSA-DTC)

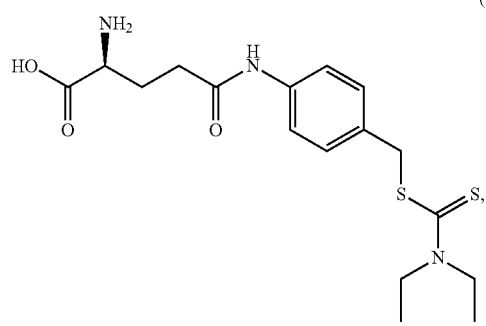
(Glu-DTC)

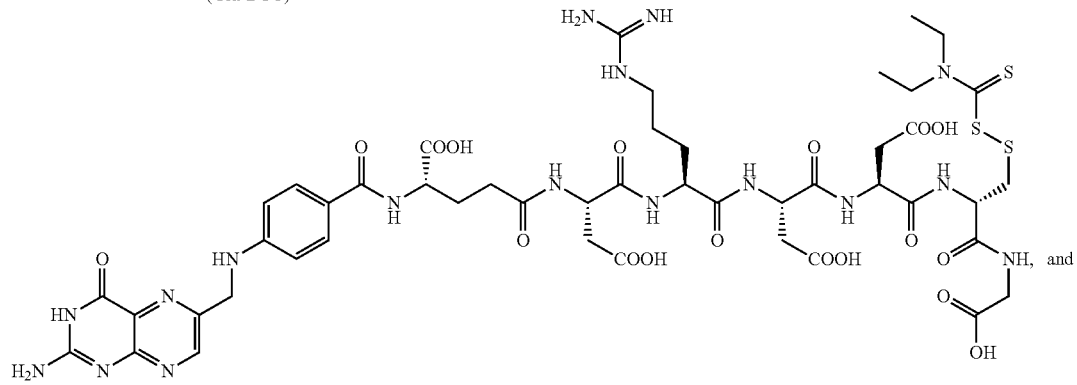
(FA-DTC)

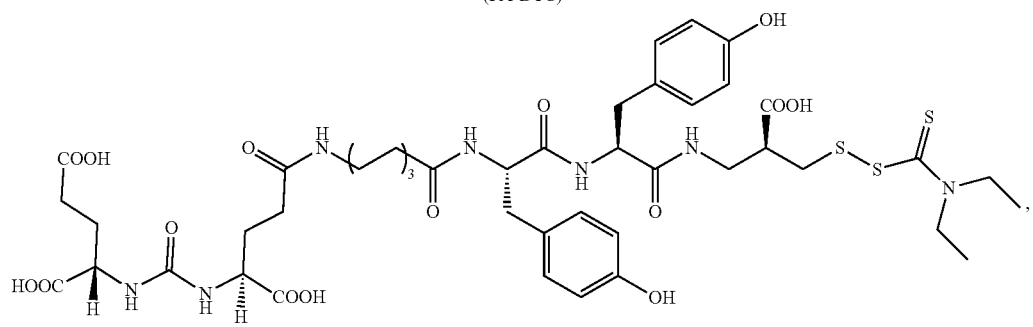
(PSMA-DTC)

or a pharmaceutically accept salt, amide, or ester thereof.

Clause 20. A method of treating cancer in a subject in need thereof, comprising administering to the subject a therapeutically effective amount of a compound of any one of clauses 1-17, or a pharmaceutically accept salt, amide, or ester thereof, whereby the cancer is treated.

Clause 21. A method of preventing cancer in a subject in need thereof, comprising administering to the subject a therapeutically effective amount of a compound of any one of clauses 1-17, or a pharmaceutically accept salt, amide, or ester thereof, whereby the cancer is prevented.

Clause 22. A method of attenuating a cancer in a subject in need thereof, comprising administering to the subject a therapeutically effective amount of a compound of any one of clauses 1-17, or a pharmaceutically accept salt, amide, or ester thereof such that the cancer is attenuated.

Clause 23. The method according to any one of clauses 20-22, wherein the cancer is prostate cancer.

Clause 24 The method according to any one of clauses 20-23, comprising administering to the subject a therapeutically effective amount of a compound selected from the group consisting of

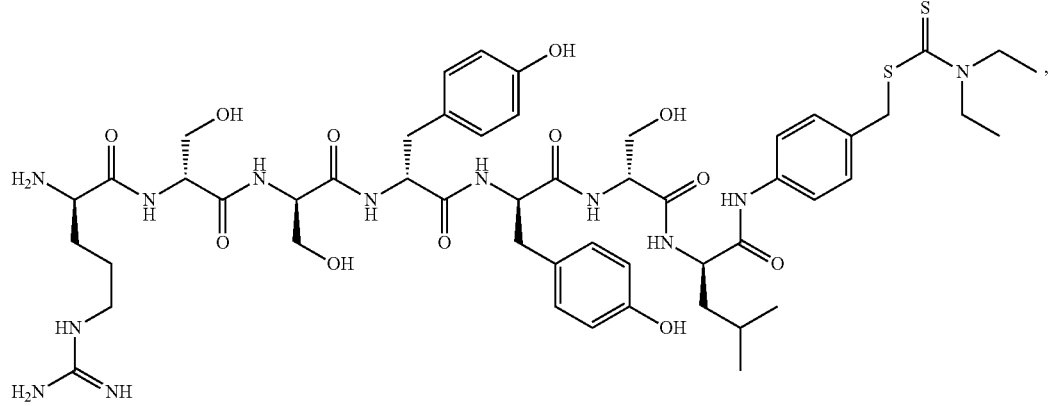
(PSA-DTC)

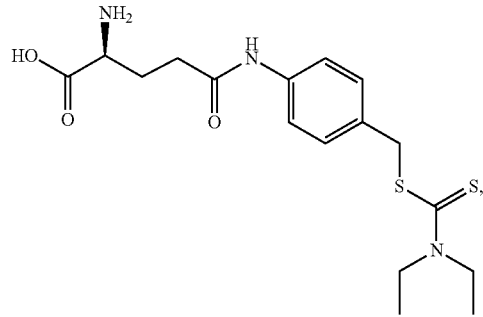
(Glu-DTC)

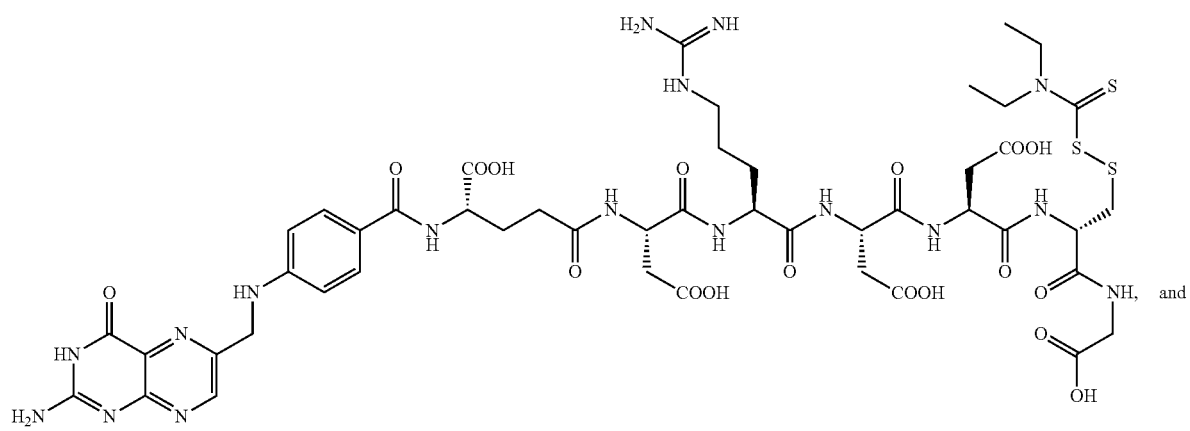
(FA-DTC)

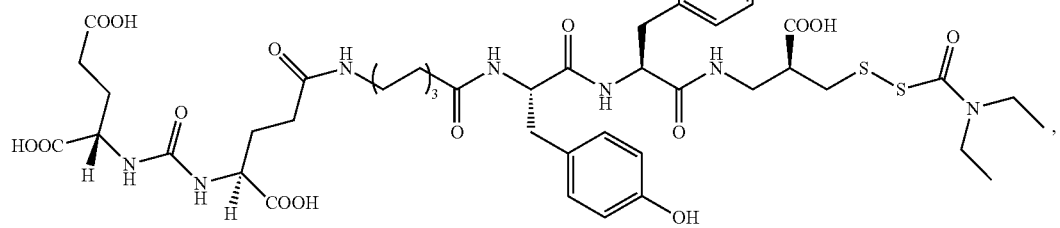

(PSMA-DTC)

or a pharmaceutically accept salt, amide, or ester thereof.

Clause 25. The method according to any one of clauses 20-24, further comprises administering to the subject an anticancer therapy selected from the group consisting of radiation, chemotherapy, immunotherapy, targeted therapy, hormone therapy, surgery, stem cell transplants, precision medicine, and combinations thereof.

Clause 26. The method according to clause 25, wherein the anticancer therapy is administered prior to the administration of the compound, or a pharmaceutically accept salt, amide, or ester thereof.

Clause 27. The method according to clause 25, wherein the anticancer therapy is administered concurrently with the administration of the compound, or a pharmaceutically accept salt, amide, or ester thereof.

Clause 28. The method according to claim 25, wherein the anticancer therapy is administered after the administration of the compound, or a pharmaceutically accept salt, amide, or ester thereof.

Clause 29. A kit for the treatment of a cancer comprising a compound of any one of clauses 1-17, or a pharmaceutically accept salt, amide, or ester thereof, instruments for the administration of the compound, and instructions for use.

What is claimed is:

1. A compound of formula (I),

T—L—S—C(=S)—N(Et)(Et)  (I)

or a pharmaceutically accept salt thereof, wherein

T is selected from the group consisting of (SEQ ID. No. 6)

[structure: HO-C(=O)-CH(NH₂)-CH₂-CH₂-C(=O)-],

-continued
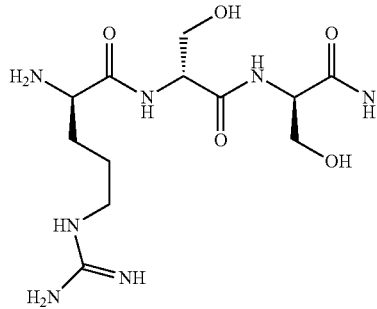
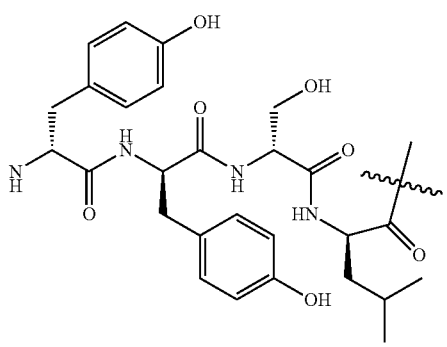
and
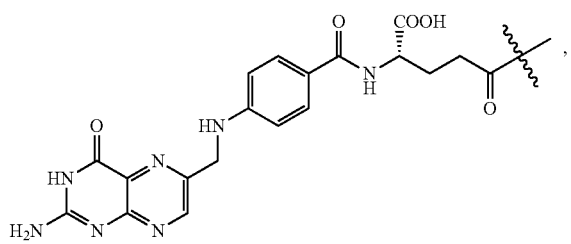
and
L is
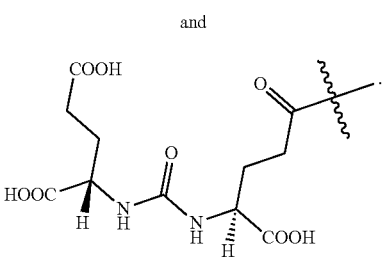
W, or —NH(CH$_2$)$_n$C(O)—W;
W is
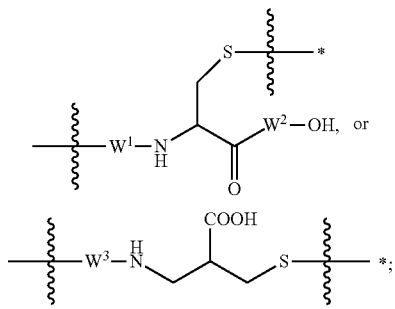
* indicates the attachment to
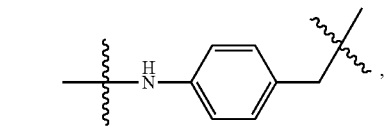
W$^1$, W$^2$, and W$^3$ are each independently a bond, an amino acid, or a peptide; and
n is 1, 2, 3, 4, 5, 6, 7, 8, 9, or 10.
2. The compound of claim 1, or a pharmaceutically accept salt thereof, wherein L is
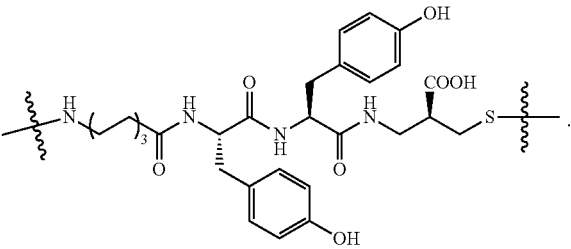
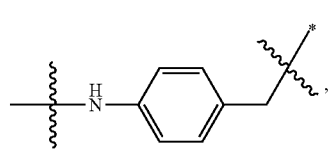 [SMILES: *Cc1ccc(N*)cc1]
3. The compound of claim 1, or a pharmaceutically accept salt thereof, wherein T is

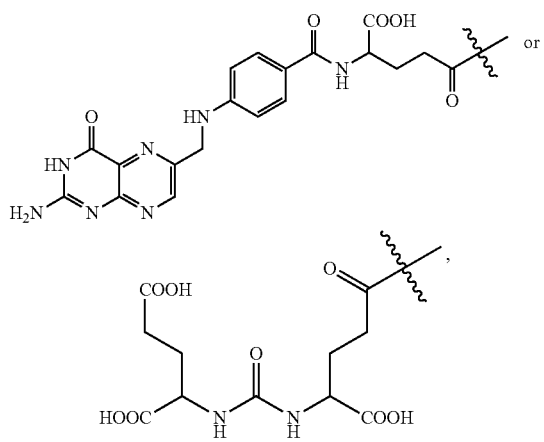

and L is W or —NH(CH$_2$)$_n$C(O)—W.

4. The compound of claim 1, or a pharmaceutically accept salt thereof, wherein T is

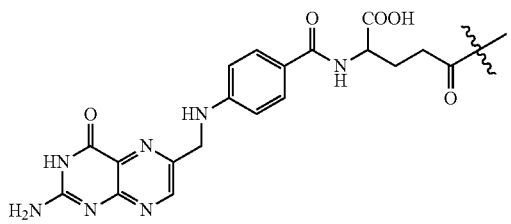 [SMILES: *C(=O)CCC(NC(=O)c1ccc(NCc2cnc3nc(N)[nH]c(=O)c3n2)cc1)C(=O)O]

and L is W.

5. The compound of claim 4, or a pharmaceutically accept salt thereof, wherein W is

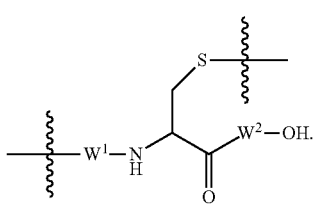

6. The compound of claim 5, or a pharmaceutically accept salt thereof, wherein W$^1$ and W$^2$ are each independently an amino acid or a peptide having 2-8 amino acids.

7. The compound of claim 1, or a pharmaceutically accept salt thereof, wherein T is

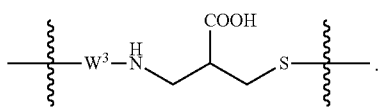

and L is —NH(CH$_2$)$_n$C(O)—W.

8. The compound of claim 7, or a pharmaceutically accept salt thereof, wherein W is 9. The compound of claim 8, or a pharmaceutically accept salt thereof, wherein W$^3$ is an amino acid or a peptide having 2-6 amino acids.

10. The compound of claim 1, selected from the group consisting of

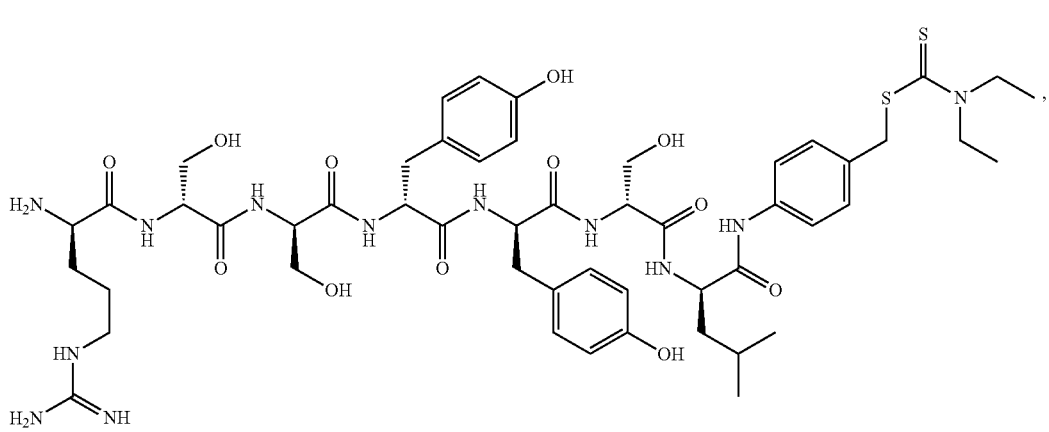

(PSA-DTC)

-continued

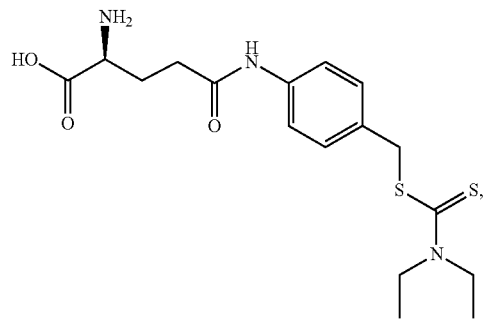
(Glu-DTC)

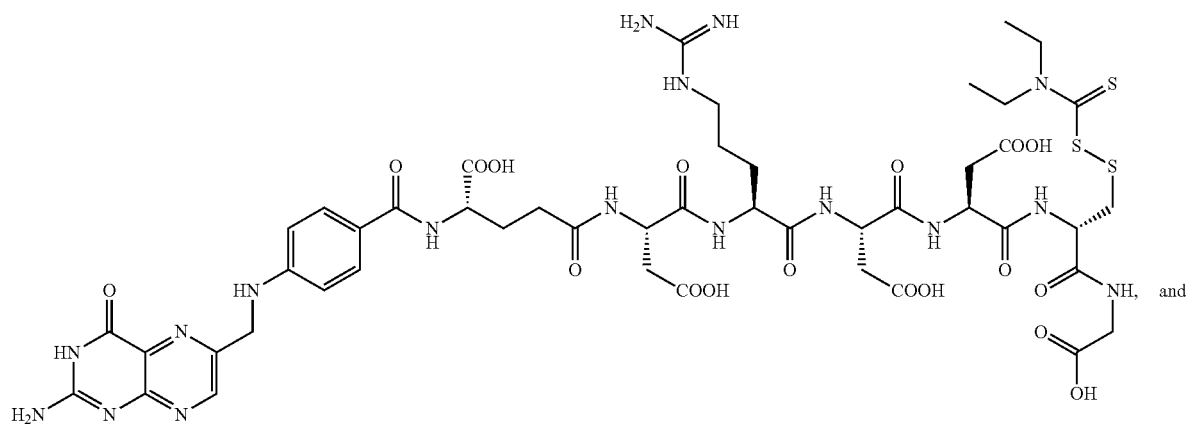
(FA-DTC) and

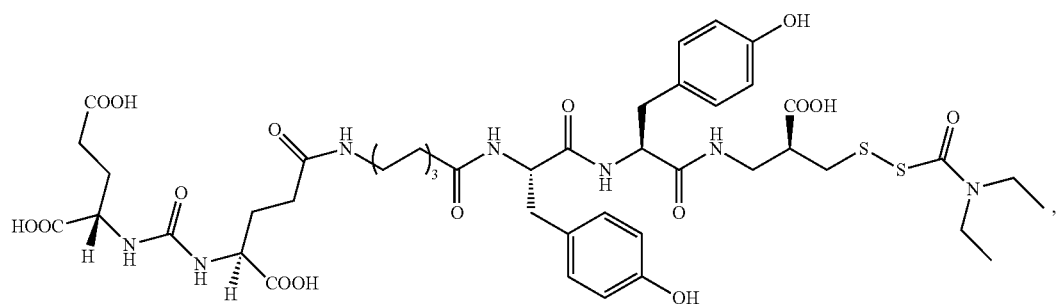
(PSMA-DTC), or a pharmaceutically accept salt thereof.

11. A pharmaceutical composition comprising an effective amount of a compound of claim 1, or a pharmaceutically accept salt thereof, and a pharmaceutically acceptable carrier.

12. The pharmaceutical composition of claim 11, comprising an effective amount of a compound selected from the group consisting of

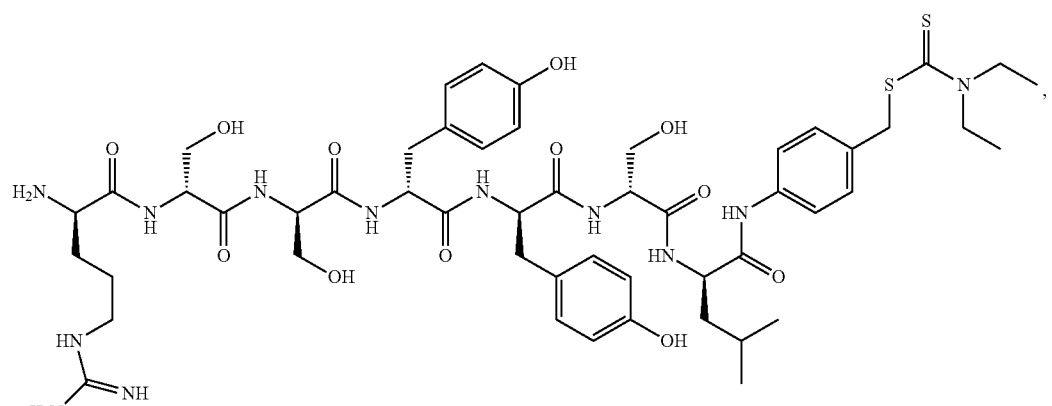

(PSA-DTC)

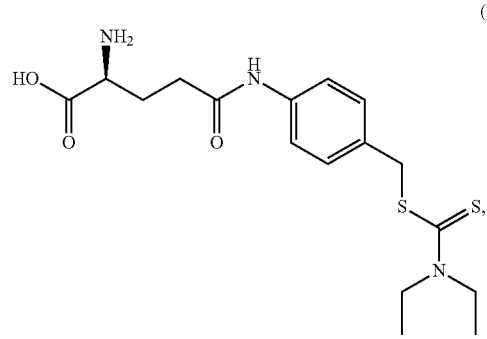

(Glu-DTC)

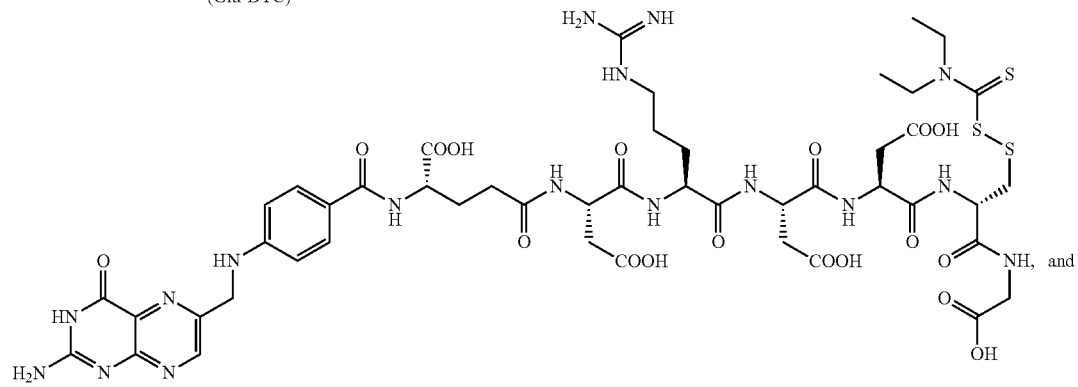

(FA-DTC)

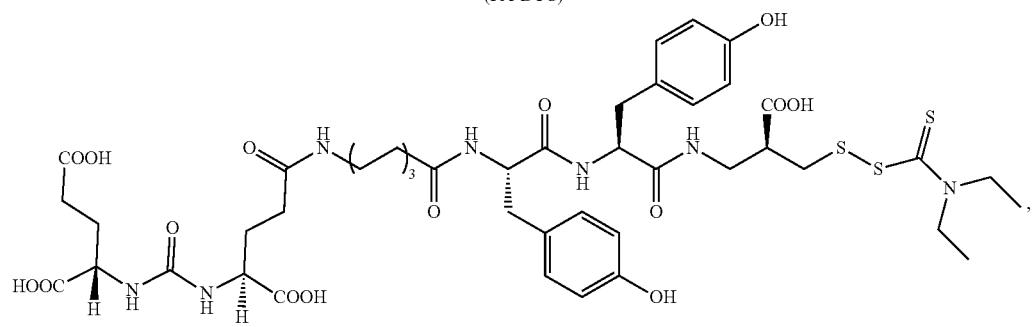

(PSMA-DTC)

or a pharmaceutically accept salt thereof.

13. A method of treating cancer in a subject in need thereof, comprising administering to the subject a therapeutically effective amount of a compound of claim 1, or a pharmaceutically accept salt thereof, whereby the cancer is treated, wherein the cancer is prostate cancer.

14. A method of attenuating a cancer in a subject in need thereof, comprising administering to the subject a therapeutically effective amount of a compound of claim 1, or a pharmaceutically accept salt thereof such that the cancer is attenuated, wherein the cancer is prostate cancer.

* * * * *